(12) United States Patent
Adams et al.

(10) Patent No.: US 10,364,266 B2
(45) Date of Patent: Jul. 30, 2019

(54) COMPOUNDS

(71) Applicant: GLAXOSMITHKLINE INTELLECTUAL PROPERTY DEVELOPMENT LIMITED, Brentford, Middlesex (GB)

(72) Inventors: Jerry Adams, Collegeville, PA (US); Yiqian Lian, Collegeville, PA (US)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 18 days.

(21) Appl. No.: 15/979,729

(22) Filed: May 15, 2018

(65) Prior Publication Data

US 2018/0258132 A1 Sep. 13, 2018

Related U.S. Application Data

(63) Continuation of application No. 15/586,634, filed on May 4, 2017, now Pat. No. 9,994,607, which is a continuation of application No. 15/368,921, filed on Dec. 5, 2016, now Pat. No. 9,718,848, which is a continuation of application No. PCT/IB2016/057265, filed on Dec. 1, 2016.

(60) Provisional application No. 62/332,517, filed on May 6, 2016, provisional application No. 62/327,579, filed on Apr. 26, 2016, provisional application No. 62/299,704, filed on Feb. 25, 2016, provisional application No. 62/299,253, filed on Feb. 24, 2016, provisional application No. 62/262,668, filed on Dec. 3, 2015.

(51) Int. Cl.
| | |
|---|---|
| *C07H 21/02* | (2006.01) |
| *C07H 21/04* | (2006.01) |
| *C07F 9/6574* | (2006.01) |
| *A61K 39/39* | (2006.01) |
| *C07H 21/00* | (2006.01) |
| *A61K 31/7084* | (2006.01) |
| *A61K 39/00* | (2006.01) |

(52) U.S. Cl.
CPC ......... *C07H 21/04* (2013.01); *A61K 31/7084* (2013.01); *A61K 39/39* (2013.01); *C07F 9/65746* (2013.01); *C07H 21/00* (2013.01); *C07H 21/02* (2013.01); *A61K 2039/55511* (2013.01)

(58) Field of Classification Search
None
See application file for complete search history.

(56) References Cited

U.S. PATENT DOCUMENTS 5,547,941 A 8/1996 Battistini et al.
2005/0187278 A1 8/2005 Taylor
2005/0203051 A1 9/2005 Karaolis et al.
2006/0167241 A1 7/2006 Hayakawa
2007/0244059 A1 10/2007 Karaolis
2008/0286296 A1 11/2008 Ebensen et al.
(Continued)

FOREIGN PATENT DOCUMENTS

WO WO2005/087238 9/2005
WO WO2007/054279 5/2007
(Continued)

OTHER PUBLICATIONS

Ablasser, et al., Nature, "cGAS produces a 2'—5'—linked cyclic dinucleotide second messenger that activates STING," (498)7454:380-384 (2013).
Barker, et al., *mBio*, "Sting-Dependent Recognition of Cyclic di-AMP Mediates Type I Interferon Responses during Chlamydia trachomatis Infection", 4(3):e00018 (2013).
Burdette, et al., *Nature Immunology*, "STING and the innate immune response to nucleic acids in the cytosol", 14:19-26 (2013).
Cai, et al., *Molecular Cell*, "The cGAS-cGAMP-STING Pathway of Cytosolic DNA Sensing and Signaling", 54:289-296 (2014).
(Continued)

*Primary Examiner* — Traviss C McIntosh, III
(74) *Attorney, Agent, or Firm* — Wayne J. Dustman; Fang Qian

(57) ABSTRACT

A compound of Formula (I)

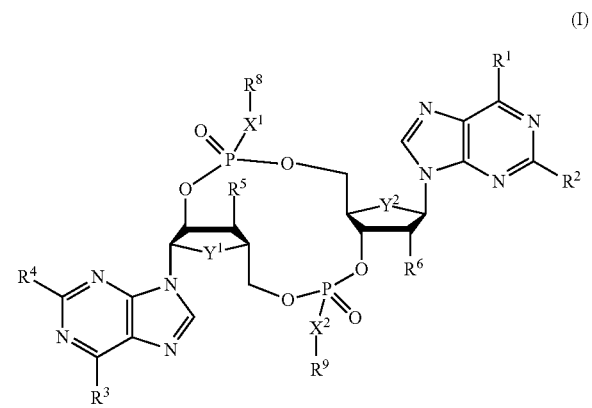

wherein $Y^1$, $Y^2$, $X^1$, $X^2$, $R^1$, $R^2$, $R^3$, $R^4$, $R^5$, $R^6$, $R^8$, and $R^9$ are as defined herein;
and pharmaceutically acceptable salts and tautomers thereof, compositions, combinations and medicaments containing said compounds and processes for their preparation. The invention also relates to the use of said compounds, combinations, compositions and medicaments, in the treatment of diseases in which modulation of STING (Stimulator of Interferon Genes) is beneficial, for example inflammation, allergic and autoimmune diseases, infectious diseases, cancer, pre-cancerous syndromes and as vaccine adjuvants.

11 Claims, 4 Drawing Sheets

(56) References Cited

U.S. PATENT DOCUMENTS

| | | |
|---|---|---|
| 2009/0169609 A1 | 7/2009 | Ebensen et al. |
| 2012/0164107 A1 | 6/2012 | Portnoy et al. |
| 2012/0178710 A1 | 7/2012 | Jones et al. |
| 2012/0288515 A1 | 11/2012 | Robbins et al. |
| 2013/0266612 A1 | 10/2013 | Fukasaka et al. |
| 2014/0170689 A1 | 6/2014 | Nesbitt et al. |
| 2014/0205653 A1 | 7/2014 | Dubensky, Jr. et al. |
| 2014/0329889 A1 | 11/2014 | Vance et al. |
| 2014/0341976 A1 | 11/2014 | Dubensky, Jr. et al. |
| 2015/0010613 A1 | 1/2015 | Dubensky, Jr. et al. |
| 2015/0056224 A1 | 2/2015 | Dubensky, Jr. et al. |
| 2015/0158886 A1 | 6/2015 | Jones et al. |
| 2015/0343056 A1 | 12/2015 | Chen et al. |
| 2016/0068560 A1 | 3/2016 | Patel et al. |
| 2016/0074507 A1 | 3/2016 | Manel et al. |
| 2016/0220652 A1 | 8/2016 | Petit et al. |

FOREIGN PATENT DOCUMENTS

| | | | |
|---|---|---|---|
| WO | WO 2009/133560 | 11/2009 | |
| WO | WO 2013/086331 | 6/2013 | |
| WO | WO2013/166000 | 11/2013 | |
| WO | WO2013/185052 | 12/2013 | |
| WO | WO2014/093936 | 6/2014 | |
| WO | WO 2014/189805 | 11/2014 | |
| WO | WO 2015/017652 | 2/2015 | |
| WO | WO 2015/074145 A1 | 5/2015 | |
| WO | WO 2015/077354 A1 | 5/2015 | |
| WO | WO 2015/108595 | 7/2015 | |
| WO | WO 2015/161762 | 10/2015 | |
| WO | WO 2015/185565 A1 | 12/2015 | |
| WO | WO 2015/187009 A1 | 12/2015 | |
| WO | 2016/096174 A1 † | 6/2016 | |
| WO | WO 2016/096174 A1 | 6/2016 | |
| WO | WO 2016/096577 A1 | 6/2016 | |
| WO | WO 2016/100261 A2 | 6/2016 | |
| WO | WO 2016/115480 | 7/2016 | |
| WO | WO 2016/120305 | 8/2016 | |
| WO | WO 2016/123573 | 8/2016 | |
| WO | WO 2016/131048 | 8/2016 | |
| WO | WO 2016/145102 | 9/2016 | |
| WO | WO 2017/011622 A1 | 1/2017 | |
| WO | WO2017/027645 A1 | 2/2017 | |
| WO | WO2017/027646 A1 | 2/2017 | |
| WO | WO 2017/075477 A1 | 5/2017 | |
| WO | WO-2017075477 A1 * | 5/2017 | ............ A61K 39/12 |
| WO | WO 2017/161349 A1 | 9/2017 | |
| WO | WO 2017/186711 A1 | 11/2017 | |
| WO | WO 2018/009652 A1 | 1/2018 | |
| WO | WO 2018/013887 A1 | 1/2018 | |
| WO | WO 2018/013908 A1 | 1/2018 | |

OTHER PUBLICATIONS

Carroll, et al., *Immunity*, "The Vaccine Adjuvant Chitosan Promotes Cellular Immunity via DNA Sensor cGAS-STING-Dependent Induction of Type I Inferferons," 44:597-608 (2016).
Chang, et al., *Antiviral Research*, "Treatment of chronic hepatitis B with pattern recognition receptor agonists: Current status and potential for a cure", 121:152-159 (2015).
Che, et al., *The Journal of Physical Chemistry B*, "Structural Flexibility and Conformation Features of Cyclic Dinucleotides in Aqueous Solutions," 120(10):2670-2680 (2016).
Chen, et al., *Nature Immunology*, "Regulation and function of the cGAS-STING pathway of cytosolic DNA sensing", 10:1142-1149 (2016).
Chen, et al., *Science*, "Pivotal Roles of cGAS-gGAMP Signaling in Antiviral Defense and Immune Adjuvant Effects", 341:1390-1394 (2013).
Collins, et al., *Cell Host Microbe*, "Cyclic GMP-AMP Synthase (cGAS) Is an Innate Immune DNA Sensor for *Myobacterium tuberculosis*", 17(6):820-828 (2015).
Crow, et al., *Nature Genetics*, 38:917-920 (2006).
Danasko, et al., *FEBS J.*, "The cyclic GMP-AMP synthetase-STING signaling pathway is required for both the innate immune response against HBV and the suppression of HBV assembly," 283:144-156 (2016).
Diner, et al., *Cell Reports*, "The Innate Immune DNA Sensor cGAS Produces a Noncanonical Cyclic Dinucleotide that Activates Human STING," 3(5):1355-1361 (2013).
Dubensky, et al., *Therapeutic Advances in Vaccines*, "Raionale, progress and development of vaccines utilizing STING-activating cyclic dinucleotide adjuvants", published on line Sep. 5, 2013.
Fu, et al., *Science Translational Medicine*, "STING agonist formulated cancer vaccines can cure established tumors resistant to PD-1 blockade", 7(283):1-13 (2015).
Gao, et al., *Cell*, "Cyclic [G(2',5')pA(3',5')p] Is the Metazoan Second Messenger Produced by DNA-Activated Cyclic GMP-AMP Synthase", 153:1094-1107 (2013).
Gao, et al., *Science*, "Cyclic GMP-AMP Synthase Is an Innate Immune Sensor of HIV and Other Retroviruses", 341:903-6 (2013).
Guo, et al., *Antimicrobial Agents and Chemotherapy*, "Sting agonists induce an innate antiviral immune response against hepatitis B virus", 59(2):1273-1281 (2015).
Guo, et al., *Cell Host and Microbe*, "NLRX1 Sequesters STING to Negatively Regulate the Interferon Response, Thereby Facilitating the Replication of HIV-1 and DNA Viruses", 19(4):515-528 (2016).
Herzner, et al., *Nature Immunology*, "Sequence-specific activation of the DNA sensor cGAS by Y-form DNA structures as found in primary HIV-1 cDNA", 16(10):1025-1033 (2015).
Holm, et al., *Nature Communications*, "Influenza a virus targets a cGAS-independent STING pathway that controls enveloped RNA viruses", 7:10680 (2016).
Huber, et al., *The Journal of Immunology*, "Cutting Edge: Type I IFN Reverses Human Th2 Commitment and Stability by Suppressing GATA3", 185:813-817 (2010).
Huang, et al., *Journal of Immunology*, "Cutting edge: DNA sensing via the STING adaptor in myeloid dendritic cells induces potent tolerogenic responses", 191:3509-3513 (2013).
Isaacs, et al., *Proceedings of the Royal Society B: Biological Sciences*, "Virus Interference. I. The Interferon", 147(927):258-267 (1957).
Ishikawa, et al., *Nature*, "STING is an endoplasmic reticulum adaptor that facilitates innate immune signaling", 455:674-678 (2008).
Jin, et al., *Journal of Immunology*, "MPYS Is Required for IFN Response Factor 3 Activation and Type I IFN Production in the Response of Cultured Phagocytes to Bacterial Second Messengers Cyclic-di-AMP and Cyclic-di-GMP", 187:2595-2601 (2011).
Kidd, et al., *Alternative Medical Review*, "Th1/Th2 balance: the hypothesis, its limitations, and implications for health and disease", 8:223-246 (2003).
Lau, et al., *Science*, "DNA tumor virus oncogenes antagonize the cGAS-Sting DNA-sensing pathway", 350:568-571 (2015).
Lemos, et al., *Journal of Immunology*, "Activation of the STING adaptor attenuates experimental autoimmune encephalitis", 192:5571-5578 (2014).
Li, et al., *Science*, "Pivotal rolels of cGAS-cGAMP signaling in antiviral defense and immune adjuvant effect", 341:1390-1394 (2013).
Li, et al., *Immunity*, "Cyclic GMP-AMP Synthase Is Activated by Double-Stranded DNA-Inducted Oligomerization," 39(6):1019-1031 (2013).
Li, et al., *Nature Chemical Biology*, "Hydrolysis of 2'3"—cGAMP by ENPP1 and design of nonhydrolyzable analogs," 10(12):1043-1048 (2014).
Libanova, et al., *Microbial Biotechnology*, "Cyclic di-nucleotides: new era for small molecules as adjuvants", 5(2):168-176 (2011).
Luo, et al., *Molecular Biosystems*, "Selective binding of 2'-F-c-di-GMP to Ct-E88 and Cb-E43, new class I riboswitches from Clostridium tetani and Clostridium botulinum respectively", 9(6):1535 (2013).
Moisan, et al., *Am. J. Physiol. Lung Cell Mol. Physiol.*, "TLR7 ligand prevents allergen-induced airway hyperresponsiveness and eosinophilia in allergic asthma by a MYD88-dependent and MK2-independent pathway", 290:L987-995 (2006).

(56) References Cited

OTHER PUBLICATIONS

Nissen, et al., *Clinical and Experimental Immunology*, "Innate DNA sensing is impaired in HIV patients and IFI16 expression correlates with chronic immune activation", 177:295-309 (2014).
Nitta, et al., *Hepatology*, "Hepatitis C virus NS4B protein targets Sting and abrogates RIG-I-mediated type I interferon-dependent innate immunity", 57:46-58 (2013).
Persing, et al., *Trends in Microbiology*, "Taking toll: lipid A mimetics as adjuvants and immunomodulators", 10(10) (Suppl)., S32-S37 (2002).
Prantner, et al., *The Journal of Immunology*, Stimulator of IFN Gene Is Critical for Induction of IFN-B during Chlamydia muridarum Infection:, 184:2551-2560 (2010).
Rakoff-Nahoum, et al., *Cell*, "Recognition of Commensal Microflora by Toll-Like Receptors Is Required for Intestinal Homeostasis", 118(2):229-241 (2004).
Shanahan, et al., *Journal of the American Chemical Society*, "Differential Analogue Binding by Two Classes of c-di-GMP Riboswitches", 133(39):15578-15592 (2011).
Sharma, et al., *Immunity*, "Innate Immune Recognition of an AT-Rich Stem-Loop DNA Motif in the Plasmodium falciparum Genome", 35(2):194-207 (2011).
Shi, et al., *Proceedings of the National Academy of Sciences*, "Molecular basis for the specific recognition of the metazoan cyclic GMP-AMP by the innate immune adaptor protein STING," 112(29):8947-8952 (2015).
Shirey, et al.,*Journal of Leukocyte Biology*, "The anti-tumor agent, 5,6-dimethylxanthenone-4-acetic acid (DMXAA), induces IFN-beta-mediated antiviral activity in vitro and in vivo", 89:351-357 (2011).
Stetson, et al., *Cell*, 134(4):587-598 (2008).
Storek, et al., *The Journal of Immunology*, "cGAS and Ifi204 Cooperate to Produce Type I IFNs in Response to Francisella Infection", 194:3236-3245 (2015).
Sun, et al., *Science*, "Cyclic GMP-AMP Synthase is a Cytosolic DNA Sensor That Activates the Type I Interferon Pathway", 339:786-791 (2013).

Sunthamala, et al., *PLoS One*, "E2 Proteins of High Risk Human Papillomaviruses DownModulate STING and IFN-k Transcription in Keratinocytes", 9(3):e91473 (2014).
Takeuchi O., et al., *Cell*, "Pattern Recognition Receptors and Inflammation",140:805-820 (2010).
Tezuka, et al., *Chemistry Letters*, "Synthesis of 2'-Modified Cyclic Bis(3'-5')diadenylic Acids and Their Promotion of Cell Division in a Freshwater Green Alga", 41(12):1723-1725 (2012).
Wang, et al., *The Journal of Investigative Dermatology*, "Natural STING Agonist as an "Ideal" Adjuvant for Cutaneous Vaccination", 136:2183-2191 (2016).
Wassermann, et al., *Cell Host and Microbe*, "Mycobacterium tuberculosis Differentially Activates cGAS-and Inflammasome-Dependent Intracellular Immune Responses through ESX-1", 17(6):799-810 (2015).
Watson, et al., *Cell Host & Microbe*, "The Cytosolic Sensor cGAS Detects *Mycobacterium tuberculosis* DNA to Induce Type I Interferons and Activate Autophagy," 17:811-819 (2015).
Wu, et al., *Science*, "Cyclic GMP-AMP is an Endogenous Second Messenger in Innate Immune Signaling by Cytosolic DNA", 339:826-830 (2013).
Yi, et al., *PLoS One*, "Single Nucleotide Polymorphisms of Human STING Can Affect Innate Imune Response to Cyclic Dinucleotides," 8(10):e77846 (2013).
Zhang, et al., *Molecular Cell*, "Cyclic GMP-AMP Containing Mixed Phosphodiester Linkages Is an Endogenous High-Affinity Ligand for STING," 51(2):226-235 (2013).
Zhang, et al., *The Journal of Immunology*, "The DNA Sensor, Cyclic GMP-AMP synthase, Is Essential for Induction of IFN-B during Chlamydia trachomatis Infection", 193:2394-2404 (2014).
Zitvogel, et al., *Nature Reviews Immunology*, "Type I interferons in anticancer immunity", 15(7):405-414 (2015).
U.S. Appl. No. 62/332,517.†
U.S. Appl. No. 62/262,668.†
U.S. Appl. No. 62/299,253.†
U.S. Appl. No. 62/299,704.†
U.S. Appl. No. 62/327,579.†

\* cited by examiner
† cited by third party

COMPOUNDS

This application is a continuation of U.S. application Ser. No. 15/586,634 filed on May 4, 2017, which is a continuation of U.S. application Ser. No. 15/368,921 filed on Dec. 5, 2016, and issued on Aug. 1, 2017, U.S. Pat. No. 9,718, 848, which is a continuation of PCT/IB2016/057265 filed on Dec. 1, 2016, which claims the benefit of U.S. Provisional 62/332,517 filed on May 6, 2016, U.S. Provisional 62/327, 579 filed on Apr. 26, 2016, U.S. Provisional 62/299,704 filed on Feb. 25, 2016, U.S. Provisional 62/299,253 filed on Feb. 24, 2016, and U.S. Provisional 62/262,668 filed on Dec. 3, 2015, all of which are incorporated herein in their entirety.

FIELD OF THE INVENTION

The present invention relates to compounds, compositions, combinations and medicaments containing said compounds and processes for their preparation. The invention also relates to the use of said compounds, combinations, compositions and medicaments, in the treatment of diseases in which modulation of STING (Stimulator of Interferon Genes) is beneficial, for example inflammation, allergic and autoimmune diseases, infectious diseases, human immunodeficiency virus (HIV) infection, AIDS, cancer, pre-cancerous syndromes and as immugenic composition or vaccine adjuvants.

BACKGROUND TO THE INVENTION

Vertebrates are constantly threatened by the invasion of microorganisms and have evolved mechanisms of immune defence to eliminate infective pathogens. In mammals, this immune system comprises two branches; innate immunity and adaptive immunity. The innate immune system is the first line of defence which is initiated by Pattern Recognition Receptors (PRRs) which detect ligands from the pathogens as well as damage associated molecular patterns (Takeuchi O. et al, Cell, 2010: 140, 805-820). A growing number of these receptors have been identified including Toll-like receptors (TLRs), C-type lectin receptors, retinoic acid inducible gene I (RIG-I)-like receptors and NOD-like receptors (NLRs) and also double stranded DNA sensors. Activation of PRRs leads to up-regulation of genes involved in the inflammatory response including type 1 interferons, pro-inflammatory cytokines and chemokines which suppress pathogen replication and facilitate adaptive immunity.

The adaptor protein STING (Stimulator of Interferon Genes), also known as TMEM 173, MPYS, MITA and ERIS, has been identified as a central signalling molecule in the innate immune response to cytosolic nucleic acids (Ishikawa H and Barber G N, Nature, 2008: 455, 674-678; WO2013/1666000). Activation of STING results in up-regulation of IRF3 and NFκB pathways leading to induction of Interferon-β and other cytokines. STING is critical for responses to cytosolic DNA of pathogen or host origin, and of unusual nucleic acids called Cyclic Dinucleotides (CDNs)

CDNs were first identified as bacterial secondary messengers responsible for controlling numerous responses in the prokaryotic cell. Bacterial CDNs, such as c-di-GMP are symmetrical molecules characterised by two 3',5' phophodiester linkages.

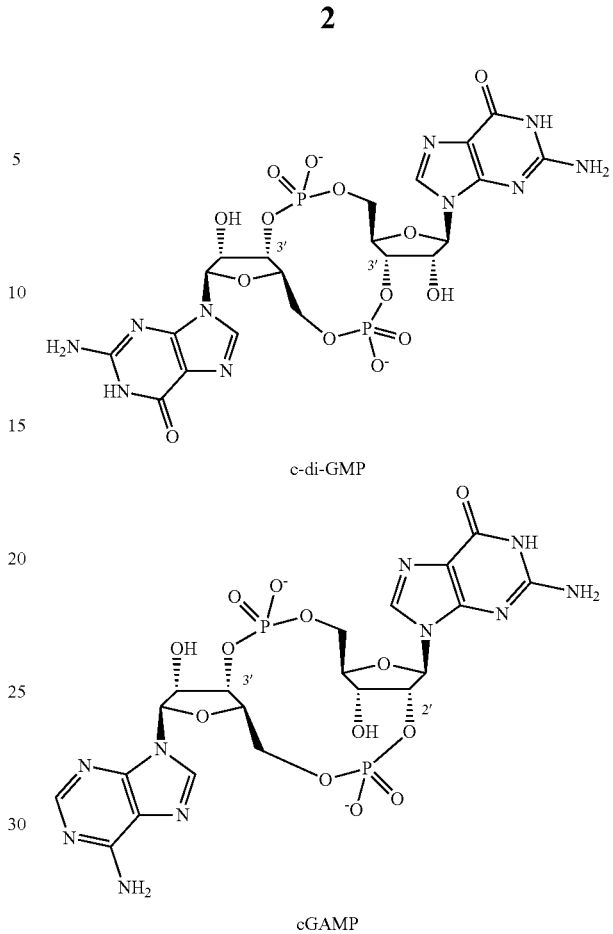

c-di-GMP cGAMP

Direct activation of STING by bacterial CDNs has recently been confirmed through X-ray crystallography (Burdette D L and Vance R E, Nature Immunology, 2013: 14, 19-26). Bacterial CDNs and their analogues have consequently attracted interest as potential vaccine adjuvants (Libanova R. et al, Microbial Biotechnology 2012: 5, 168-176; WO2007/054279, WO2005/087238).

More recently, the response to cytosolic DNA has been elucidated and shown to involve generation, by an enzyme called cyclic GMP-AMP synthase (cGAS, previously known as C6orf150 or MB21D1), of a novel mammalian CDN signalling molecule identified as cGAMP, which then activates STING. Unlike bacterial CDNs, cGAMP is an unsymmetrical molecule characterised by it's mixed 2',5' and 3',5' phosphodiester linkages. (Gao P et al, Cell, 2013: 153, 1-14). Interaction of cGAMP with STING has also been demonstrated by X-ray crystallography (Cai X et al, Molecular Cell, 2014: 54, 289-296).

Interferon was first described as a substance which could protect cells from viral infection (Isaacs & Lindemann, J. Virus Interference. Proc. R. Soc. Lon. Ser. B. Biol. Sci. 1957: 147, 258-267). In man, the type I interferons are a family of related proteins encoded by genes on chromosome 9 and encoding at least 13 isoforms of interferon alpha (IFNα) and one isoform of interferon beta (IFNβ). Recombinant IFNα was the first approved biological therapeutic and has become an important therapy in viral infections and in cancer. As well as direct antiviral activity on cells, interferons are known to be potent modulators of the immune response, acting on cells of the immune system.

Administration of a small molecule compound which could stimulate the innate immune response, including the activation of type I interferons and other cytokines, could become an important strategy for the treatment or prevention of human diseases including viral infections. This type of immunomodulatory strategy has the potential to identify compounds which may be useful not only in infectious diseases but also in cancer (Zitvogel, L., et al., *Nature Reviews Immunology*, 2015 15(7), p 405-414), allergic diseases (Moisan J. et al, *Am. J. Physiol. Lung Cell Mol. Physiol.*, 2006: 290, L987-995), other inflammatory conditions such as irritable bowel disease (Rakoff-Nahoum S., *Cell.*, 2004, 23, 118(2): 229-41), and as vaccine adjuvants (Persing et al. *Trends Microbiol.* 2002: 10(10 Suppl), S32-7 and Dubensky et al., *Therapeutic Advances in Vaccines*, published on line Sep. 5, 2013).

Allergic diseases are associated with a Th2-biased immune-response to allergens. Th2 responses are associated with raised levels of IgE, which, via its effects on mast cells, promotes a hypersensitivity to allergens, resulting in the symptoms seen, for example, in allergic rhinitis and asthma. In healthy individuals the immune-response to allergens is more balanced with a mixed Th2/Th1 and regulatory T cell response. Induction of Type 1 interferons have been shown to result in reduction of Th2-type cytokines in the local environment and promote Th1/Treg responses. In this context, induction of type 1 interferons by, for example, activation of STING, may offer benefit in treatment of allergic diseases such as asthma and allergic rhinitis (Huber J. P. et al *J Immunol* 2010: 185, 813-817).

In contrast, increased and prolonged type I IFN production is associated with a variety of chronic infections, including Mycobacteria (Collins et al, CHM 2015; Wassermann et al., *CHM* 2015; Watson et al., *CHM* 2015), Franciscella (Storek et al., *JI* 2015; Jin et al., *JI* 2011), *Chlamydia* (Prantner et al., JI 2010; Barker et al., *Mbio* 2013; Zhang et al., *JI* 2014), *Plasmodium* (Sharma et al., Immunity 2011) and HIV (Herzner et al., *Nat Immunol* 2015; Nissen et al., *Clin Exp Immunol* 2014; Gao et al., *Science* 2013; Lahaye et al, *Science* 2013) (reviewed in Stiffer and Feng, *JI* 2014). Similarly, excess type I interferon production is found among patients with complex forms of autoimmune disease. Genetic evidence in humans and support from studies in animal models support the hypothesis that inhibition of STING results in reduced type I interferon that drives autoimmune disease (Crow Y J, et al., *Nat. Genet.* 2006; 38917-920, Stetson D B, et al., *Cell* 2008; 134; 587-598). Therefore, inhibitors of STING provide a treatment to patients with chronic type I interferon and proinflammatory cytokine production associated with infections or complex autoimmune diseases. Allergic diseases are associated with a Th2-biased immune-response to allergens.

Compounds that bind to STING and act as agonist have been shown to induce type 1 interferons and other cytokines on incubation with human PBMCs. Compounds which induce human interferons may be useful in the treatment of various diseases, for example the treatment of allergic diseases and other inflammatory diseases for example allergic rhinitis and asthma, the treatment of infectious diseases, pre-cancerous syndromes and cancer, and may also be useful as immugenic composition or vaccine adjuvants. Compounds that bind to STING may act as antagonists and could be useful in the treatment, for example of autoimmune diseases.

It is envisaged that targeting STING with activation or inhibiting agents may be a promising approach for treating diseases in which modulation for the type 1 IFN pathway is beneficial, including inflammatory, allergic and autoimmune diseases, infectious diseases, cancer, pre-cancerous syndromes and as immugenic composition or vaccine adjuvants.

International Patent Applications WO2014/093936, WO2014/189805, WO2013/185052, U.S.2014/0341976, WO 2015/077354, PCT/EP2015/062281 and GB 1501462.4 disclose certain cyclic di-nucleotides and their use in inducing an immune response.

It is an object of the invention to provide further cyclic di-nucleotides, suitably for the treatment of cancer.

SUMMARY OF THE INVENTION

The invention is directed to compounds according to Formula (I):

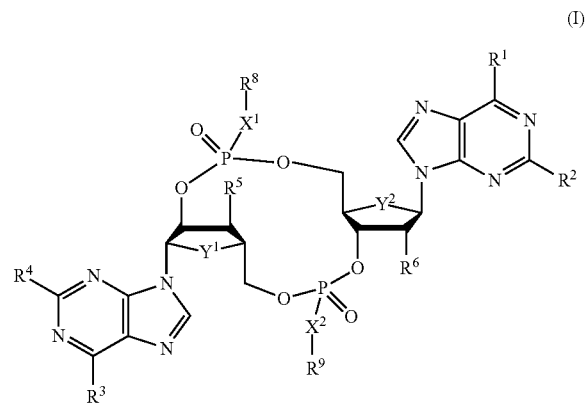

wherein $Y^1$, $Y^2$, $X^1$, $X^2$, $R^1$, $R^2$, $R^3$, $R^4$, $R^5$, $R^6$, $R^8$, and $R^9$ are as defined below and pharmaceutically acceptable salts thereof.

In a further aspect of the present invention, there is provided a pharmaceutical composition comprising a compound of Formula (I) or a pharmaceutically acceptable salt thereof and one or more of pharmaceutically acceptable excipients.

In a further aspect of the present invention, there is provided a compound of Formula (I), or a pharmaceutically acceptable salt thereof for use in therapy.

In a further aspect of the present invention, there is provided a compound of Formula (I), or a pharmaceutically acceptable salt thereof for use in the treatment of a disease in which modulation STING is beneficial.

In a further aspect of the present invention, there is provided a compound of Formula (I), or a pharmaceutically acceptable salt thereof for use in the treatment of inflammation, allergic and autoimmune diseases, infectious diseases, cancer, pre-cancerous syndromes and as immugenic composition or vaccine adjuvants.

In a further aspect of the present invention, there is provided a method of the treatment of a disease in which modulation STING is beneficial in a subject comprising administering a therapeutically effective amount of a compound of Formula (I) or a pharmaceutically acceptable salt thereof.

In a further aspect of the present invention, there is provided a method of the treating inflammation, allergic and autoimmune diseases, infectious diseases and cancer in a subject comprising administering a therapeutically effective amount of a compound of Formula (I) or a pharmaceutically acceptable salt thereof.

In a further aspect of the present invention, there is provided the use of a compound of Formula (I), or a pharmaceutically acceptable salt thereof in the manufacture of a medicament for use the treatment of a disease in which modulation of STING is beneficial.

In a further aspect of the present invention, there is provided the use of a compound of Formula (I), or a pharmaceutically acceptable salt thereof in the manufacture of a medicament for use the treatment of inflammation, allergic and autoimmune diseases, infectious diseases, pre-cancerous syndromes and cancer.

In a further aspect there is provided a combination comprising a compound of Formula (I) or a pharmaceutically acceptable salt thereof and at least one further therapeutic agent.

In a further aspect of the present invention, there is provided a pharmaceutical composition comprising a compound of Formula (I) or a pharmaceutically acceptable salt thereof and at least one further therapeutic agent and one or more of pharmaceutically acceptable excipients.

In a further aspect there is provided a combination comprising a compound of Formula (I) or a pharmaceutically acceptable salt thereof and at least one further therapeutic agent for use in therapy.

In a further aspect there is provided a combination comprising a compound of Formula (I) or a pharmaceutically acceptable salt thereof and at least one further therapeutic agent for use in the treatment of a disease or condition in which modulation of STING is beneficial.

In a further aspect there is provided a combination comprising a compound of Formula (I) or a pharmaceutically acceptable salt thereof and at least one further therapeutic agent for use in the treatment of inflammation, allergic and autoimmune diseases, infectious diseases, pre-cancerous syndromes and cancer.

In a further aspect of the present invention, there is provided a method of the treatment of a disease or condition in which modulation of STING is beneficial in a subject comprising administering a therapeutically effective amount of a a combination comprising a compound of Formula (I) or a pharmaceutically acceptable salt thereof and at least one further therapeutic agent.

In a further aspect of the present invention, there is provided a method of the treatment of inflammation, allergic and autoimmune diseases, infectious diseases and cancer in a subject comprising administering a therapeutically effective amount of a combination comprising a compound of Formula (I) or a pharmaceutically acceptable salt thereof and at least one further therapeutic agent.

In a further aspect of the present invention, there is provided an immugenic composition or vaccine adjuvant comprising a compound of Formula (I), or a pharmaceutically acceptable salt thereof.

In a further aspect of the invention, there is provided a composition comprising a compound of Formula (I), or a pharmaceutically acceptable salt thereof, and one or more immunostimulatory agents.

In a further aspect of the present invention, there is provided an immunogenic composition comprising an antigen or antigen composition and a compound of Formula (I), or a pharmaceutically acceptable salt thereof.

In a further aspect of the present invention, there is provided an immunogenic composition comprising an antigen or antigen composition and a compound of Formula (I), or a pharmaceutically acceptable salt thereof for use in the treatment or prevention of disease.

In a further aspect of the present invention, there is provided the use of a compound of Formula (I), or a pharmaceutically acceptable salt thereof, for the manufacture of an immunogenic composition comprising an antigen or antigen composition, for the treatment or prevention of disease.

In a further aspect of the present invention, there is provided a method of treating or preventing disease comprising the administration to a human subject suffering from or susceptible to disease, an immunogenic composition comprising an antigen or antigen composition and a compound of Formula (I), or a pharmaceutically acceptable salt thereof.

In a further aspect of the present invention, there is provided an immugenic or vaccine composition comprising an antigen or antigen composition and a compound of Formula (I), or a pharmaceutically acceptable salt thereof for use in the treatment or prevention of disease.

In a further aspect of the present invention, there is provided an immugenic composition comprising an antigen or antigen composition and a compound of Formula (I), or a pharmaceutically acceptable salt thereof for use in the treatment or prevention of disease.

In a further aspect of the present invention, there is provided the use of a compound of Formula (I), or a pharmaceutically acceptable salt thereof, for the manufacture of an immugenic or vaccine composition comprising an antigen or antigen composition, for the treatment or prevention of disease.

In a further aspect of the present invention, there is provided a method of treating or preventing disease comprising the administration to a human subject suffering from or susceptible to disease, a vaccine composition comprising an antigen or antigen composition and a compound of Formula (I), or a pharmaceutically acceptable salt thereof.

In a further aspect there is provided a method of treating an HIV infection, in a human having or at risk of having the infection by administering to the human a therapeutically effective amount of a compound of Formula (I), or a pharmaceutically acceptable salt thereof.

In a further aspect there is provided a method of treating an AIDS infection, in a human having the infection by administering to the human a therapeutically effective amount of a compound of Formula (I), or a pharmaceutically acceptable salt thereof.

In a further aspect there is provided a method of treating an HIV infection in a human by administering to the human a therapeutically effective amount of a compound of Formula (I), or a pharmaceutically acceptable salt thereof.

DETAILED DESCRIPTION OF THE INVENTION

Figure 1:
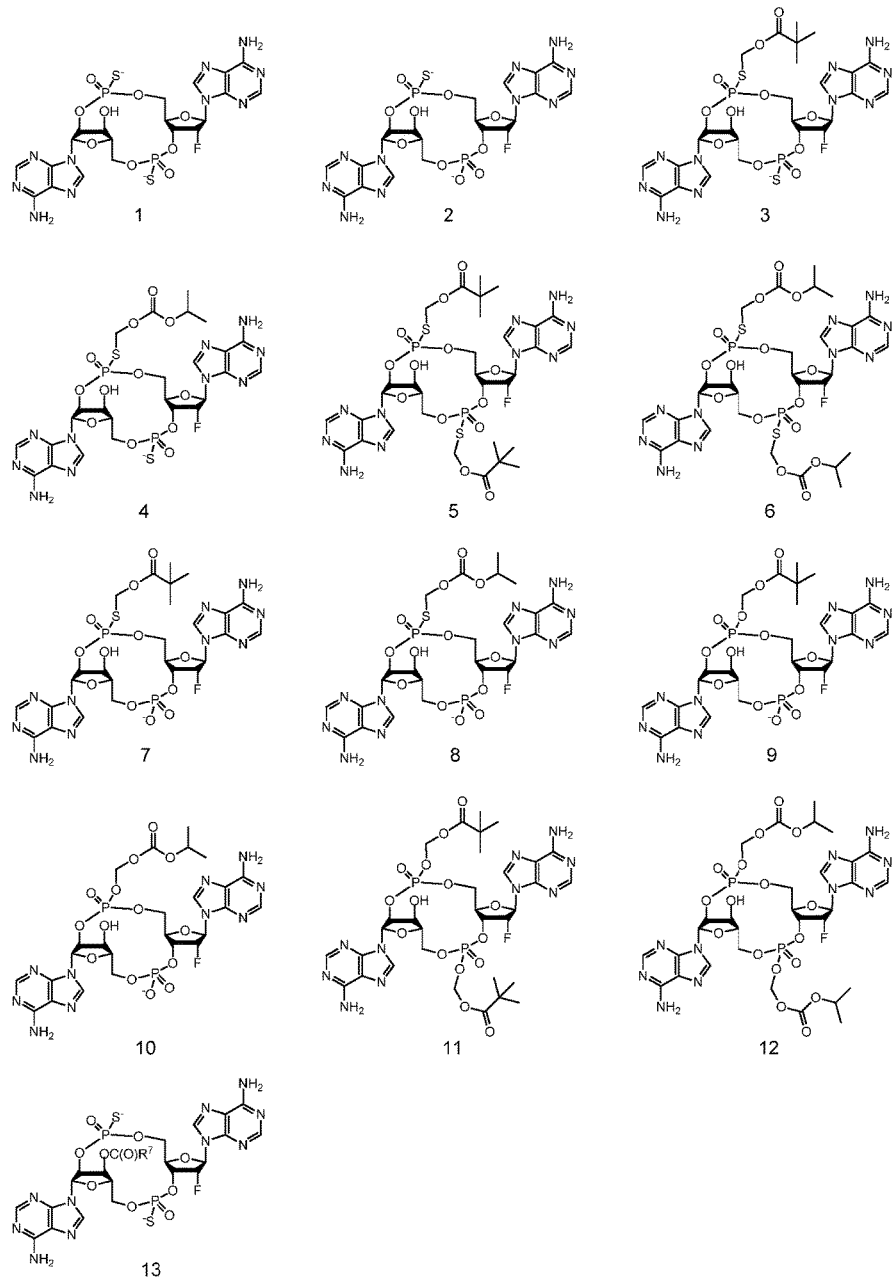
FIG. 1 depicts the structures of Compounds 1 to 13, where $R^7$ is as defined in Formula (I).
Figure 2:
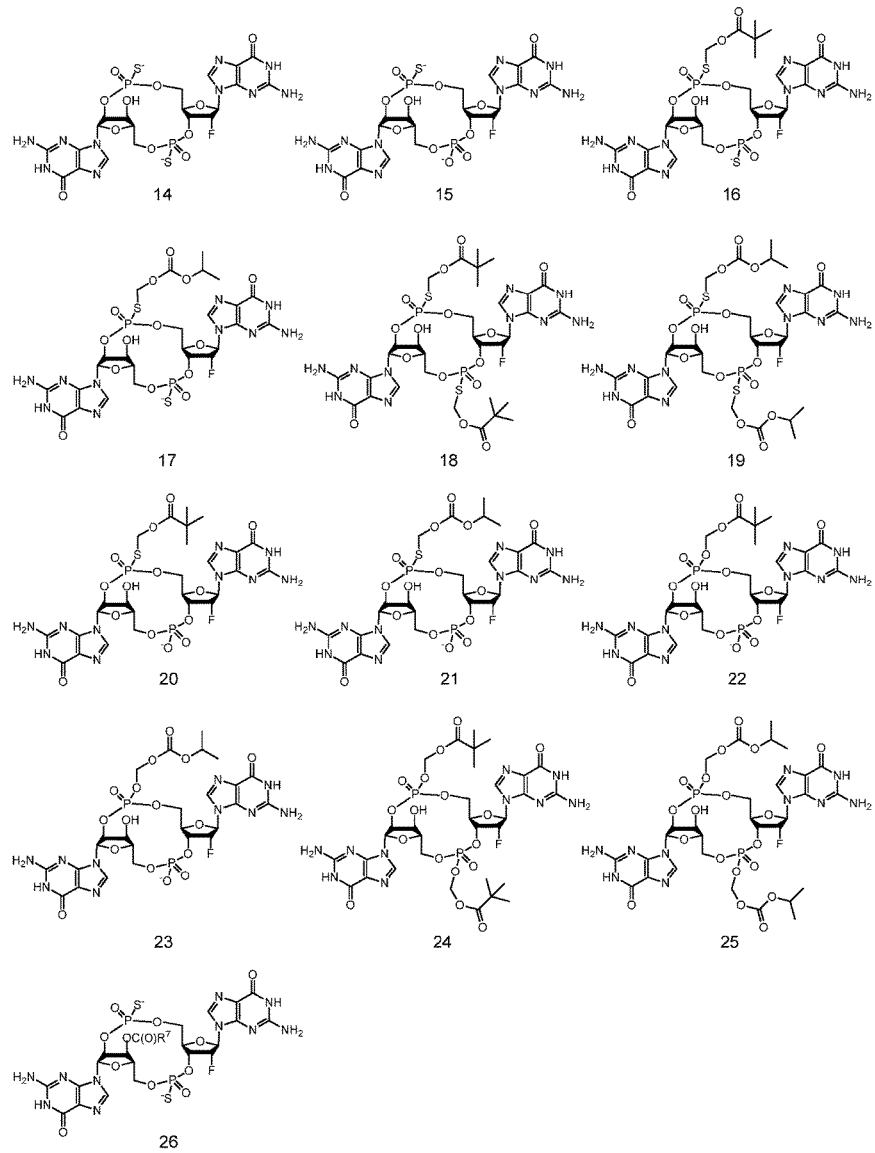
FIG. 2 depicts the structures of Compounds 14 to 26, where $R^7$ is as defined in Formula (I).
Figure 3:
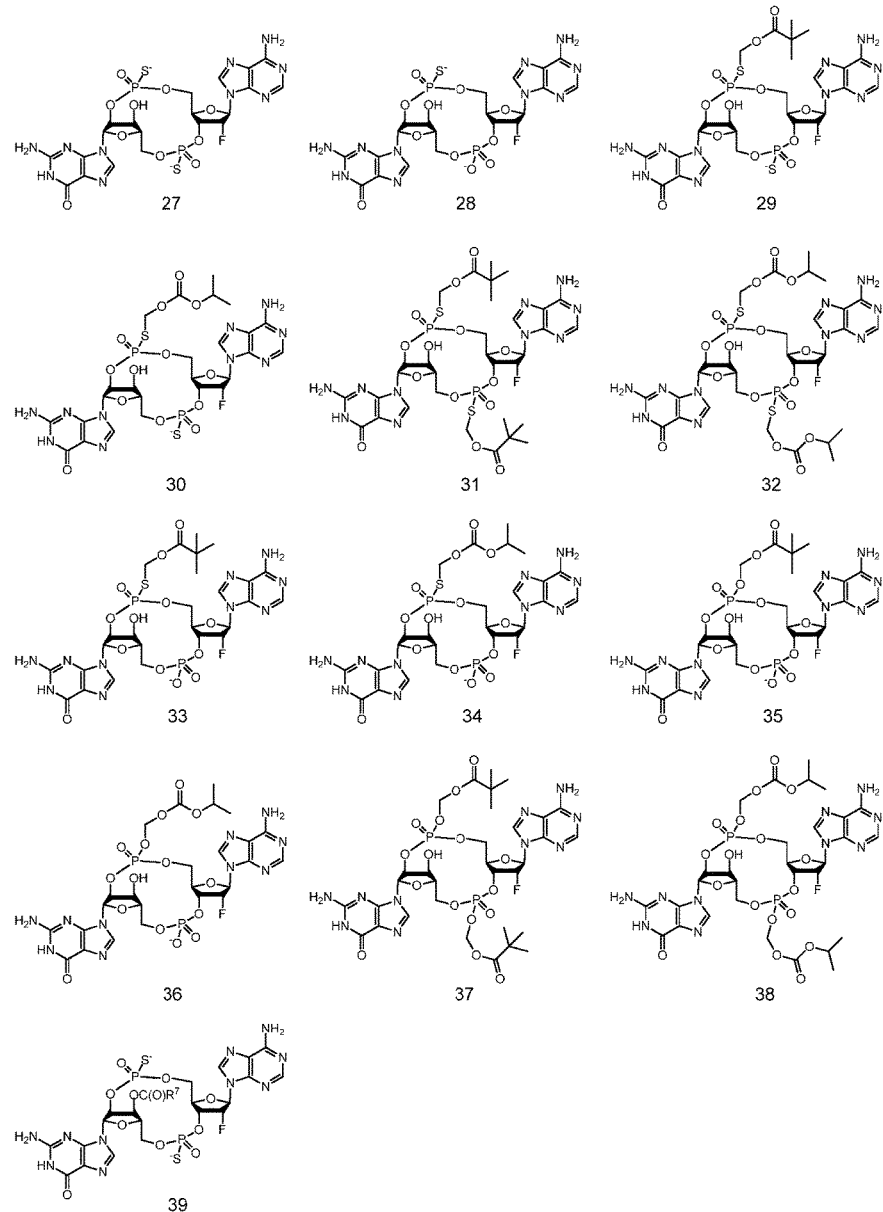
FIG. 3 depicts the structures of Compounds 27 to 39, where $R^7$ is as defined in Formula (I).
Figure 4:
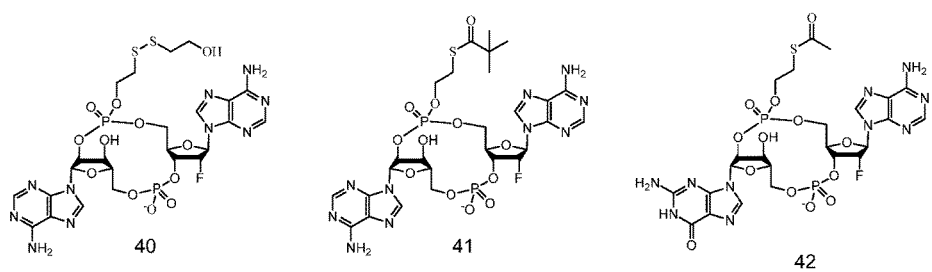
FIG. 4 depicts the structures of Compounds 40 to 42.

This invention relates to novel compounds of Formula (I):

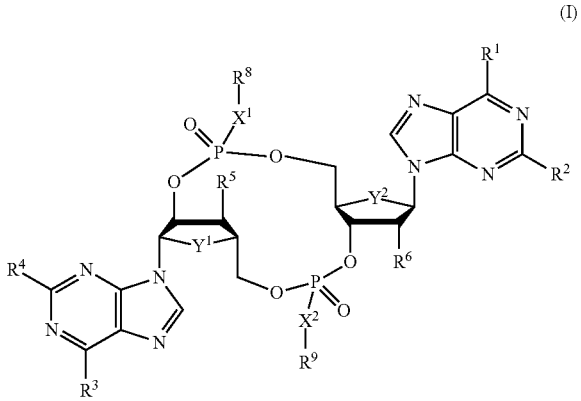

(I)

wherein:
$Y^1$ and $Y^2$ are independently $CH_2$ or O;
$X^1$ and $X^2$ are independently S or O;
$R^1$ is OH and $R^2$ is $NH_2$ or $R^1$ is $NH_2$ and $R^2$ is H;
$R^3$ is OH and $R^4$ is $NH_2$ or $R^3$ is $NH_2$ and $R^4$ is H;
$R^5$ is selected from: F, OH, and $OC(O)R^7$;
$R^6$ is selected from: F, OH, and $OC(O)R^7$;
provided: when neither $R^5$ or $R^6$ are F, at least one of $Y^1$ and $Y^2$ is $CH_2$; and $R^8$ and $R^9$ are independently selected from: H, $CH_2OC(O)R^7$, $CH_2OCO_2R^7$, $CH_2CH_2SC(O)R^7$, and $CH_2CH_2SSCH_2R^7$;
provided: when both $X^1$ and $X^2$ are O, at least one of $R^8$ and $R^9$ is not H;
where $R^7$ is selected from: aryl, heteroaryl, heterocycloalkyl, cycloalkyl, $C_{1-20}$alkyl and $C_{1-20}$alkyl substituted with one to 5 substituents independently selected from: aryl, cycloalkyl, hydroxy and F;
and pharmaceutically acceptable salts thereof.

Suitably in the compounds of Formula (I), at least one of $Y^1$ and $Y^2$ is O. Suitably in the compounds of Formula (I), both $Y^1$ and $Y^2$ are O.

Suitably in the compounds of Formula (I), at least one of $X^1$ and $X^2$ is S. Suitably in the compounds of Formula (I), $X^1$ is S. Suitably in the compounds of Formula (I), both $X^1$ and $X^2$ are S.

Suitably in the compounds of Formula (I), $R^1$ is $NH_2$ and $R^2$ is H.

Suitably in the compounds of Formula (I), $R^5$ is OH.
Suitably in the compounds of Formula (I), $R^6$ is F.
Suitably in the compounds of Formula (I), when one of $R^8$ and $R^9$ is not H, it is $CH_2CH_2SC(O)C_{1-6}$alkyl.
Suitably in the compounds of Formula (I), when one of $R^8$ and $R^9$ is not H, it is $CH_2CH_2SSC_{1-4}$alkylOH.
Suitably in the compounds of Formula (I), when $X^1$ is S, $R^8$ and $R^9$ are H.
Suitably in the compounds of Formula (I), when $X^2$ is S, $R^8$ and $R^9$ are H.
Suitably in the compounds of Formula (I), one of $R^8$ and $R^9$ is H.
Suitably in the compounds of Formula (I), when $X^1$ and $X^2$ are O, one of $R^8$ and $R^9$ is H.
Suitably in the compounds of Formula (I), $R^7$ is $C_{12-18}$alkyl.

Suitably in the compounds of Formula (I), $R^7$ is selected from: $C_{1-20}$alkyl and $C_{1-20}$alkyl substituted with one to 5 substituents independently selected from: aryl, cycloalkyl and F.
Suitably in the compounds of Formula (I), $R^7$ is $C_{1-20}$alkyl.
Suitably in the compounds of Formula (I), $R^7$ is tert-butyl.
Suitably in the compounds of Formula (I), $R^7$ is iso-propyl.

Examples of compounds of the present invention include the compounds depicted in FIGS. 1, 2, 3 and 4.

The compounds of Formula (I) may be in the form of a salt.

Included in the compounds of Formula (I) are compounds of Formula (II):

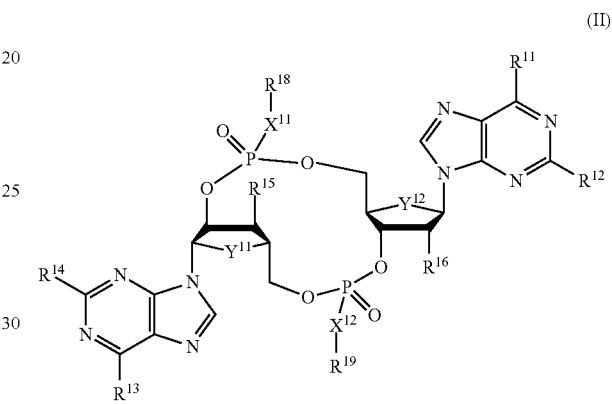

(II)

wherein:
$Y^{11}$ and $Y^{12}$ are independently $CH_2$ or O;
$X^{11}$ is S;
$X^{12}$ is O;
$R^{11}$ is OH and $R^{12}$ is $NH_2$ or $R^{11}$ is $NH_2$ and $R^{12}$ is H;
$R^{13}$ is OH and $R^{14}$ is $NH_2$ or $R^{13}$ is $NH_2$ and $R^{14}$ is H;
$R^{15}$ is selected from: F, OH, and $OC(O)R^{17}$;
$R^{16}$ is selected from: F, OH, and $OC(O)R^{17}$;
provided: when neither $R^{15}$ or $R^{16}$ are F, at least one of $Y^{11}$ and $Y^{12}$ is $CH_2$; and
$R^{18}$ and $R^{19}$ are independently selected from: H, $CH_2OC(O)R^{17}$, $CH_2OCO_2R^7$, $CH_2CH_2SC(O)R^{17}$, and $CH_2CH_2SSCH_2R^{17}$;
where $R^{17}$ is selected from: aryl, heteroaryl, heterocycloalkyl, cycloalkyl, $C_{1-20}$alkyl and $C_{1-20}$alkyl substituted with one to 5 substituents independently selected from: aryl, cycloalkyl, hydroxy and F;
and pharmaceutically acceptable salts thereof.

Suitably in the compounds of Formula (II), at least one of $Y^{11}$ and $Y^{12}$ is O. Suitably in the compounds of Formula (I), both $Y^{11}$ and $Y^{12}$ are O.

Suitably in the compounds of Formula (II), $R^{11}$ is $NH_2$ and $R^{12}$ is H.

Suitably in the compounds of Formula (II), $R^{15}$ is OH.
Suitably in the compounds of Formula (II), $R^{16}$ is F.
Suitably in the compounds of Formula (II), when one of $R^{18}$ and $R^{19}$ is not H, it is $CH_2CH_2SC(O)C_{1-6}$alkyl.
Suitably in the compounds of Formula (II), when one of $R^{18}$ and $R^{19}$ is not H, it is $CH_2CH_2SSC_{1-4}$alkylOH.
Suitably in the compounds of Formula (II), $R^{18}$ and $R^{19}$ are H.
Suitably in the compounds of Formula (II), one of $R^{18}$ and $R^{19}$ is H.

Suitably in the compounds of Formula (II), $R^{17}$ is $C_{12-18}$ alkyl.

Suitably in the compounds of Formula (II), $R^{17}$ is selected from: $C_{1-20}$alkyl and $C_{1-20}$alkyl substituted with one to 5 substituents independently selected from: aryl, cycloalkyl and F.

Suitably in the compounds of Formula (II), $R^{17}$ is $C_{1-20}$alkyl.

Suitably in the compounds of Formula (II), $R^{17}$ is tert-butyl.

Suitably in the compounds of Formula (II), $R^{17}$ is iso-propyl.

Suitably the compounds of Formula (II) are in the form of a pharmaceutically acceptable salt.

Included in the compounds of Formula (I) are compounds of Formula (III):

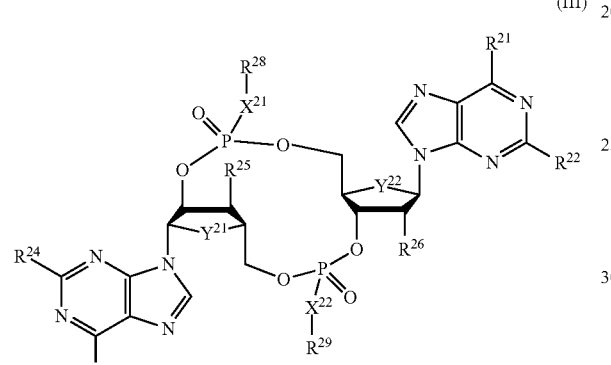

(III)

wherein:
$Y^{21}$ and $Y^{22}$ are independently $CH_2$ or O;
$X^{21}$ is O;
$X^{22}$ is S;
$R^{21}$ is OH and $R^{22}$ is $NH_2$ or $R^{21}$ is $NH_2$ and $R^{22}$ is H;
$R^{23}$ is OH and $R^{24}$ is $NH_2$ or $R^{23}$ is $NH_2$ and $R^{24}$ is H;
$R^{25}$ is selected from: F, OH, and $OC(O)R^{27}$;
$R^{26}$ is selected from: F, OH, and $OC(O)R^{27}$;
provided: when neither $R^{25}$ or $R^{26}$ are F, at least one of $Y^{21}$ and $Y^{22}$ is $CH_2$; and
$R^{28}$ and $R^{29}$ are independently selected from: H, $CH_2OC(O)R^{27}$, $CH_2OCO_2R^{27}$, $CH_2CH_2SC(O)R^{27}$, and $CH_2CH_2SSCH_2R^{27}$;
where $R^{27}$ is selected from: aryl, heteroaryl, heterocycloalkyl, cycloalkyl, $C_{1-20}$alkyl and $C_{1-20}$alkyl substituted with one to 5 substituents independently selected from: aryl, cycloalkyl, hydroxy and F;
and pharmaceutically acceptable salts thereof.

Suitably in the compounds of Formula (III), at least one of $Y^{21}$ and $Y^{22}$ is O. Suitably in the compounds of Formula (III), both $Y^{21}$ and $Y^{22}$ are O.

Suitably in the compounds of Formula (III), $R^{21}$ is $NH_2$ and $R^{22}$ is H.

Suitably in the compounds of Formula (III), $R^{25}$ is OH.

Suitably in the compounds of Formula (III), $R^{26}$ is F.

Suitably in the compounds of Formula (III), when one of $R^{28}$ and $R^{29}$ is not H, it is $CH_2CH_2SC(O)C_{1-6}$alkyl.

Suitably in the compounds of Formula (III), when one of $R^{28}$ and $R^{29}$ is not H, it is $CH_2CH_2SSC_{1-4}$alkylOH.

Suitably in the compounds of Formula (III), $R^{28}$ and $R^{29}$ are H.

Suitably in the compounds of Formula (III), one of $R^{28}$ and $R^{29}$ is H.

Suitably in the compounds of Formula (III), $R^{27}$ is $C_{12-18}$ alkyl.

Suitably in the compounds of Formula (III), $R^{27}$ is selected from: $C_{1-20}$alkyl and $C_{1-20}$alkyl substituted with one to 5 substituents independently selected from: aryl, cycloalkyl and F.

Suitably in the compounds of Formula (III), $R^{27}$ is $C_{1-20}$alkyl.

Suitably in the compounds of Formula (III), $R^{27}$ is tert-butyl.

Suitably in the compounds of Formula (III), $R^{27}$ is iso-propyl.

Suitably the compounds of Formula (III) are in the form of a pharmaceutically acceptable salt.

Included in the compounds of Formula (I) and the compounds of Formula (II) are compounds of Formula (IV):

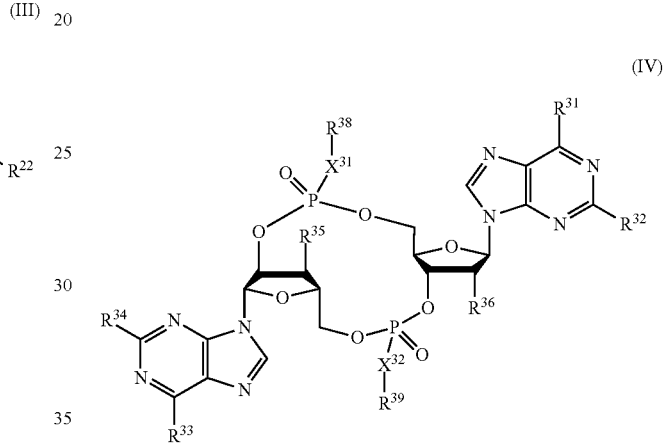

(IV)

wherein:
$X^{31}$ is S;
$X^{32}$ is O;
$R^{31}$ is OH and $R^{32}$ is $NH_2$ or $R^{31}$ is $NH_2$ and $R^{32}$ is H;
$R^{33}$ is OH and $R^{34}$ is $NH_2$ or $R^{33}$ is $NH_2$ and $R^{34}$ is H;
$R^{35}$ is selected from: F, OH, and $OC(O)R^{37}$;
$R^{36}$ is selected from: F, OH, and $OC(O)R^{37}$;
provided: at least one of $R^{35}$ and $R^{36}$ is F; and
$R^{38}$ and $R^{39}$ are independently selected from: H, $CH_2OC(O)R^{37}$, $CH_2OCO_2R^{37}$, $CH_2CH_2SC(O)R^{37}$, and $CH_2CH_2SSCH_2R^{37}$;
where $R^{37}$ is selected from: aryl, heteroaryl, heterocycloalkyl, cycloalkyl, $C_{1-20}$alkyl and $C_{1-20}$alkyl substituted with one to 5 substituents independently selected from: aryl, cycloalkyl, hydroxy and F;
and pharmaceutically acceptable salts thereof.

Suitably in the compounds of Formula (IV), $R^{31}$ is $NH_2$ and $R^{32}$ is H.

Suitably in the compounds of Formula (IV), $R^{35}$ is OH.

Suitably in the compounds of Formula (IV), $R^{36}$ is F.

Suitably in the compounds of Formula (IV), when one of $R^{38}$ and $R^{39}$ is not H, it is $CH_2CH_2SC(O)C_{1-6}$alkyl.

Suitably in the compounds of Formula (IV), when one of $R^{38}$ and $R^{39}$ is not H, it is $CH_2CH_2SSC_{1-4}$alkylOH.

Suitably in the compounds of Formula (IV), $R^{38}$ and $R^{39}$ are H.

Suitably in the compounds of Formula (IV), one of $R^{38}$ and $R^{39}$ is H.

Suitably in the compounds of Formula (IV), $R^{37}$ is $C_{12-18}$ alkyl.

Suitably in the compounds of Formula (IV), $R^{37}$ is selected from: $C_{1-20}$alkyl and $C_{1-20}$alkyl substituted with one to 5 substituents independently selected from: aryl, cycloalkyl and F.

Suitably in the compounds of Formula (IV), $R^{37}$ is $C_{1-20}$alkyl.

Suitably in the compounds of Formula (IV), $R^{37}$ is tert-butyl.

Suitably in the compounds of Formula (IV), $R^{37}$ is iso-propyl.

Suitably the compounds of Formula (IV) are in the form of a pharmaceutically acceptable salt.

Included in the compounds of Formula (I) and the compounds of Formula (III) are compounds of Formula (V):

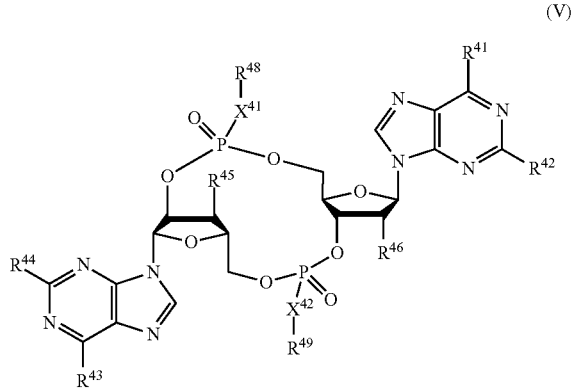

(V)

wherein:
$X^{41}$ is O;
$X^{42}$ is S;
$R^{41}$ is OH and $R^{42}$ is $NH_2$ or $R^{41}$ is $NH_2$ and $R^{42}$ is H;
$R^{43}$ is OH and $R^{44}$ is $NH_2$ or $R^{43}$ is $NH_2$ and $R^{44}$ is H;
$R^{45}$ is selected from: F, OH, and $OC(O)R^{47}$;
$R^{46}$ is selected from: F, OH, and $OC(O)R^{47}$;
provided: at least one of $R^{45}$ and $R^{46}$ is F; and
$R^{48}$ and $R^{49}$ are independently selected from: H, $CH_2OC(O)R^{47}$, $CH_2OCO_2R^{47}$, $CH_2CH_2SC(O)R^{47}$, and $CH_2CH_2SSCH_2R^{47}$;
where $R^{47}$ is selected from: aryl, heteroaryl, heterocycloalkyl, cycloalkyl, $C_{1-20}$alkyl and $C_{1-20}$alkyl substituted with one to 5 substituents independently selected from: aryl, cycloalkyl, hydroxy and F;
and pharmaceutically acceptable salts thereof.

Suitably in the compounds of Formula (V), $R^{41}$ is $NH_2$ and $R^{42}$ is H.

Suitably in the compounds of Formula (V), $R^{45}$ is OH.

Suitably in the compounds of Formula (V), $R^{46}$ is F.

Suitably in the compounds of Formula (V), when one of $R^{48}$ and $R^{49}$ is not H, it is $CH_2CH_2SC(O)C_{1-6}$alkyl.

Suitably in the compounds of Formula (V), when one of $R^{48}$ and $R^{49}$ is not H, it is $CH_2CH_2SSC_{1-4}$alkylOH.

Suitably in the compounds of Formula (V), $R^{48}$ and $R^{49}$ are H.

Suitably in the compounds of Formula (V), one of $R^{48}$ and $R^{49}$ is H.

Suitably in the compounds of Formula (V), $R^{47}$ is $C_{12-18}$alkyl.

Suitably in the compounds of Formula (V), $R^{47}$ is selected from: $C_{1-20}$alkyl and $C_{1-20}$alkyl substituted with one to 5 substituents independently selected from: aryl, cycloalkyl and F.

Suitably in the compounds of Formula (V), $R^{47}$ is $C_{1-20}$alkyl.

Suitably in the compounds of Formula (V), $R^{47}$ is tert-butyl.

Suitably in the compounds of Formula (V), $R^{47}$ is iso-propyl.

Suitably the compounds of Formula (V) are in the form of a pharmaceutically acceptable salt.

Included in the compounds of Formula (I) are compounds of Formula (VI):

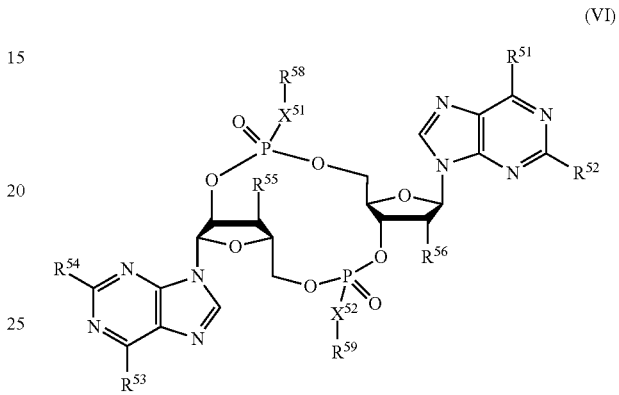

(VI)

wherein:
$X^{51}$ is O;
$X^{52}$ is O;
$R^{51}$ is OH and $R^{52}$ is $NH_2$ or $R^{51}$ is $NH_2$ and $R^{52}$ is H;
$R^{53}$ is OH and $R^{54}$ is $NH_2$ or $R^{53}$ is $NH_2$ and $R^{54}$ is H;
$R^{55}$ is selected from: F, OH, and $OC(O)R^{47}$;
$R^{56}$ is F;
$R^{58}$ and $R^{59}$ are independently selected from: H, $CH_2OC(O)R^{57}$, $CH_2OCO_2R^{57}$, $CH_2CH_2SC(O)R^{57}$, and $CH_2CH_2SSCH_2R^{57}$;
where $R^{57}$ is selected from: aryl, heteroaryl, heterocycloalkyl, cycloalkyl, $C_{1-20}$alkyl and $C_{1-20}$alkyl substituted with one to 5 substituents independently selected from: aryl, cycloalkyl, hydroxy and F;
provided that at least one of $R^{58}$ and $R^{59}$ is not H.
and pharmaceutically acceptable salts thereof.

Suitably in the compounds of Formula (VI), $R^{51}$ is $NH_2$ and $R^{52}$ is H.

Suitably in the compounds of Formula (VI), $R^{55}$ is OH.

Suitably in the compounds of Formula (VI), when one of $R^{58}$ and $R^{59}$ is not H, it is $CH_2CH_2SC(O)C_{1-6}$alkyl.

Suitably in the compounds of Formula (VI), when one of $R^{58}$ and $R^{59}$ is not H, it is $CH_2CH_2SSC_{1-4}$alkylOH.

Suitably in the compounds of Formula (VI), one of $R^{58}$ and $R^{59}$ is H.

Suitably in the compounds of Formula (VI), $R^{57}$ is $C_{12-18}$alkyl.

Suitably in the compounds of Formula (VI), $R^{57}$ is selected from: $C_{1-20}$alkyl and $C_{1-20}$alkyl substituted with one to 5 substituents independently selected from: aryl, cycloalkyl and F.

Suitably in the compounds of Formula (VI), $R^{57}$ is $C_{1-20}$alkyl.

Suitably in the compounds of Formula (VI), $R^{57}$ is tert-butyl.

Suitably in the compounds of Formula (VI), $R^{57}$ is iso-propyl.

Suitably the compounds of Formula (VI) are in the form of a pharmaceutically acceptable salt.

Included in the compounds of Formula (I) are:

(1R,6R,8R,9R,10R,15R,17R,18R)-8,17-bis(6-amino-9H-purin-9-yl)-9-fluoro-18-hydroxy-3,12-disulfanyl-2,4,7,11,13,16-hexaoxa-3λ$^5$,12λ$^5$-diphosphatricyclo[13.2.1.0$^{6,10}$]octadecane-3,12-dione;

(1R,6R,8R,9R,10R,15R,17R,18R)-8,17-bis(6-amino-9H-purin-9-yl)-9-fluoro-18-hydroxy-3,12-disulfanyl-2,4,7,11,13,16-hexaoxa-3λ$^5$,12λ$^5$-diphosphatricyclo[13.2.1.0$^{6,10}$]octadecane-3,12-dione, isomer 1;

(1R,6R,8R,9R,10R,15R,17R,18R)-8,17-bis(6-amino-9H-purin-9-yl)-9-fluoro-18-hydroxy-3,12-disulfanyl-2,4,7,11,13,16-hexaoxa-3λ$^5$,12λ$^5$-diphosphatricyclo[13.2.1.0$^{6,10}$]octadecane-3,12-dione, isomer 2;

(1R,6R,8R,9R,10R,15R,17R,18R)-8,17-bis(6-amino-9H-purin-9-yl)-9-fluoro-12,18-dihydroxy-3-sulfanyl-2,4,7,11,13,16-hexaoxa-3λ$^5$,12λ$^5$-diphosphatricyclo[13.2.1.0$^{6,10}$]octadecane-3,12-dione;

(1R,6R,8R,9R,10R,15R,17R,18R)-8,17-bis(6-amino-9H-purin-9-yl)-9-fluoro-12,18-dihydroxy-3-sulfanyl-2,4,7,11,13,16-hexaoxa-3λ$^5$,12λ$^5$-diphosphatricyclo[13.2.1.0$^{6,10}$]octadecane-3,12-dione, isomer 1;

(1R,6R,8R,9R,10R,15R,17R,18R)-8,17-bis(6-amino-9H-purin-9-yl)-9-fluoro-12,18-dihydroxy-3-sulfanyl-2,4,7,11,13,16-hexaoxa-3λ$^5$,12λ$^5$-diphosphatricyclo[13.2.1.0$^{6,10}$]octadecane-3,12-dione, isomer 2;

(1R,6R,8R,9R,10R,15R,17R,18R)-17-(2-amino-6-oxo-6,9-dihydro-1H-purin-9-yl)-8-(6-amino-9H-purin-9-yl)-9-fluoro-12,18-dihydroxy-3-sulfanyl-2,4,7,11,13,16-hexaoxa-3λ$^5$,12λ$^5$-diphosphatricyclo[13.2.1.0$^{6,10}$]octadecane-3,12-dione;

(1R,6R,8R,9R,10R,15R,17R,18R)-17-(2-amino-6-oxo-6,9-dihydro-1H-purin-9-yl)-8-(6-amino-9H-purin-9-yl)-9-fluoro-12,18-dihydroxy-3-sulfanyl-2,4,7,11,13,16-hexaoxa-3λ$^5$,12λ$^5$-diphosphatricyclo[13.2.1.0$^{6,10}$]octadecane-3,12-dione, isomer 1;

(1R,6R,8R,9R,10R,15R,17R,18R)-17-(2-amino-6-oxo-6,9-dihydro-1H-purin-9-yl)-8-(6-amino-9H-purin-9-yl)-9-fluoro-12,18-dihydroxy-3-sulfanyl-2,4,7,11,13,16-hexaoxa-3λ$^5$,12λ$^5$-diphosphatricyclo[13.2.1.0$^{6,10}$]octadecane-3,12-dione, isomer 2;

(1R,6R,8R,9R,10R,15R,17R,18R)-17-(2-amino-6-oxo-6,9-dihydro-1H-purin-9-yl)-8-(6-amino-9H-purin-9-yl)-9-fluoro-18-hydroxy-3,12-disulfanyl-2,4,7,11,13,16-hexaoxa-3λ$^5$,12λ$^5$-diphosphatricyclo[13.2.1.0$^{6,10}$]octadecane-3,12-dione;

(1R,6R,8R,9R,10R,15R,17R,18R)-17-(2-amino-6-oxo-6,9-dihydro-1H-purin-9-yl)-8-(6-amino-9H-purin-9-yl)-9-fluoro-18-hydroxy-3,12-disulfanyl-2,4,7,11,13,16-hexaoxa-3λ$^5$,12λ$^5$-diphosphatricyclo[13.2.1.0$^{6,10}$]octadecane-3,12-dione, isomer 1; and (1R,6R,8R,9R,10R,15R,17R,18R)-17-(2-amino-6-oxo-6,9-dihydro-1H-purin-9-yl)-8-(6-amino-9H-purin-9-yl)-9-fluoro-18-hydroxy-3,12-disulfanyl-2,4,7,11,13,16-hexaoxa-3λ$^5$,12λ$^5$-diphosphatricyclo[13.2.1.0$^{6,10}$]octadecane-3,12-dione, isomer 2;

and pharmaceutically acceptable salts thereof.

It will be appreciated that Compound 2 is mixture of isomers as indicated below.

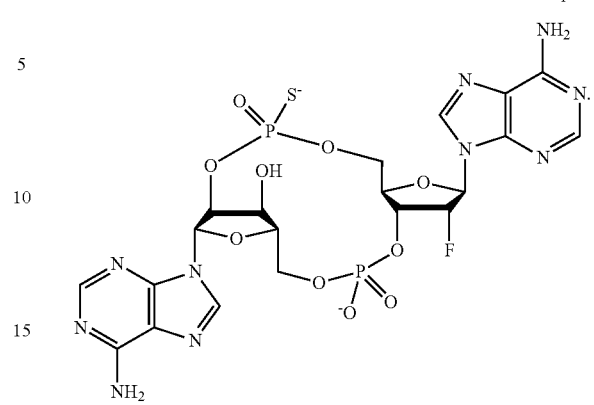

Compound 2

Isomers of Compound 2 are:

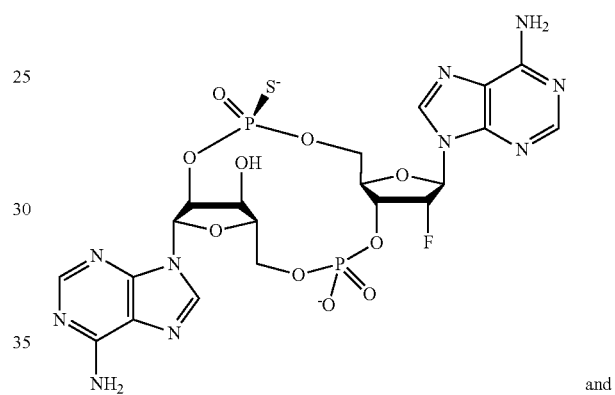

and

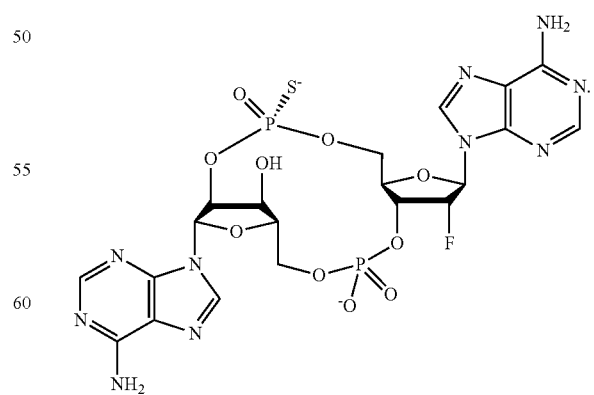

It will be appreciated that Compound 28 is mixture of isomers as indicated below.

Compound 28

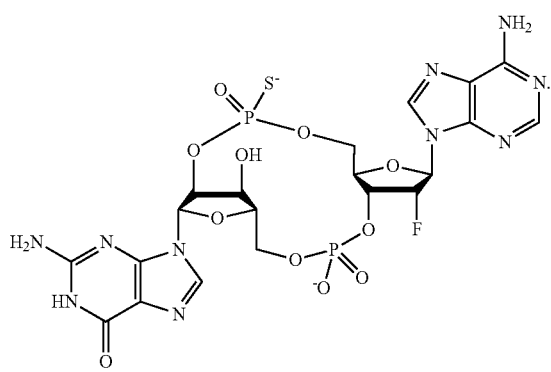

Isomers of Compound 28 are:

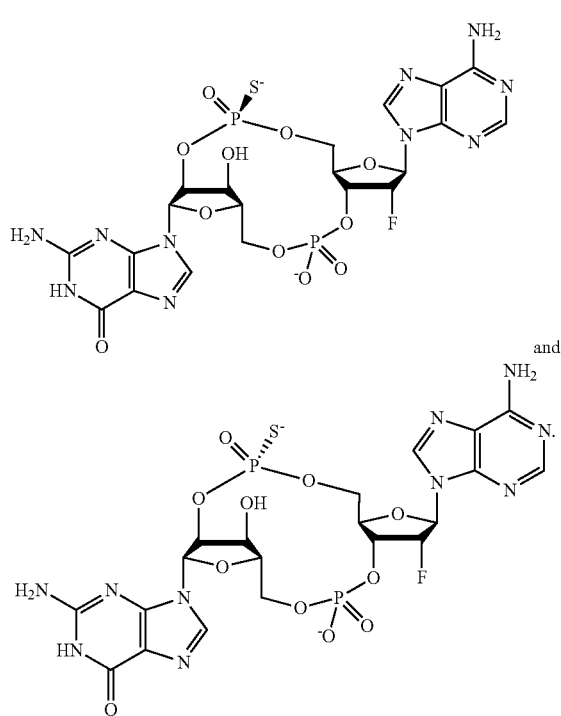

It will be appreciated that compounds depicted, for example, by the structure:

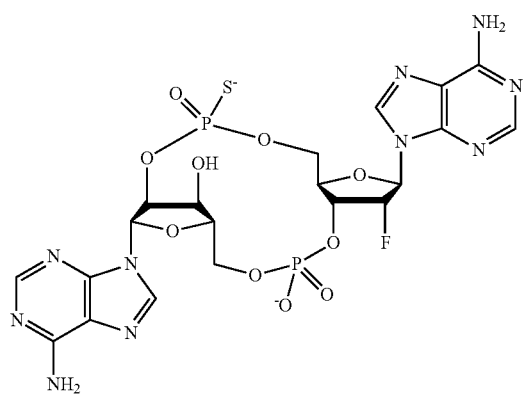

also exist in a protonated form, such as:

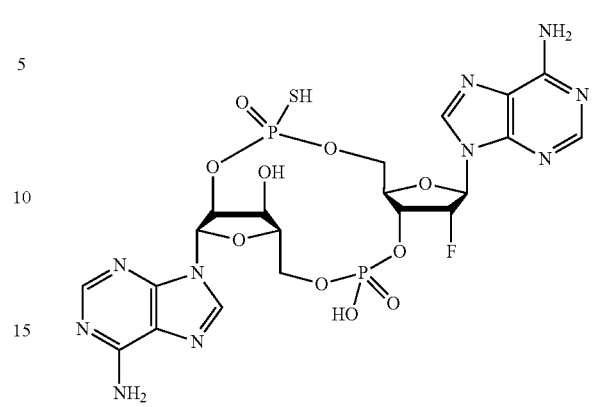

which represents the same compound.

It will be appreciated that compounds depicted, for example, by the structure:

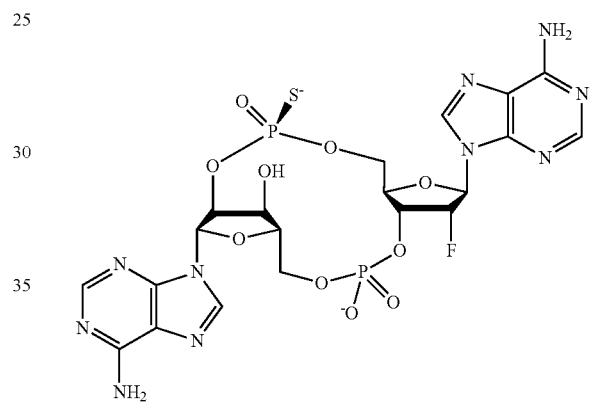

also exist in a protonated form, such as:

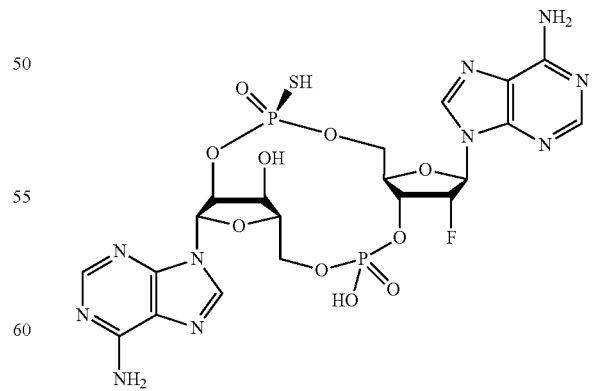

which represents the same compound.

It will be appreciated that compounds depicted, for

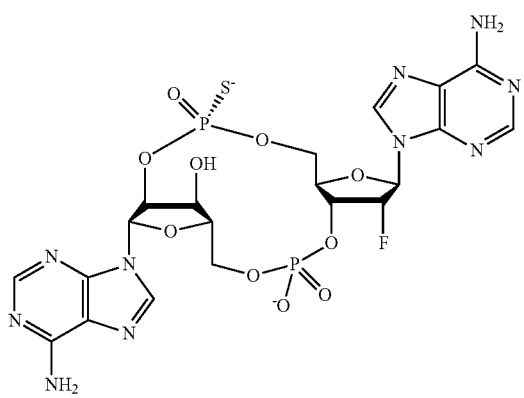

also exist in a protonated form, such as:

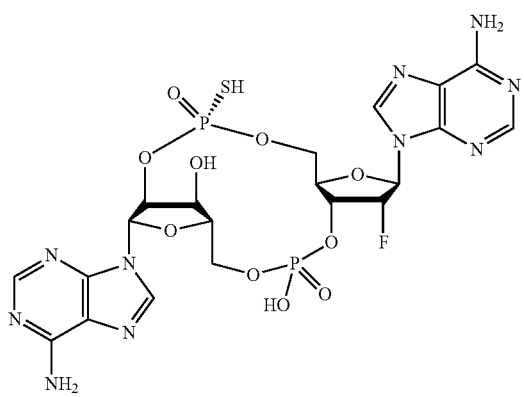

which represents the same compound.

Typically, the salts of the present invention are pharmaceutically acceptable salts. Salts encompassed within the term "pharmaceutically acceptable salts" refer to non-toxic salts of the compounds of this invention.

Salts, including pharmaceutically acceptable salts, are readily prepared by those of skill in the art.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicylate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl) amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

The invention includes within its scope all possible stoichiometric and non-stoichiometric forms of the compounds of Formula (I).

The compounds of the invention may exist in solid or liquid form. In solid form, compound of the invention may exist in a continuum of solid states ranging from fully amorphous to fully crystalline. The term 'amorphous' refers to a state in which the material lacks long range order at the molecular level and, depending upon the temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the invention may have the ability to crystallize in more than one form, a characteristic, which is known as polymorphism ("polymorphs"). Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of Formula (I) may exist in solvated and unsolvated forms. As used herein, the term "solvate" refers to a complex of variable stoichiometry formed by a solute (in this invention, a compound of Formula (I) or a salt) and a solvent. Such solvents, for the purpose of the invention, may not interfere with the biological activity of the solute. The skilled artisan will appreciate that pharmaceutically acceptable solvates may be formed for crystalline compounds wherein solvent molecules are incorporated into the crystalline lattice during crystallization. The incorporated solvent molecules may be water molecules or non-aqueous such as ethanol, isopropanol, DMSO, acetic acid, ethanolamine, and ethyl acetate molecules. Crystalline lattice incorporated with water molecules are typically referred to as "hydrates". Hydrates include stoichiometric hydrates as well as compositions containing variable amounts of water.

It is also noted that the compounds of Formula (I) may form tautomers. 'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. It is understood that all tautomers and mixtures of tautomers of the compounds of the present invention are included within the scope of the compounds of the present invention. For example and for absolute clarity, in the compounds of Formula (I) when $R^1$ or $R^3$ represent OH, the compounds will form the keto tautomer (=O).

While aspects for each variable have generally been listed above separately for each variable this invention includes those compounds in which several or each aspect in Formula (I) is selected from each of the aspects listed above. Therefore, this invention is intended to include all combinations of aspects for each variable.

Native CDN molecules can be sensitive to degradation by phosphodiesterases that are present in the blood, on the surface of host cell or in the host cells, for example in antigen presenting cells, that take up vaccine formulations that contain said native CDN molecules. Specific examples are the ectonucleotidiases, such as CD39, CD73 and ENPP1 that reside on cell plasma membrane, facing into plasma, many of which are known to degrade nucleotides, for example ATP is converted to AMP by both CD39 and ENPP1. Recently ENPP1 has been identified as a major contributor to the degradation of CDNs possessing a 2'-5' phosphodiester linkage (Li, L., et al., 2014, Nature Chemical Biology, 10(12), p 1043-1048). The potency of a CDN possessing STING agonist activity would be diminished by such degradation, resulting in lower amount of induced expression of a signature molecule of innate immunity (e.g., IFN-beta) and hence afford weaker adjuvant potency. The present invention describes two different and complementary approaches that can be employed to enhance and maintain the potency of described novel CDNs. As described in more detail in the following sections these are the substitution of sulphur for oxygen in the non-bridging positions of the phosphodiester and the use of a prodrug strategy to enhance cell penetration and protect the CDN from degradation.

One aspect of the present invention relates to stereochemically defined diasteroemers of cyclic purine mono- and dithio-diphosphate dinucleotides which induce STING-dependent TBK1 activation and their methods of preparation and use.

The present invention relates to methods for providing a potent STING agonist capable of priming and maintaining a T cell response to tumor antigens either alone or in combination with other immuno-oncology agents and to methods for providing adjuvant compositions. These compositions are comprised of one or more cyclic purine dinucleotides of Formula (I), wherein the cyclic purine dinucleotides present in the composition are substantially pure single mono-thiophosphate diasteromers or di-thiophosphate diastereomers, methods for the manufacture thereof, and methods for the use thereof to stimulate an immune response in an animal. The goal of both the single agent and vaccine formulation is to provide a combination of antigens and adjuvants capable of generating a sufficient population of memory T cells and/or B cells to react quickly to a pathogen, tumor cell, etc., bearing an antigen of interest.

Thiophosphates (also referred to as phosphorothioates) are a variant of normal nucleotides in which one of the nonbridging oxygens attached to phosphorus is replaced by a sulfur. A phosphorothioate linkage is inherently chiral. The skilled artisan will recognize that the thiophosphates in this structure may each exist in R or S form. Thus, Rp, and Sp, forms are possible at each phosphorus atom. In each case, preferred are substantially pure diastereomers of these molecules. Examples of such CDN thiophosphate molecules are depicted in FIGS. 1 to 4 herein.

The term "prodrug" as used herein refers to a modification of contemplated compounds, wherein the modified compound is converted within the body (e.g., in a target cell or target organ) back into the unmodified form through enzymatic or non-enzymatic reactions. In many cases the prodrug form is inactive or substantially less active than the parent non-prodrug form of the contemplated compounds. In certain embodiments, the hydroxyl on one ribose comprises a prodrug leaving group (Compounds 13, 26 and 39). In other embodiments the prodrug form involves derivatization of either one or both of the phosphates and/or thiophosphates (Compounds 3-12, 16-25 and 29-38). Prodrugs can modify the physicochemical, biopharmaceutic, and pharmacokinetic properties of drugs. Reasons for prodrug development are typically poor aqueous solubility, chemical instability, low oral bioavailability, lack of blood brain barrier penetration, and high first pass metabolism associated with the parent drug. Suitable prodrug moieties are described in, for example, "Prodrugs and Targeted Delivery," J. Rautico, Ed., John Wiley & Sons, 2011. Prodrugs of phosphates which are of particular relevance to the current invention are described by Wiemer, A. J., and Wiemer, D. F. "Prodrugs of Phosphonates and Phosphates: Crossing the Membrane Barrier" in Topics of Current Chemistry, (2015) V 360, 115-160.

Preferred cyclic purine dinucleotides of the present invention include the prodrugs di-phosphate CDNs (such as, Compounds 9, 10, 11 and 12 of FIG. 1; Compounds 22, 23, 24 and 25 of FIG. 2; Compounds 35, 36, 37 and 38 of FIG. 3 and Compounds 40, 41 and 42 of FIG. 4) the non-prodrug monothiophospates (such as, Compounds 2, 15 and 28 of FIGS. 1-3) and non-prodrug dithiophosphates (such as Compounds 1, 14 and 27 of FIGS. 1-3) and prodrug forms of both the mono- (such as Compounds 7, 8, 20, 21, 33 and 34 of FIGS. 1-3) and di-thiophosphate (such as Compounds 3-6, 16-19, and 29-32 of FIGS. 1 to 3).

Definitions

As used herein, "a compound of the invention" includes all solvates, complexes, polymorphs, radiolabeled derivatives, tautomers, stereoisomers and optical isomers of the compounds of Formula (I) and salts thereof.

As used herein, specific Compounds of the invention are designated numerically according to the indication in the Figures. For example, Compound 2 is the compound in FIG. 1 with "2" under it, and Compound 27 is the compound in FIG. 3 with "27" under it. Further "a" and "b", etc. designations correspond to Isomer 1 and Isomer 2, etc., respectively. For example, "Compound 2a" is Isomer 1 of Compound 2, "Compound 27b" is Isomer 2 of Compound 27.

Unless otherwise defined, the designation "Isomer" or "Diastereomer" is an indication of the order in which a specified compound is eluted from a separation column under the specified conditions. The specified compound with a shorter retention time on LCMS is designated "Isomer 1" or "Diastereomer 1", the specified compound with a longer retention time on LCMS is designated "Isomer 2" or "Diastereomer 2", etc.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The term "prophylaxis" includes prevention and refers to a measure or procedure which is to prevent rather than cure or treat a disease. Preventing refers to a reduction in risk of acquiring or developing a disease causing at least one clinical symptom of the disease not to develop in a subject that may be exposed to a disease causing agent or a subject predisposed to the disease in advance of disease outset.

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, "pharmaceutically acceptable excipients" includes all diluents, carriers binders, glidants and other components of pharmaceutical formulations with which the compound of the invention is administered.

"Alkyl" refers to a hydrocarbon chain having the specified number of "member atoms". For example, $C_1$-$C_6$ alkyl refers to an alkyl group having from 1 to 6 member atoms. For example, $C_{12}$-$C_{18}$alkyl refers to an alkyl group having from 12 to 18 member atoms. For example, $C_1$-$C_{20}$alkyl refers to an alkyl group having from 1 to 20 member atoms. Alkyl groups may be saturated, unsaturated, straight or branched. Representative branched alkyl groups have one, two, or three branches. Examplary alkyl includes methyl, ethyl, ethylene, propyl (n-propyl and isopropyl), butene, butyl (n-butyl, isobutyl, and t-butyl), pentyl and hexyl.

"Cycloalkyl", unless otherwise defined, refers to a saturated or unsaturated non aromatic hydrocarbon ring system having from three to seven carbon atoms. Cycloalkyl groups are monocyclic or bicyclic ring systems. For example, $C_3$-$C_7$ cycloalkyl refers to a cycloalkyl group having from 3 to 7 member atoms. Examples of cycloalkyl as used herein include: cyclopropyl, cyclobutyl, cyclopentyl, cyclohexyl, cyclobutenyl, cyclopentenyl, cyclohexenyl, cycloheptyl and spiro heptane.

"Aryl" refers to an aromatic hydrocarbon ring. Aryl groups are monocyclic, bicyclic, and tricyclic ring systems having a total of five to fourteen ring member atoms, wherein at least one ring system is aromatic and wherein each ring in the system contains 3 to 7 member atoms, such as phenyl, naphthalene, tetrahydronaphthalene and biphenyl. Suitably aryl is phenyl.

"Heteroaryl" refers to a monocyclic aromatic 4 to 8 member ring containing from 1 to 7 carbon atoms and containing from 1 to 4 heteroatoms, provided that when the number of carbon atoms is 3, the aromatic ring contains at least two heteroatoms. Heteroaryl groups containing more than one heteroatom may contain different heteroatoms. Examplary heteroaryl includes: pyrrolyl, pyrazolyl, imidazolyl, oxazolyl, isoxazolyl, thiazolyl, isothiazolyl, furanyl, furazanyl, thienyl, triazolyl, pyridinyl, pyrimidinyl, pyridazinyl, pyrazinyl, triazinyl, tetrazinyl.

"Heterocycloalkyl" refers to a saturated or unsaturated non-aromatic ring containing 4 to 12 member atoms, of which 1 to 11 are carbon atoms and from 1 to 6 are heteroatoms. Heterocycloalkyl groups containing more than one heteroatom may contain different heteroatoms. Heterocycloalkyl groups are monocyclic ring systems or a monocyclic ring fused with an aryl ring or to a heteroaryl ring having from 3 to 6 member atoms. Examplary heterocycloalkyl includes: pyrrolidinyl, tetrahydrofuranyl, dihydrofuranyl, pyranyl, tetrahydropyranyl, dihydropyranyl, tetrahydrothienyl, pyrazolidinyl, oxazolidinyl, oxetanyl, thiazolidinyl, piperidinyl, homopiperidinyl, piperazinyl, morpholinyl, thiamorpholinyl, 1,3-dioxolanyl, 1,3-dioxanyl, 1,4-dioxanyl, 1,3-oxathiolanyl, 1,3-oxathianyl, 1,3-dithianyl, 1,3oxazolidin-2-one, hexahydro-1H-azepin, 4,5,6,7, tetrahydro-1H-benzimidazol, piperidinyl, 1,2,3,6-tetrahydro-pyridinyl and azetidinyl.

"Heteroatom", unless otherwise defined, refers to a nitrogen, sulphur or oxygen atom.

Compositions

While it is possible that, for use in therapy, the compound of the invention may be administered as the raw chemical, it is possible to present the compound of the invention as the active ingredient as a pharmaceutical composition. Such compositions can be prepared in a manner well known in the pharmaceutical art and comprise at least one active compound. Accordingly, the invention further provides pharmaceutical compositions comprising a compound of the invention and one or more pharmaceutically acceptable excipients. The excipient(s) must be acceptable in the sense of being compatible with the other ingredients of the composition and not deleterious to the recipient thereof. In accordance with another aspect of the invention there is also provided a process for the preparation of a pharmaceutical composition including the agent, or pharmaceutically acceptable salts thereof, with one or more pharmaceutically acceptable excipients. The pharmaceutical composition can be for use in the treatment and/or prophylaxis of any of the conditions described herein.

Generally, the compound of the invention is administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

Pharmaceutical compositions may be presented in unit dose forms containing a predetermined amount of active ingredient per unit dose. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions.

Preferred unit dosage compositions are those containing a daily dose or sub-dose, or an appropriate fraction thereof, of an active ingredient. Such unit doses may therefore be administered once or more than once a day. Such pharmaceutical compositions may be prepared by any of the methods well known in the pharmacy art.

Pharmaceutical compositions may be adapted for administration by any appropriate route, for example by the oral (including buccal or sublingual), rectal, inhaled, intranasal, topical (including buccal, sublingual or transdermal), vaginal or injectable (including subcutaneous, intramuscular, parenteral, intravenous or intradermal) route. Such compositions may be prepared by any method known in the art of pharmacy, for example by bringing into association the active ingredient with the carrier(s) or excipient(s).

In addition to the above described routes of administration for the treatment of cancer, the pharmaceutical compositions may be adapted for administration by intratumoral or peritumoral injection. The intratumoral or peritumoral injection of a compound of the present invention directly into or adjacent to a single solid tumor is expected to elicit an immune response that can attack and destroy cancer cells throughout the body, substantially reducing and in some cases permanently eliminating the tumor from the diseased subject. The activation of the immune system in this manner to kill tumors at a remote site is commonly known as the abscopal effect and has been demonstrated in animals with multiple therapeutic modalities, (van der Jeught, et al., *Oncotarget*, 2015, 6(3), 1359-1381). A further advantage of local or intratumoral or peritumoral administration is the ability to achieve equivalent efficacy at much lower doses, thus minimizing or eliminating adverse events that may be observed at much higher systemic doses (Marabelle, A., et al., Clinical Cancer Research, 2014, 20(7), p 1747-1756).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert excipient such as ethanol, glycerol, water and the like. Powders are prepared by reducing the compound to a suitable fine size and mixing with a similarly prepared pharmaceutical excipient such as an edible carbohydrate, as, for example, starch or mannitol. Flavouring, preservative, dispersing and colouring agent can also be present.

Capsules are made by preparing a powder mixture, as described above, and filling formed gelatin sheaths. Excipients including glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, excipients including suitable binders, glidants, lubricants, sweetening agents, flavours, disintegrating agents and colouring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, suspensions, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The composition can also be prepared to prolong or sustain the release as for example by coating or embedding particulate material in polymers, wax or the like.

The compounds of the invention may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. The compounds of the invention may also be administered in the form of a nanoparticulate delivery vehicle of which there are multiple compositions and methods of preparation. Both polymeric nanoparticles and properly composed and sized liposomes are particularly advantageous formulations for the treatment of cancer and in particular for the delivery of the compounds of the present invention as they are preferentially targeted to the tumor and lymph nodes. These targeting formulations have several potential advantages, these are: protecting the compounds of the present invention from degradation, increasing the amount of active agent at the site action and minimizing unwanted potential side effects as the result of excessive systemic exposure (Cai, Shuang et al., 2011 Advanced Drug Delivery Reviews, 2011, V 63, p 901-908). The potential utility of such approaches in the formulation of a CDN STING agonist has been demonstrated for formulations acting directly on tumors (Nakumura, T. et al., Journal of Controlled Release, 2015, V 216, p 149-157) and as use as an adjuvant (Hanson, M. et al., Journal of Clinical Investigation, 2015, V 125(6), p 2532-2546). Furthermore there are multiple modes of administration (intratumoral, subcutaneous, intravenous, intraperitoneal and intramuscular) of nanoparticle and liposomal formulations which may be of special utility to the compounds of the present invention. Specifically, similar to native CDN molecules, those of the present invention may be sensitive to degradation by phosphodiesterases that are present in or on host cells, for example in antigen presenting cells. The potency of a compound of the present invention may be diminished by such degradation, resulting in lower amount of induced expression of a signature molecule of innate immunity (e.g., IFN-beta). Hence, this degradation may afford weaker potency as measured by the release IFN-beta release from PBMCs or of reduced vaccine potency, as defined by the magnitude of a measured antigen-specific immune response.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Dosage forms for nasal or inhaled administration may conveniently be formulated as aerosols, solutions, suspensions drops, gels or dry powders.

Compositions for intranasal administration include aqueous compositions administered to the nose by drops or by pressurised pump. Suitable compositions contain water as the diluent or carrier for this purpose. Compositions for administration to the lung or nose may contain one or more excipients, for example one or more suspending agents, one or more preservatives, one or more surfactants, one or more tonicity adjusting agents, one or more co-solvents, and may include components to control the pH of the composition, for example a buffer system. Further, the compositions may contain other excipients such as antioxidants, for example sodium metabisulphite, and taste-masking agents. Compositions may also be administered to the nose or other regions of the respiratory tract by nebulisation.

Intranasal compositions may permit the compound(s) of Formula (I) or (a) pharmaceutically acceptable salt(s) thereof to be delivered to all areas of the nasal cavities (the target tissue) and further, may permit the compound(s) of Formula (I) or (a) pharmaceutically acceptable salt(s) thereof to remain in contact with the target tissue for longer periods of time. A suitable dosing regime for intranasal compositions would be for the patient to inhale slowly through the nose subsequent to the nasal cavity being cleared. During inhalation the composition would be administered to one nostril while the other is manually compressed. This procedure would then be repeated for the other nostril. Typically, one or two sprays per nostril would be administered by the above procedure one, two, or three times each day, ideally once daily. Of particular interest are intranasal compositions suitable for once-daily administration.

The suspending agent(s), if included, will typically be present in an amount of from 0.1 to 5% (w/w), such as from 1.5% to 2.4% (w/w), based on the total weight of the composition. Examples of pharmaceutically acceptable suspending agents include, but are not limited to, Avicel® (microcrystalline cellulose and carboxymethylcellulose sodium), carboxymethylcellulose sodium, veegum, tragacanth, bentonite, methylcellulose, xanthan gum, carbopol and polyethylene glycols.

Compositions for administration to the lung or nose may contain one or more excipients may be protected from microbial or fungal contamination and growth by inclusion of one or more preservatives. Examples of pharmaceutically acceptable anti-microbial agents or preservatives include, but are not limited to, quaternary ammonium compounds (for example benzalkonium chloride, benzethonium chloride, cetrimide, cetylpyridinium chloride, lauralkonium chloride and myristyl picolinium chloride), mercurial agents (for example phenylmercuric nitrate, phenylmercuric acetate and thimerosal), alcoholic agents (for example chlorobutanol, phenylethyl alcohol and benzyl alcohol), antibacterial esters (for example esters of para-hydroxybenzoic acid), chelating agents such as disodium edetate (EDTA) and other anti-microbial agents such as chlorhexidine, chlorocresol, sorbic acid and its salts (such as potassium sorbate) and polymyxin. Examples of pharmaceutically acceptable anti-fungal agents or preservatives include, but are not limited to, sodium benzoate, sorbic acid, sodium propionate, methylparaben, ethylparaben, propylparaben and butylparaben. The preservative(s), if included, may be present in an amount of from 0.001 to 1% (w/w), such as from 0.015% to 0.5% (w/w) based on the total weight of the composition.

Compositions (for example wherein at least one compound is in suspension) may include one or more surfactants which functions to facilitate dissolution of the medicament particles in the aqueous phase of the composition. For example, the amount of surfactant used is an amount which will not cause foaming during mixing. Examples of pharmaceutically acceptable surfactants include fatty alcohols, esters and ethers, such as polyoxyethylene (20) sorbitan monooleate (Polysorbate 80), macrogol ethers, and poloxamers. The surfactant may be present in an amount of between about 0.01 to 10% (w/w), such as from 0.01 to 0.75% (w/w), for example about 0.5% (w/w), based on the total weight of the composition.

One or more tonicity-adjusting agent(s) may be included to achieve tonicity with body fluids e.g. fluids of the nasal cavity, resulting in reduced levels of irritancy. Examples of pharmaceutically acceptable tonicity-adjusting agents include, but are not limited to, sodium chloride, dextrose, xylitol, calcium chloride, glucose, glycerine and sorbitol. A tonicity-adjusting agent, if present, may be included in an amount of from 0.1 to 10% (w/w), such as from 4.5 to 5.5% (w/w), for example about 5.0% (w/w), based on the total weight of the composition.

The compositions of the invention may be buffered by the addition of suitable buffering agents such as sodium citrate, citric acid, trometamol, phosphates such as disodium phosphate (for example the dodecahydrate, heptahydrate, dihydrate and anhydrous forms), or sodium phosphate and mixtures thereof.

A buffering agent, if present, may be included in an amount of from 0.1 to 5% (w/w), for example 1 to 3% (w/w) based on the total weight of the composition.

Examples of taste-masking agents include sucralose, sucrose, saccharin or a salt thereof, fructose, dextrose, glycerol, corn syrup, aspartame, acesulfame-K, xylitol, sorbitol, erythritol, ammonium glycyrrhizinate, thaumatin, neotame, mannitol, menthol, *eucalyptus* oil, camphor, a natural flavouring agent, an artificial flavouring agent, and combinations thereof.

One or more co-solvent(s) may be included to aid solubility of the medicament compound(s) and/or other excipients. Examples of pharmaceutically acceptable co-solvents include, but are not limited to, propylene glycol, dipropylene glycol, ethylene glycol, glycerol, ethanol, polyethylene glycols (for example PEG300 or PEG400), and methanol.

In one embodiment, the co-solvent is propylene glycol.

Co-solvent(s), if present, may be included in an amount of from 0.05 to 30% (w/w), such as from 1 to 25% (w/w), for example from 1 to 10% (w/w) based on the total weight of the composition.

Compositions for inhaled administration include aqueous, organic or aqueous/organic mixtures, dry powder or crystalline compositions administered to the respiratory tract by pressurised pump or inhaler, for example, reservoir dry powder inhalers, unit-dose dry powder inhalers, pre-metered multi-dose dry powder inhalers, nasal inhalers or pressurised aerosol inhalers, nebulisers or insufflators. Suitable compositions contain water as the diluent or carrier for this purpose and may be provided with conventional excipients such as buffering agents, tonicity modifying agents and the like. Aqueous compositions may also be administered to the nose and other regions of the respiratory tract by nebulisation. Such compositions may be aqueous solutions or suspensions or aerosols delivered from pressurised packs, such as a metered dose inhaler, with the use of a suitable liquefied propellant.

Compositions for administration topically to the nose (for example, for the treatment of rhinitis) or to the lung, include pressurised aerosol compositions and aqueous compositions delivered to the nasal cavities by pressurised pump. Compositions which are non-pressurised and are suitable for administration topically to the nasal cavity are of particular interest. Suitable compositions contain water as the diluent or carrier for this purpose. Aqueous compositions for administration to the lung or nose may be provided with conventional excipients such as buffering agents, tonicity-modifying agents and the like. Aqueous compositions may also be administered to the nose by nebulisation.

A fluid dispenser may typically be used to deliver a fluid composition to the nasal cavities. The fluid composition may be aqueous or non-aqueous, but typically aqueous. Such a fluid dispenser may have a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. The dispensing nozzle or orifice may be configured for insertion into the nostrils of the user for spray dispensing of the fluid composition into the nasal cavity. A fluid dispenser of the aforementioned type is described and illustrated in International Patent Application publication number WO 2005/044354 (Glaxo Group Limited). The dispenser has a housing which houses a fluid-discharge device having a compression pump mounted on a container for containing a fluid composition. The housing has at least one finger-operable side lever which is movable inwardly with respect to the housing to move the container upwardly in the housing by means of a cam to cause the pump to compress and pump a metered dose of the composition out of a pump stem through a nasal nozzle of the housing. In one embodiment, the fluid dispenser is of the general type illustrated in FIGS. 30-40 of WO 2005/044354.

Aqueous compositions containing a compound of Formula (I) or a pharmaceutically acceptable salt thereof may also be delivered by a pump as disclosed in International Patent Application publication number WO2007/138084 (Glaxo Group Limited), for example as disclosed with reference to FIGS. 22-46 thereof, or as disclosed in United Kingdom patent application number GB0723418.0 (Glaxo Group Limited), for example as disclosed with reference to FIGS. 7-32 thereof. The pump may be actuated by an actuator as disclosed in FIGS. 1-6 of GB0723418.0.

Dry powder compositions for topical delivery to the lung by inhalation may, for example, be presented in capsules and cartridges of for example gelatine, or blisters of for example laminated aluminium foil, for use in an inhaler or insufflator. Powder blend compositions generally contain a powder mix for inhalation of the compound of Formula (I) or a pharmaceutically acceptable salt thereof and a suitable powder base (carrier/diluent/excipient substance) such as mono-, di-, or polysaccharides (for example lactose or starch). Dry powder compositions may also include, in addition to the drug and carrier, a further excipient (for example a ternary agent such as a sugar ester for example cellobiose octaacetate, calcium stearate, or magnesium stearate.

In one embodiment, a composition suitable for inhaled administration may be incorporated into a plurality of sealed dose containers provided on medicament pack(s) mounted inside a suitable inhalation device. The containers may be rupturable, peelable, or otherwise openable one-at-a-time and the doses of the dry powder composition administered by inhalation on a mouthpiece of the inhalation device, as known in the art. The medicament pack may take a number of different forms, for instance a disk-shape or an elongate strip. Representative inhalation devices are the DISKHALER™ and DISKUS™ devices, marketed by GlaxoSmithKline.

A dry powder inhalable composition may also be provided as a bulk reservoir in an inhalation device, the device then being provided with a metering mechanism for metering a dose of the composition from the reservoir to an inhalation channel where the metered dose is able to be inhaled by a patient inhaling at a mouthpiece of the device. Exemplary marketed devices of this type are TURBUHALER™ (AstraZeneca), TWISTHALER™ (Schering) and CLICKHALER™ (Innovata.)

A further delivery method for a dry powder inhalable composition is for metered doses of the composition to be provided in capsules (one dose per capsule) which are then loaded into an inhalation device, typically by the patient on demand. The device has means to rupture, pierce or otherwise open the capsule so that the dose is able to be entrained into the patient's lung when they inhale at the device mouthpiece. As marketed examples of such devices there may be mentioned ROTAHALER™ (GlaxoSmithKline) and HANDIHALER™ (Boehringer Ingelheim.)

Pressurised aerosol compositions suitable for inhalation can be either a suspension or a solution and may contain a compound of Formula (I) or a pharmaceutically acceptable salt thereof and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional composition excipients well known in the art such as surfactants e.g. oleic acid, lecithin or an oligolactic acid or derivative thereof e.g. as described in WO 94/21229 and WO 98/34596 (Minnesota Mining and Manufacturing Company) and co-solvents e.g. ethanol. Pressurised compositions will generally be retained in a canister (e.g. an aluminium canister) closed with a valve (e.g. a metering valve) and fitted into an actuator provided with a mouthpiece.

Pharmaceutical compositions adapted for vaginal administration may be presented as pessaries, tampons, creams, gels, pastes, foams or spray formulations.

Pharmaceutical compositions adapted for injectable administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of formulation in question, for example those suitable for oral administration may include flavouring agents.

Antisense or RNA interference molecules may be administered to the mammal in need thereof. Alternatively, constructs including the same may be administered. Such molecules and constructs can be used to interfere with the expression of the protein of interest, e.g., histone demethylase and as such, modify histone demethylation. Typically delivery is by means known in the art.

Antisense or RNA interference molecules can be delivered in vitro to cells or in vivo, e.g., to tumors of a mammal. Nodes of delivery can be used without limitations, including: intravenous, intramuscular, intraperitoneal, intra-arterial, local delivery during surgery, endoscopic, subcutaneous, and per os. Vectors can be selected for desirable properties for any particular application. Vectors can be viral or plasmid. Adenoviral vectors are useful in this regard. Tissue-specific, cell-type specific, or otherwise regulatable promoters can be used to control the transcription of the inhibitory polynucleotide molecules. Non-viral carriers such as liposomes or nanospheres can also be used.

The compounds of Formula (I) and pharmaceutically acceptable salts thereof may also be formulated to produce a composition for use as an adjuvant to modulate vaccine activity. Such compositions may contain antibody(ies) or antibody fragment(s) or an antigenic component including but not limited to protein, DNA, live or dead bacteria and/or viruses or virus-like particles, together with one or more components with adjuvant activity including but not limited to aluminium salts, oil and water emulsions, heat shock proteins, lipid A preparations and derivatives, glycolipids, other TLR agonists such as CpG DNA or similar agents, cytokines such as GM-CSF or IL-12 or similar agents.

A therapeutically effective amount of the agent will depend upon a number of factors including, for example, the age and weight of the subject, the precise condition requiring treatment and its severity, the nature of the formulation, and the route of administration, and will ultimately be at the discretion of the attendant physician or veterinarian. In particular, the subject to be treated is a mammal, particularly a human.

The agent may be administered in a daily dose. This amount may be given in a single dose per day or more usually in a number (such as two, three, four, five or six) of sub-doses per day such that the total daily dose is the same.

Suitably, the amount of the compound of the invention administered according to the present invention will be an amount selected from 0.01 mg to 1 g per day (calculated as the free or unsalted compound).

The compounds of Formula (I) and pharmaceutically acceptable salts thereof may be employed alone or in combination with other therapeutic agents. The compounds of Formula (I) and pharmaceutically acceptable salts thereof and the other pharmaceutically active agent(s) may be administered together or separately and, when administered separately, administration may occur simultaneously or sequentially, in any order, by any convenient route in separate or combined pharmaceutical compositions.

The amounts of the compound(s) of Formula (I) or pharmaceutically acceptable salt(s) thereof and the other pharmaceutically active agent(s) and the relative timings of administration will be selected in order to achieve the desired combined therapeutic effect. The compounds of the present invention and further therapeutic agent(s) may be employed in combination by administration simultaneously in a unitary pharmaceutical composition including both compounds. Alternatively, the combination may be administered separately in separate pharmaceutical compositions, each including one of the compounds in a sequential manner wherein, for example, the compound of the invention is administered first and the other second and visa versa. Such sequential administration may be close in time (e.g. simultaneously) or remote in time. Furthermore, it does not matter if the compounds are administered in the same dosage form, e.g. one compound may be administered topically and the other compound may be administered orally.

The combinations may be presented as a combination kit. By the term "combination kit" "or kit of parts" as used herein is meant the pharmaceutical composition or compositions that are used to administer the combination according to the invention. When both compounds are administered simultaneously, the combination kit can contain both compounds in a single pharmaceutical composition, such as a tablet, or in separate pharmaceutical compositions. When the compounds are not administered simultaneously, the combination kit will contain each compound in separate pharmaceutical compositions either in a single package or in separate pharmaceutical compositions in separate packages.

The combination kit can also be provided by instruction, such as dosage and administration instructions. Such dosage and administration instructions can be of the kind that are provided to a doctor, for example by a drug product label, or they can be of the kind that are provided by a doctor, such as instructions to a patient.

When the combination is administered separately in a sequential manner wherein one is administered first and the other second or vice versa, such sequential administration may be close in time or remote in time. For example, administration of the other agent several minutes to several dozen minutes after the administration of the first agent, and administration of the other agent several hours to several days after the administration of the first agent are included, wherein the lapse of time is not limited. For example, one agent may be administered once a day, and the other agent may be administered 2 or 3 times a day, or one agent may be administered once a week, and the other agent may be administered once a day and the like.

It will be clear to a person skilled in the art that, where appropriate, the other therapeutic ingredients(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

When combined in the same composition it will be appreciated that the two compounds must be stable and compatible with each other and the other components of the composition and may be formulated for administration. When formulated separately they may be provided in any convenient composition, conveniently, in such a manner as known for such compounds in the art.

When the compound of Formula (I) is used in combination with a second therapeutic agent active against the same disease, condition or disorder, the dose of each compound may differ from that when the compound is used alone. Appropriate doses will be readily appreciated by those skilled in the art.

In one embodiment the mammal in the methods and uses of the present invention is a human.

The invention also provides a pharmaceutical composition comprising from 0.5 to 1,000 mg of a compound of Formula (I) or pharmaceutically acceptable salt thereof and from 0.5 to 1,000 mg of a pharmaceutically acceptable excipient.

The compounds of the invention are useful in the treatment of diseases in which modulation of STING is beneficial. This includes inflammation, allergic and autoimmune diseases, infectious diseases, cancer and pre-cancerous syndromes.

As modulators of the immune response the compounds of Formula (I) and pharmaceutically acceptable salts thereof may also be useful, as stand-alone or in combination as an adjuvant in the treatment of diseases in which modulation of STING is beneficial.

In one aspect, the disease or condition is inflammation, allergy and autoimmune disorders Autoimmune diseases associated include, but are not limited to systemic lupus erythmatosus, Psoriasis, insulin-dependent diabetes mellitus (IDDM), dermatomyositis, human immunodeficiency virus (HIV), AIDS, and Sjogren's syndrome (SS).

Inflammation represents a group of vascular, cellular and neurological responses to trauma. Inflammation can be characterised as the movement of inflammatory cells such as monocytes, neutrophils and granulocytes into the tissues. This is usually associated with reduced endothelial barrier function and oedema into the tissues. Inflammation can be classified as either acute or chronic. Acute inflammation is the initial response of the body to harmful stimuli and is achieved by the increased movement of plasma and leukocytes from the blood into the injured tissues. A cascade of biochemical event propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterised by simultaneous destruction and healing of the tissue from the inflammatory process.

When occurring as part of an immune response to infection or as an acute response to trauma, inflammation can be beneficial and is normally self-limiting. However, inflammation can be detrimental under various conditions. This includes the production of excessive inflammation in response to infectious agents, which can lead to significant organ damage and death (for example, in the setting of sepsis). Moreover, chronic inflammation is generally deleterious and is at the root of numerous chronic diseases, causing severe and irreversible damage to tissues. In such settings, the immune response is often directed against self-tissues (autoimmunity), although chronic responses to foreign entities can also lead to bystander damage to self tissues.

The aim of anti-inflammatory therapy is therefore to reduce this inflammation, to inhibit autoimmunity when present and to allow for the physiological process or healing and tissue repair to progress.

The agents may be used to treat inflammation of any tissue and organs of the body, including musculoskeletal inflammation, vascular inflammation, neural inflammation, digestive system inflammation, ocular inflammation, inflammation of the reproductive system, and other inflammation, as exemplified below.

Musculoskeletal inflammation refers to any inflammatory condition of the musculoskeletal system, particularly those conditions affecting skeletal joints, including joints of the hand, wrist, elbow, shoulder, jaw, spine, neck, hip, knew, ankle, and foot, and conditions affecting tissues connecting muscles to bones such as tendons. Examples of musculoskeletal inflammation which may be treated with compounds of the invention include arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic).

Ocular inflammation refers to inflammation of any structure of the eye, including the eye lids. Examples of ocular inflammation which may be treated with the compounds of the invention include blepharitis, blepharochalasis, conjunctivitis, dacryoadenitis, keratitis, keratoconjunctivitis sicca (dry eye), scleritis, trichiasis, and uveitis.

Examples of inflammation of the nervous system which may be treated with the compounds of the invention include encephalitis, Guillain-Barre syndrome, meningitis, neuromyotonia, narcolepsy, multiple sclerosis, myelitis and schizophrenia.

Examples of inflammation of the vasculature or lymphatic system which may be treated with the compounds of the invention include arthrosclerosis, arthritis, phlebitis, vasculitis, and lymphangitis.

Examples of inflammatory conditions of the digestive system which may be treated with the compounds of the invention include cholangitis, cholecystitis, enteritis, enterocolitis, gastritis, gastroenteritis, inflammatory bowel disease (such as Crohn's disease and ulcerative colitis), ileitis, and proctitis.

Examples of inflammatory conditions of the reproductive system which may be treated with the compounds of the invention include cervicitis, chorioamnionitis, endometritis, epididymitis, omphalitis, oophoritis, orchitis, salpingitis, tubo-ovarian abscess, urethritis, vaginitis, vulvitis, and vulvodynia.

The agents may be used to treat autoimmune conditions having an inflammatory component. Such conditions include acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome, Grave's disease, Guillain-Barre syndrome, Hashimoto's disease, Henoch-Schönlein purpura, Kawasaki's disease, lupus erythematosus, microscopic colitis, microscopic polyarteritis, mixed connective tissue disease, multiple sclerosis, myasthenia gravis, opsocionus myoclonus syndrome, optic neuritis, ord's thyroiditis, pemphigus, polyarteritis *nodosa*, polymyalgia, rheumatoid arthritis, Reiter's syndrome, Sjogren's syndrome, temporal arteritis, Wegener's granulomatosis, warm autoimmune haemolytic anemia, interstitial cystitis, lyme disease, morphea, psoriasis, sarcoidosis, scleroderma, ulcerative colitis, and vitiligo.

The agents may be used to treat T-cell mediated hypersensitivity diseases having an inflammatory component. Such conditions include contact hypersensitivity, contact dermatitis (including that due to poison ivy), uticaria, skin allergies, respiratory allergies (hayfever, allergic rhinitis) and gluten-sensitive enteropathy (Celliac disease).

Other inflammatory conditions which may be treated with the agents include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xengrafts, serum sickness, and graft vs host disease), acute pancreatitis, chronic pancreatitis, acute respiratory distress syndrome, Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, astopic dermatitis, drug hypersensistivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autroimmine) haemolytic anemia, leukaemia and lymphomas in adults, acute leukaemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosis, psoriasis, chronic pulmonary disease, and inflammation accompanying infectious conditions (e.g., sepsis).

In a further aspect of the invention there is provided a compound of Formula (I) or a pharmaceutically acceptable salt thereof for use in the treatment of inflammation, allergy and autoimmune disease.

In a further aspect there is provided a method of treating inflammation, allergy and autoimmune disease comprising administering to a human in need thereof a therapeutically effective amount of a compound of Formula (I) or a pharmaceutically acceptable salt thereof.

In a further aspect there is provided the use of a compound of Formula (I) or a pharmaceutically acceptable salt thereof in the manufacture of a medicament for the treatment of inflammation, allergy and autoimmune disease.

In one aspect the disease to be treated is asthma.

The compounds of Formula (I) and pharmaceutically acceptable salts thereof may be used in combination with one or more other agents which may be useful in the prevention or treatment of allergic disease, inflammatory disease, autoimmune disease, for example; antigen immunotherapy, anti-histamines, steroids, NSAIDs, bronchodilators (e.g. beta 2 agonists, adrenergic agonists, anticholinergic agents, theophylline), methotrexate, leukotriene modulators and similar agents; monoclonal antibody therapy such as anti-lgE, anti-TNF, anti-IL-5, anti-IL-6, anti-IL-12, anti-IL-1 and similar agents; receptor therapies e.g. entanercept and similar agents; antigen non-specific immunotherapies (e.g. interferon or other cytokines/chemokines, cytokine/chemokine receptor modulators, cytokine agonists or antagonists, TLR agonists and similar agents).

In a further aspect there is provided a combination comprising a compound of Formula (I) or a pharmaceutically acceptable salt thereof and at least one further therapeutic agent useful in the treatment of allergic disease, inflammation or autoimmune disease.

In a further aspect there is provided a combination comprising a compound of Formula (I) or a pharmaceutically acceptable salt thereof and at least one further therapeutic agent useful in the treatment of allergic disease, inflammation or autoimmune disease for use in therapy.

In a further aspect there is provided a combination comprising a compound of Formula (I) or pharmaceutically acceptable salt thereof and at least one one further therapeutic agent useful in the treatment of allergic disease, inflammation or autoimmune disease, for use in the treatment of allergic disease, inflammation or autoimmune disease.

In a further aspect there is provided the use of a combination comprising a compound of Formula (I) or a pharmaceutically acceptable salt thereof and at least one one further therapeutic agent useful in the treatment of allergic disease, inflammation or autoimmune diseasein the manufacture of a medicament for the treatment of allergic disease, inflammation or autoimmune disease.

In a further aspect there is provided a method of treating allergic disease, inflammation or autoimmune disease comprising administering to a human in need thereof a therapeutically effective amount of a combination comprising a compound of Formula (I) or a pharmaceutically acceptable salt thereof and at least one further therapeutic agent useful in the treatment of allergic disease, inflammation or autoimmune disease.

In a further aspect there is provided a pharmaceutical composition comprising a combination comprising a compound of Formula (I) or a pharmaceutically acceptable salt thereof and at least one further therapeutic agent useful in the treatment of allergic disease, inflammation or autoimmune disease and one or more of pharmaceutically acceptable excipients.

In one aspect the disease to be treated with such a combination is asthma.

In one aspect the disease or condition to be treated is cancer.

Examples of cancer diseases in which compounds of Formula (I), or pharmaceutically acceptable salts or solvates thereof may have potentially beneficial antitumour effects include, but are not limited to, cancers of the lung, bone, pancreas, skin, head, neck, uterus, ovaries, stomach, colon, breast, esophagus, small intestine, bowel, endocrine system, thyroid glad, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemagioma; hepatoma; fibrosarcoma; chondrosarcoma; myeloma; chronic or acute leukemia; lymphocytic lymphomas; primary CNS lymphoma; neoplasms of the CNS; spinal axis tumours; squamous cell carcinomas; synovial sarcoma; malignant pleural mesotheliomas; brain stem glioma; pituitary adenoma; bronchial adenoma; chondromatous hanlartoma; inesothelioma; Hodgkin's Disease or a combination of one or more of the foregoing cancers.

Suitably the present invention relates to a method for treating or lessening the severity of cancers selected from the group consisting of brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal adenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocytic leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

Suitably the present invention relates to a method for treating or lessening the severity of pre-cancerous syndromes in a mammal, including a human, wherein the pre-cancerous syndrome is selected from: cervical intraepithelial neoplasia, monoclonal gammapathy of unknown significance (MGUS), myelodysplastic syndrome, aplastic anemia, cervical lesions, skin nevi (pre-melanoma), prostatic intraepithleial (intraductal) neoplasia (PIN), Ductal Carcinoma in situ (DCIS), colon polyps and severe hepatitis or cirrhosis.

The compounds of the present invention may also be used as adjuvants to improve the immune response raised to any given antigen and/or reduce reactogenicity/toxicity in a patient, particularly a human, in need thereof. As such, a compound of this invention may be used in combination with vaccine compositions to modify, especially to enhance, the immune response for example by increasing the level or duration of protection and/or allowing a reduction in the antigenic dose.

The compounds of Formula (I) and pharmaceutically acceptable salts thereof may be used in combination with one or more vaccines or immunogenic antigens useful in the prevention or treatment of viral infections. Such vaccines or immunogenic antigens include, without limitation to pathogen derived proteins or particles such as attenuated viruses, virus particles, and viral proteins typically used as immunogenic substances. Examples of viruses and viral antigens include, without limitations to Polioviruses, Cioronaviridae and Coronaviruses, Rhinovirus (all subtypes), Adenoviruses (all subtypes), Hepatitis A, Hepatitis B, Hepatitis C, Hepatitis D, Human papillomavirus (including all subtypes), Rabies viruses, Human T-cell lympotropic virus (all subtypes), Rubella virus, Mumps virus, Coxsackie virus A (all subtypes), Cosackie virus B (all subtypes), human enteroviruses, herpesviruses including cytomegalovirus, Epstein-Barr virus, human herepesviruses (all subtypes), herpes simplex virus, varicella zoster virus, human immunodeficiency virus (HIV) (all subtypes), AIDS, Epstein-Barr virus, Reoviruses (all subtypes), Filoviruses including Marburg virus and Ebola virus (all stains), Arenaviruses including Lymphocytic choriomeningitis virus, Lassa virus, Junin virus, and Machupo virus, Arboviruses including West Nile virus, Dengue viruses (all serotypes), Zika virus, Colorado tick fever virus, Sindbis virus, Togaviraidae, Flaviviridae, Bunyaviridae, Reoviridae, Rhabdoviridae, Orthomyxoviridae, Poxviruses including orthopoxvirus (variola virus, monkypox virus, vaccinia virus, cowpox virus), yatapoxviruses (tanapox virus, Yaba monkey tumor virus), parapoxvirus, molluscipoxvirus, Yellow fever, Hantaviruses including Hantaan, Seoul, Dobrava, Sin Nombre, Puumala, and Dobrava-like Saaremaa, human para influenza viruses and influenza viruses (all types), H1N1 influenza and swine influenza viruses, respiratory syncytial virus (all subgroups), rotaviruses including human rotaviruses A-E, bovine rotavirus, rhesus monkey rotavirus, Polyomaviruses including simian virus 40, JC virus, BK virus, Coltiviruses, eyach virus, calciviruses, and Parvoviridae including dependovirus, parvovirus and erythrovirus.

The compounds of the present invention may also be useful in the treatment of one or more diseases afflicting mammals which are characterized by cellular proliferation in the area of disorders associated with neo-vascularization and/or vascular permeability including blood vessel proliferative disorders including arthritis (rheumatoid arthritis) and restenosis; fibrotic disorders including hepatic cirrhosis and atherosclerosis; mesangial cell proliferative disorders include glomerulonephritis, diabetic nephropathy, malignant nephrosclerosis, thrombotic microangiopathy syndromes, proliferative retinopathies, organ transplant rejection and glomerulopathies; and metabolic disorders include psoriasis, diabetes mellitus, chronic wound healing, inflammation and neurodegenerative diseases.

In a further aspect of the invention there is provided a compound of Formula (I) or a pharmaceutically acceptable salt thereof for use in the treatment of a disease state selected from the group consisting of: HIV, HBV, HCV, influenza, skin warts, multiple sclerosis, allergic inflammation, and as an adjuvant.

Zhijian Chen—Regulation and function of the cGAS-STING pathway of cytosolic DNA sensing—Nature Immunology (2016), 17, 1142-1149.

Seng-Ryong Woo—STING-Dependent Cytosolic DNA Sensing Mediates Innate Immune Recognition of Immunogenic Tumors (2014), 41, 830-842.

Jenny P.-Y. Ting—NLRX1 Sequesters STING to Negatively Regulate the Interferon Response, Thereby Facilitating the Replication of HIV-1 and DNA Viruses—Cell Host and Microbe (2016), 19, 515-528.

Zhijian Chen—Pivotal Roles of cGAS-cGAMP Signaling in Antiviral Defense and Immune Adjuvant Effects—Science (2013), 341, 1390-1394.

Nuchsupha Sunthamala—E2 Proteins of High Risk Human Papillomaviruses Down-Modulate STING and IFN-k Transcription in Keratinocytes—PLoS (2014), 9, 1-11.

Guo, H., et al. (2016). NLRX1 Sequesters STING to Negatively Regulate the Interferon Response, Thereby Facilitating the Replication of HIV-1 and DNA Viruses. Cell host & microbe 19, 515-528.

Gao, D., et al. (2013). Cyclic GMP-AMP synthase is an innate immune sensor of HIV and other retroviruses. Science 341, 903-906.

Guo, F., et al. (2015). Sting agonists induce an innate antiviral immune response against hepatitis B virus. Antimicrobial Agents and Chemotherapy 59, 1273-1281.

Dansako, H., et al. (2016). The cyclic GMP-AMP synthetase-STING signaling pathway is required for both the innate immune response against HBV and the suppression of HBV assembly. FEBS J 283, 144-156.

Chang, J., et al. (2015). Treatment of chronic hepatitis B with pattern recognition receptor agonists: Current status and potential for a cure. Antiviral Research 121, 152-159.

Li, X. D., et al. (2013). Pivotal roles of cGAS-cGAMP signaling in antiviral defense and immune adjuvant effects. Science 341, 1390-1394.

Carroll, E. C., et al. (2016). The Vaccine Adjuvant Chitosan Promotes Cellular Immunity via DNA Sensor cGAS-STING-Dependent Induction of Type I Interferons. Immunity 44, 597-608.

Wang, J., et al. (2016). Natural STING Agonist as an "Ideal" Adjuvant for Cutaneous Vaccination. J Invest Dermatol 136, 2183-2191.

Holm, C. K., et al. (2016). Influenza A virus targets a cGAS-independent STING pathway that controls enveloped RNA viruses. Nat Commun 7, 10680.

Shirey, K. A., et al. (2011). The anti-tumor agent, 5,6-dimethylxanthenone-4-acetic acid (DMXAA), induces IFN-beta-mediated antiviral activity in vitro and in vivo. J Leukoc Biol 89, 351-357.

Nitta, S., et al. (2013). Hepatitis C virus NS4B protein targets STING and abrogates RIG-I-mediated type I interferon-dependent innate immunity. Hepatology 57, 46-58.

Sunthamala, N., et al. (2014). E2 proteins of high risk human papillomaviruses down-modulate STING and IFN-kappa transcription in keratinocytes. PLoS One 9, e91473.

Lau, L., et al. (2015). DNA tumor virus oncogenes antagonize the cGAS-STING DNA-sensing pathway. Science 350, 568-571.

Kidd, P. (2003). Th1/Th2 balance: the hypothesis, its limitations, and implications for health and disease. Altern Med Rev 8, 223-246.

Huang, L., et al. (2013). Cutting edge: DNA sensing via the STING adaptor in myeloid dendritic cells induces potent tolerogenic responses. J Immunol 191, 3509-3513.

Lemos, H., et al. (2014). Activation of the STING adaptor attenuates experimental autoimmune encephalitis. J Immunol 192, 5571-5578.

In a further aspect of the invention there is provided a compound of Formula (I) or a pharmaceutically acceptable salt thereof for use in the treatment of cancer and/or pre-cancerous syndromes.

In a further aspect there is provided a method of treating cancer comprising administering to a human in need thereof a therapeutically effective amount of a compound of Formula (I) or a pharmaceutically acceptable salt thereof.

In a further aspect there is provided the use of a compound of Formula (I) or a pharmaceutically acceptable salt thereof in the manufacture of a medicament for the treatment of cancer and/or pre-cancerous syndromes.

In one embodiment, the compound of the invention may be employed with other therapeutic methods of cancer treatment. In particular, in anti-neoplastic therapy, combination therapy with other chemotherapeutic, hormonal, antibody agents as well as surgical and/or radiation treatments other than those mentioned above are envisaged.

In one embodiment, the further anti-cancer therapy is surgical and/or radiotherapy.

In one embodiment, the further anti-cancer therapy is at least one additional anti-neoplastic agent.

In a further aspect there is provided a combination comprising a compound of Formula (I) or a pharmaceutically acceptable salt thereof and at least one anti-neoplastic agent.

In a further aspect there is provided a combination comprising a compound of Formula (I) or a pharmaceutically acceptable salt thereof and at least one anti-neoplastic agent, for use in therapy.

In a further aspect there is provided a combination comprising a compound of Formula (I) or pharmaceutically acceptable salt thereof and at least one anti-neoplastic agent, for use in treating cancer and/or pre-cancerous syndromes.

In a further aspect there is provided the use of a combination comprising a compound of Formula (I) or a pharmaceutically acceptable salt thereof and at least one anti-neoplastic agent, in the manufacture of a medicament for the treatment of cancer and/or pre-cancerous syndromes.

In a further aspect there is provided a method of treating cancer, comprising administering to a human in need thereof a therapeutically effective amount of a combination comprising a compound of Formula (I) or a pharmaceutically acceptable salt thereof and at least one anti-neoplastic agent.

In a further aspect there is provided a pharmaceutical composition comprising a combination comprising a compound of Formula (I) or a pharmaceutically acceptable salt thereof and at least one further therapeutic agent, particularly at least one anti-neoplastic agent and one or more of pharmaceutically acceptable carriers, diluents and excipients.

Any anti-neoplastic agent that has activity versus a susceptible tumor being treated may be utilized in the combination. Typical anti-neoplastic agents useful include, but are not limited to, anti-microtubule agents such as diterpenoids and *vinca* alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine angiogenesis inhibitors; immunotherapeutic agents; proapoptotic agents; cell cycle signaling inhibitors; immuno-oncology agents and immunostimulatory agents.

Anti-microtubule or Anti-mitotic Agents:

Anti-microtubule or anti-mitotic agents are phase specific agents active against the microtubules of tumor cells during M or the mitosis phase of the cell cycle. Examples of anti-microtubule agents include, but are not limited to, diterpenoids and *vinca* alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein.

Disassembly of the protein appears then to be inhibited with mitosis being arrested and cell death following.

Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797,1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide. 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine,N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree.

*Vinca* alkaloids are phase specific anti-neoplastic agents derived from the periwinkle plant. *Vinca* alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of *vinca* alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro -4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic *vinca* alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum Coordination Complexes:

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, oxaliplatin, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma.

Alkylating Agents:

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease.

Busulfan, 1,4-butanediol dimethanesulfonate, is commercially available as MYLERAN® TABLETS. Busulfan is indicated for the palliative treatment of chronic myelogenous leukemia.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease.

Antibiotic Anti-neoplastics:

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also known as Actinomycin D, is commercially available in injectable form as COSMEGEN®. Dactinomycin is indicated for the treatment of Wilm's tumor and rhabdomyosarcoma.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas.

Topoisomerase II Inhibitors:

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children.

Antimetabolite Neoplastic Agents:

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine).

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Other purine analogs include pentostatin, erythrohydroxynonyladenine, fludarabine phosphate, and cladribine.

Gemcitabine, 2'-deoxy-2', 2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer.

Methotrexate, N-[4[[(2,4-diamino-6-pteridinyl) methyl] methylamino] benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder.

Topoisomerase I Inhibitors:

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®. Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer.

Hormones and Hormonal Analogues:

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, estrogens, and anti-estrogens such as fulvestrant, flutamide, nilutamide, bicalutamide, cyproterone acetate and 5α-reductases such as finasteride and dutasteride, useful in the treatment of prostatic carcinoma and benign prostatic hypertrophy; antiestrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal Transduction Pathway Inhibitors:

Signal transduction pathway inhibitors are those inhibitors, which block or inhibit a chemical process which evokes an intracellular change. As used herein this change is cell proliferation or differentiation. Signal transduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 February 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-lacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Anti-angiogenic Agents:
(i) Anti-angiogenic agents including non-receptor MEK angiogenesis inhibitors may alo be useful. Anti-angiogenic agents such as those which inhibit the effects of vascular edothelial growth factor, (for example the anti-vascular endothelial cell growth factor antibody bevacizumab [Avastin™], and compounds that work by other mechanisms (for example linomide, inhibitors of integrin αvβ3 function, endostatin and angiostatin);

Immunotherapeutic Agents:
Agents used in immunotherapeutic regimens may also be useful in combination with the compounds of Formula (I). Immunotherapy approaches, including for example ex-vivo and in-vivo approaches to increase the immunogenecity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies Proapoptotic Agents:
Agents used in proapoptotic regimens (e.g., bcl-2 antisense oligonucleotides) may also be used in the combination of the present invention.

Cell Cycle Signalling Inhibitors
Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the combination of the present invention comprises a compound of Formula I or a salt or solvate thereof and at least one anti-neoplastic agent selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine MEK angiogenesis inhibitors, immunotherapeutic agents, proapoptotic agents, and cell cycle signaling inhibitors.

In one embodiment, the combination of the present invention comprises a compound of Formula I or a salt or solvate thereof and at least one anti-neoplastic agent which is an anti-microtubule agent selected from diterpenoids and *vinca* alkaloids.

In a further embodiment, at least one anti-neoplastic agent is a diterpenoid.

In a further embodiment, at least one anti-neoplastic agent is a *vinca* alkaloid.

In one embodiment, the combination of the present invention comprises a compound of Formula I or a salt or solvate thereof and at least one anti-neoplastic agent, which is a platinum coordination complex.

In a further embodiment, at least one anti-neoplastic agent is paclitaxel, carboplatin, or vinorelbine.

In a further embodiment, at least one anti-neoplastic agent is carboplatin.

In a further embodiment, at least one anti-neoplastic agent is vinorelbine.

In a further embodiment, at least one anti-neoplastic agent is paclitaxel.

In one embodiment, the combination of the present invention comprises a compound of Formula I and salts or solvates thereof and at least one anti-neoplastic agent which is a signal transduction pathway inhibitor.

In a further embodiment the signal transduction pathway inhibitor is an inhibitor of a growth factor receptor kinase VEGFR2, TIE2, PDGFR, BTK, erbB2, EGFr, IGFR-1, TrkA, TrkB, TrkC, or c-fms.

In a further embodiment the signal transduction pathway inhibitor is an inhibitor of a serine/threonine kinase rafk, akt, or PKC-zeta.

In a further embodiment the signal transduction pathway inhibitor is an inhibitor of a non-receptor tyrosine kinase selected from the src family of kinases.

In a further embodiment the signal transduction pathway inhibitor is an inhibitor of c-src.

In a further embodiment the signal transduction pathway inhibitor is an inhibitor of Ras oncogene selected from inhibitors of farnesyl transferase and geranylgeranyl transferase.

In a further embodiment the signal transduction pathway inhibitor is an inhibitor of a serine/threonine kinase selected from the group consisting of PI3K.

In a further embodiment the signal transduction pathway inhibitor is a dual EGFr/erbB2 inhibitor, for example N-{3-Chloro-4-[(3-fluorobenzyl) oxy]phenyl}-6-[5-({[2-(methanesulphonyl) ethyl]amino}methyl)-2-furyl]-4-quinazolinamine (structure below):

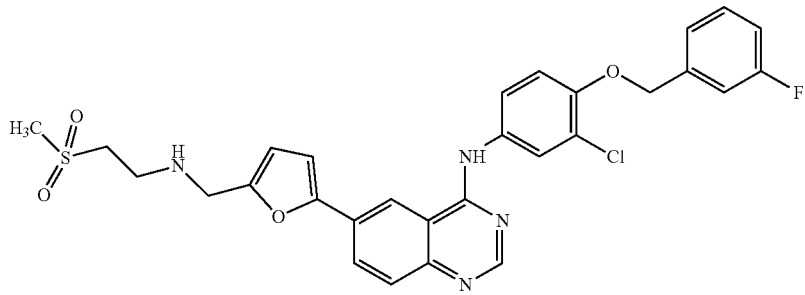 [SMILES: CS(=O)(=O)CCNCc1ccc(-c2ccc3ncnc(Nc4ccc(OCc5cccc(F)c5)c(Cl)c4)c3c2)o1]

In one embodiment, the combination of the present invention comprises a compound of Formula I or a salt or solvate thereof and at least one anti-neoplastic agent which is a cell cycle signaling inhibitor.

In further embodiment, cell cycle signaling inhibitor is an inhibitor of CDK2, CDK4 or CDK6.

Immunostimulatory Agents:

As used herein "immunostimulatory agent" refers to any agent that can stimulate the immune system. As used herein immunostimulatory agents include, but are not limited to, vaccine adjuvants, such as Toll-like receptor agonists, T-cell checkpoint blockers, such as mAbs to PD-1 and CTL4 and T-cell checkpoint agonist, such as agonist mAbs to OX-40 and ICOS.

Additional examples of a further active ingredient or ingredients (anti-neoplastic agent) for use in combination or co-administered with the presently invented compound of Formula (I) are anti-PD-L1 agents.

Anti-PD-L1 antibodies and methods of making the same are known in the art.

Such antibodies to PD-L1 may be polyclonal or monoclonal, and/or recombinant, and/or humanized.

Exemplary PD-L1 antibodies are disclosed in:

U.S. Pat. No. 8,217,149; Ser. No. 12/633,339;
U.S. Pat. No. 8,383,796; Ser. No. 13/091,936;
U.S. Pat. No. 8,552,154; Ser. No. 13/120,406;
US patent publication No. 20110280877; Ser. No. 13/068,337;
US Patent Publication No. 20130309250; Ser. No. 13/892,671;
WO2013019906;
WO2013079174;
U.S. application Ser. No. 13/511,538 (filed Aug. 7, 2012), which is the US National Phase of International Application No. PCT/US10/58007 (filed 2010); and
U.S. application Ser. No. 13/478,511 (filed May 23, 2012).

Additional exemplary antibodies to PD-L1 (also referred to as CD274 or B7-H1) and methods for use are disclosed in U.S. Pat. No. 7,943,743; US20130034559, WO2014055897, U.S. Pat. Nos. 8,168,179; and 7,595,048. PD-L1 antibodies are in development as immuno-modulatory agents for the treatment of cancer.

In one embodiment, the antibody to PD-L1 is an antibody disclosed in U.S. Pat. No. 8,217,149. In another embodiment, the anti-PD-L1 antibody comprises the CDRs of an antibody disclosed in U.S. Pat. No. 8,217,149.

In another embodiment, the antibody to PD-L1 is an antibody disclosed in U.S. application Ser. No. 13/511,538.

In another embodiment, the anti-PD-L1 antibody comprises the CDRs of an antibody disclosed in U.S. application Ser. No. 13/511,538.

In another embodiment, the antibody to PD-L1 is an antibody disclosed in application Ser. No. 13/478,511. In another embodiment, the anti-PD-L1 antibody comprises the CDRs of an antibody disclosed in U.S. application Ser. No. 13/478,511.

In one embodiment, the anti-PD-L1 antibody is BMS-936559 (MDX-1105). In another embodiment, the anti-PD-L1 antibody is MPDL3280A (RG7446). In another embodiment, the anti-PD-L1 antibody is MEDi4736.

Additional examples of a further active ingredient or ingredients (anti-neoplastic agent) for use in combination or co-administered with the presently invented compound of Formula (I) are PD-1 antagonist.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any embodiments of the aspects or embodiments of the present invention in which a human individual is to be treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in the any of the aspects of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the various aspects and embodiments of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Specific anti-human PD-1 mAbs useful as the PD-1 antagonist in any of the aspects and embodiments of the present invention include: MK-3475, a humanized IgG4 mAb with the structure described in WHO Drug Information, Vol. 27, No. 2, pages 161-162 (2013) and which comprises the heavy and light chain amino acid sequences shown in FIG. 6; nivolumab, a human IgG4 mAb with the structure described in WHO Drug Information, Vol. 27, No. 1, pages 68-69 (2013) and which comprises the heavy and light chain amino acid sequences shown in FIG. 7; the humanized antibodies h409A11, h409A16 and h409A17, which are described in WO2008/156712, and AMP-514, which is being developed by Medimmune.

Other PD-1 antagonists useful in the any of the aspects and embodiments of the present invention include an immunoadhesin that specifically binds to PD-1, and preferably specifically binds to human PD-1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Other examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDi4736, MSB0010718C.

KEYTRUDA/pembrolizumab is an anti-PD-1 antibody marketed for the treatment of lung cancer by Merck. The amino acid sequence of pembrolizumab and methods of using are disclosed in U.S. Pat. No. 8,168,757.

Opdivo/nivolumab is a fully human monoclonal antibody marketed by Bristol Myers Squibb directed against the negative immunoregulatory human cell surface receptor PD-1 (programmed death-1 or programmed cell death-1/PCD-1) with immunopotentiation activity. Nivolumab binds to and blocks the activation of PD-1, an Ig superfamily transmembrane protein, by its ligands PD-L1 and PD-L2, resulting in the activation of T-cells and cell-mediated immune responses against tumor cells or pathogens. Activated PD-1 negatively regulates T-cell activation and effector function through the suppression of PI3k/Akt pathway activation. Other names for nivolumab include: BMS-936558, MDX-1106, and ONO-4538. The amino acid sequence for nivolumab and methods of using and making are disclosed in U.S. Pat. No. 8,008,449.

Additional examples of a further active ingredient or ingredients (anti-neoplastic agent) for use in combination or co-administered with the presently invented compound of Formula (I) are immuno-modulators.

As used herein "immuno-modulators" refer to any substance including monoclonal antibodies that affects the immune system. The ICOS binding proteins of the present invention can be considered immune-modulators. Immuno-modulators can be used as anti-neoplastic agents for the treatment of cancer. For example, immune-modulators include, but are not limited to, anti-CTLA-4 antibodies such as ipilimumab (YERVOY) and anti-PD-1 antibodies (Opdivo/nivolumab and Keytruda/pembrolizumab). Other immuno-modulators include, but are not limited to, OX-40 antibodies, PD-L1 antibodies, LAG3 antibodies, TIM-3 antibodies, 41BB antibodies and GITR antibodies.

Yervoy (ipilimumab) is a fully human CTLA-4 antibody marketed by Bristol Myers Squibb. The protein structure of ipilimumab and methods are using are described in U.S. Pat. Nos. 6,984,720 and 7,605,238.

CD134, also known as OX40, is a member of the TNFR-superfamily of receptors which is not constitutively expressed on resting naïve T cells, unlike CD28. OX40 is a secondary costimulatory molecule, expressed after 24 to 72 hours following activation; its ligand, OX40L, is also not expressed on resting antigen presenting cells, but is following their activation. Expression of OX40 is dependent on full activation of the T cell; without CD28, expression of OX40 is delayed and of fourfold lower levels. OX-40 antibodies, OX-40 fusion proteins and methods of using them are disclosed in U.S. Pat. Nos: 7,504,101; 7,758,852; 7,858,765; 7,550,140; 7,960,515; WO2012027328; WO2013028231.

The term "Toll-like receptor" (or "TLR") as used herein refers to a member of the Toll-like receptor family of proteins or a fragment thereof that senses a microbial product and/or initiates an adaptive immune response. In one embodiment, a TLR activates a dendritic cell (DC). Toll-like receptors (TLRs) are a family of pattern recognition receptors that were initially identified as sensors of the innate immune system that recognize microbial pathogens. TLRs recognize distinct structures in microbes, often referred to as "PAMPs" (pathogen associated molecular patterns). Ligand binding to TLRs invokes a cascade of intra-cellular signaling pathways that induce the production of factors involved in inflammation and immunity. In humans, ten TLR have been identified. TLRs that are expressed on the surface of cells include TLR-1, -2, -4, -5, and -6, while TLR-3, -7/8, and -9 are expressed with the ER compartment. Human DC subsets can be identified on the basis of distinct TLR expression patterns. By way of example, the myeloid or "conventional" subset of DC (mDC) expresses TLRs 1-8 when stimulated, and a cascade of activation markers (e.g. CD80, CD86, MHC class I and II, CCR7), pro-inflammatory cytokines, and chemokines are produced. A result of this stimulation and resulting expression is antigen-specific CD4+ and CD8+ T cell priming. These DCs acquire an enhanced capacity to take up antigens and present them in an appropriate form to T cells. In contrast, the plasmacytoid subset of DC (pDC) expresses only TLR7 and TLR9 upon activation, with a resulting activation of NK cells as well as T-cells. As dying tumor cells may adversely affect DC function, it has been suggested that activating DC with TLR agonists may be beneficial for priming anti-tumor immunity in an immunotherapy approach to the treatment of cancer. It has also been suggested that successful treatment of breast cancer using radiation and chemotherapy requires TLR4 activation.

TLR agonists known in the art and finding use in the present invention include, but are not limited to, the following: Pam3Cys, a TLR1/2 agonist; CFA, a TLR2 agonist; MALP2, a TLR2 agonist; Pam2Cys, a TLR2 agonist; FSL-I, a TLR-2 agonist; Hib-OMPC, a TLR-2 agonist; polyribosinic:polyribocytidic acid (Poly I:C), a TLR3 agonist; polyadenosine-polyuridylic acid (poly AU), a TLR3 agonist; Polyinosinic-Polycytidylic acid stabilized with poly-L-lysine and carboxymethylcellulose (Hiltonol), a TLR3 agonist; bacterial flagellin a TLR5 agonist; imiquimod, a TLR7 agonist; resiquimod, a TLR7/8 agonist; loxoribine, a TLR7/8 agonist; and unmethylated CpG dinucleotide (CpG-ODN), a TLR9 agonist.

Additional TLR agonists known in the art and finding use in the present invention further include, but are not limited to aminoalkyl glucosaminide phosphates (AGPs) which bind to the TLR4 receptor are known to be useful as vaccine adjuvants and immunostimulatory agents for stimulating cytokine production, activating macrophages, promoting innate immune response, and augmenting antibody production in immunized animals. An example of a naturally occurring TLR4 agonist is bacterial LPS. An example of a semisynthetic TLR4 agonist is monophosphoryl lipid A (MPL). AGPs and their immunomodulating effects via TLR4 are disclosed in patent publications such as WO 2006/016997, WO 2001/090129, and/or U.S. Pat. No. 6,113,918 and have been reported in the literature. Additional AGP derivatives are disclosed in U.S. Pat. Nos. 7,129,219, 6,525,028 and 6,911,434. Certain AGPs act as agonists of TLR4, while others are recognized as TLR4 antagonist.

In addition to the immunostimulatory agents described above, the compositions of the present invention may further comprise one or more additional substances which, because of their adjuvant nature, can act to stimulate the immune system to respond to the cancer antigens present on the inactivated tumor cell(s). Such adjuvants include, but are not limited to, lipids, liposomes, inactivated bacteria which induce innate immunity (e.g., inactivated or attenuated I/ster/a monocytogenes), compositions which mediate innate immune activation via, (NOD)-like receptors (NLRs), Retinoic acid inducible gene-based (RIG)-l-like receptors (RLRs), and/or C-type lectin receptors (CLRs). Examples of PAMPs include lipoproteins, lipopolypeptides, peptidoglycans, zymosan, lipopolysaccharide, neisserial porins, flagellin, profillin, galactoceramide, muramyl dipeptide. Peptidoglycans, lipoproteins, and lipoteichoic acids are cell wall components of Gram-positive. Lipopolysaccharides are expressed by most bacteria, with MPL being one example. Flagellin refers to the structural component of bacterial flagella that is secreted by pathogenic and commensal bacterial. rt.-Galactosylceramide (rt.-GalCer) is an activator of natural killer T (NKT) cells. Muramyl dipeptide is a bioactive peptidoglycan motif common to all bacteria.

Because of their adjuvant qualities, TLR agonists are preferably used in combinations with other vaccines, adjuvants and/or immune modulators, and may be combined in various combinations. Thus, in certain embodiments, the herein described compounds of Formula (I) that bind to STING and induce STING-dependent TBKI activation and an inactivated tumor cell which expresses and secretes one or more cytokines which stimulate DC induction, recruitment and/or maturation, as described herein can be administered together with one or more TLR agonists for therapeutic purposes.

Additional examples of a further active ingredient or ingredients (anti-neoplastic agent) for use in combination or co-administered with the presently invented compound of Formula (I) are antibodies to ICOS.

CDRs for murine antibodies to human ICOS having agonist activity are shown in PCT/EP2012/055735 (WO 2012/131004). Antibodies to ICOS are also disclosed in WO 2008/137915, WO 2010/056804, EP 1374902, EPI374901, and EP1125585.

Indoleamine 2,3-dioxygenase 1 (IDO1) is a key immunosuppressive enzyme that modulates the anti-tumor immune response by promoting regulatory T cell generation and blocking effector T cell activation, thereby facilitating tumor growth by allowing cancer cells to avoid immune surveillance. (Lemos H, et al., Cancer Res. 2016 Apr. 15; 76(8):2076-81), (Munn D H, et al., Trends Immunol. 2016 March; 37(3):193-207). Further active ingredients (anti-neoplastic agents) for use in combination or co-administered with the presently invented compounds of Formula (I) are IDO inhibitors. Epacadostat, ((Z)—N-(3-bromo-4-fluorophenyl)-N'-hydroxy-4-[2-(sulfamoylamino)ethylamino]-1,2,5-oxadiazole-3-carboxamidine) is a highly potent and selective oral inhibitor of the IDO1 enzyme that reverses tumor-associated immune suppression and restores effective anti-tumor immune responses. Epacadostat is disclosed in U.S. Pat. No. 8,034,953.

Additional examples of a further active ingredient or ingredients (anti-neoplastic agent) for use in combination or co-administered with the presently invented compound of Formula (I) are CD73 inhibitors and A2a and A2b adenosine antagonists.

In one aspect the disease to be treated is an infectious disease, eg caused by bacteria or virus.

In a further aspect of the invention there is provided a compound of Formula (I) or a pharmaceutically acceptable salt thereof for use in the treatment of infectious disease.

In a further aspect there is provided a method of treating infectious disease comprisingadministering to a human in need thereof a therapeutically effective amount of a compoundof Formula (I) or a pharmaceutically acceptable salt thereof.

In a further aspect there is provided the use of a compound of Formula (I) or a pharmaceutically acceptable salt thereof in the manufacture of a medicament for the treatment of infectious disease.

In one embodiment, the compound of the invention may be employed with other therapeutic methods of treating infectious disease. In particular, antiviral and antibacterial agents are envisaged.

The compounds of Formula (I) and pharmaceutically acceptable salts thereof may be used in combination with one or more agents useful in the prevention or treatment of bacterial and viral infections. Examples of such agents include, without limitation; polymerase inhibitors such as those disclosed in WO 2004/037818-A1, as well as those disclosed in WO 2004/037818 and WO 2006/045613; JTK-003, JTK-019, NM-283, HCV-796, R-803, R1728, R1626, as well as those disclosed in WO 2006/018725, WO 2004/074270, WO 2003/095441, US2005/0176701, WO 2006/020082, WO 2005/080388, WO 2004/064925, WO 2004/065367, WO 2003/007945, WO 02/04425, WO 2005/014543, WO 2003/000254, EP 1065213, WO 01/47883, WO 2002/057287, WO 2002/057245 and similar agents; replication inhibitors such as acyclovir, famciclovir, ganciclovir, cidofovir, lamivudine and similar agents; protease inhibitors such as the HIV protease inhibitors saquinavir, ritonavir, indinavir, nelfinavir, amprenavir, fosamprenavir, brecanavir, atazanavir, tipranavir, palinavir, lasinavir, and the HCV protease inhibitors BILN2061, VX-950, $SCH_{503034}$; and similar agents; nucleoside and nucleotide reverse transcriptase inhibitors such as zidovudine, didanosine, lamivudine, zalcitabine, abacavir, stavidine, adefovir, adefovir dipivoxil, fozivudine, todoxil, emtricitabine, alovudine, amdoxovir, elvucitabine, and similar agents; non-nucleoside reverse transcriptase inhibitors (including an agent having anti-oxidation activity such as immunocal, oltipraz etc.) such as nevirapine, delavirdine, efavirenz, loviride, immunocal, oltipraz, capravirine, TMC-278, TMC- 125, etravirine, and similar agents; entry inhibitors such as enfuvirtide (T-20), T-1249, PRO-542, PRO-140, TNX-355, BMS-806, 5-Helix and similar agents; integrase inhibitors such as L-870,180 and similar agents; budding inhibitors such as PA-344 and PA-457, and similar agents; chemokine receptor inhibitors such as vicriviroc (Sch-C), Sch-D, TAK779, maraviroc (UK-427,857), TAK449, as well as those disclosed in WO 02/74769, WO 2004/054974, WO 2004/055012, WO 2004/055010, WO 2004/055016, WO 2004/055011, and WO 2004/054581, and similar agents; neuraminidase inhibitors such as CS-8958, zanamivir, oseltamivir, peramivir and similar agents; ion channel blockers such as amantadine or rimantadine and similar agents; and interfering RNA and antisense oligonucleotides and such as ISIS-14803 and similar agents; antiviral agents of undetermined mechanism of action, for example those disclosed in WO 2005/105761, WO 2003/085375, WO 2006/122011, ribavirin, and similar agents. The compounds of Formula (I) and pharmaceutically acceptable salts thereof may also be used in combination with one or more other agents which may be useful in the prevention or treatment of viral infections for example immune therapies (e.g. interferon or other cytokines/chemokines, cytokine/chemokine receptor modulators, cytokine agonists or antagonists and similar agents); and therapeutic vaccines, antifibrotic agents, anti-inflammatory agents such as corticosteroids or NSAIDs (non-steroidal anti-inflammatory agents) and similar agents.

In a further aspect there is provided a combination comprising a compound of Formula (I) or a pharmaceutically acceptable salt thereof and at least one further therapeutic agent useful in the treatment of infectious disease In a further aspect there is provided a combination comprising a compound of Formula (I) or a pharmaceutically acceptable salt thereof and at least one further therapeutic agent useful in the treatment of infectious diseasefor use in therapy.

In a further aspect there is provided a combination comprising a compound of Formula (I) or pharmaceutically acceptable salt thereof and at least one one further therapeutic agent useful in the treatment of infectious disease, for use in the treatment of infectious disease.

In a further aspect there is provided the use of a combination comprising a compound of Formula (I) or a pharmaceutically acceptable salt thereof and at least one one further therapeutic agent useful in the treatment of infectious diseasein the manufacture of a medicament for the treatment of infectious disease.

In a further aspect there is provided a method of treating infectious disease comprising administering to a human in need thereof a therapeutically effective amount of a combination comprising a compound of Formula (I) or a pharmaceutically acceptable salt thereof and at least one further therapeutic agent useful in the treatment of infectious disease.

In a further aspect there is provided a pharmaceutical composition comprising a combination comprising a compound of Formula (I) or a pharmaceutically acceptable salt thereof and at least one further therapeutic agent useful in the treatment of infectious disease and one or more of pharmaceutically acceptable excipients.

In a further aspect there is provided a composition comprising a compound of Formula (I), or a pharmaceutically acceptable salt thereof, and one or more immunostimulatory agents.

There is also therefore provided an immugenic composition or vaccine adjuvant comprising a compound of Formula (I), or a pharmaceutically acceptable salt thereof.

There is further provided an immugenic composition comprising an antigen or antigen composition and a compound of Formula (I), or a pharmaceutically acceptable salt thereof.

There is further provided a vaccine composition comprising an antigen or antigen composition and a compound of Formula (I), or a pharmaceutically acceptable salt thereof.

There is further provided a method of treating or preventing disease comprising the administration to a human subject suffering from or susceptible to disease, an immugenic composition comprising an antigen or antigen composition and a compound of Formula (I), or a pharmaceutically acceptable salt thereof.

There is further provided a method of treating or preventing disease comprising the administration to a human subject suffering from or susceptible to disease, a vaccine composition comprising an antigen or antigen composition and a compound of Formula (I), or a pharmaceutically acceptable salt thereof.

There is further provided the use of a compound of Formula (I), or a pharmaceutically acceptable salt thereof, for the manufacture of an immugenic composition comprising an antigen or antigen composition, for the treatment or prevention of disease.

There is further provided the use of a compound of Formula (I), or a pharmaceutically acceptable salt thereof, for the manufacture of a vaccine composition comprising an antigen or antigen composition, for the treatment or prevention of disease.

It will be appreciated that the compounds depicted in the application may be drawn using different conventions. For example, the following two compounds are considered equivalent in chemical structure and stereochemistry.

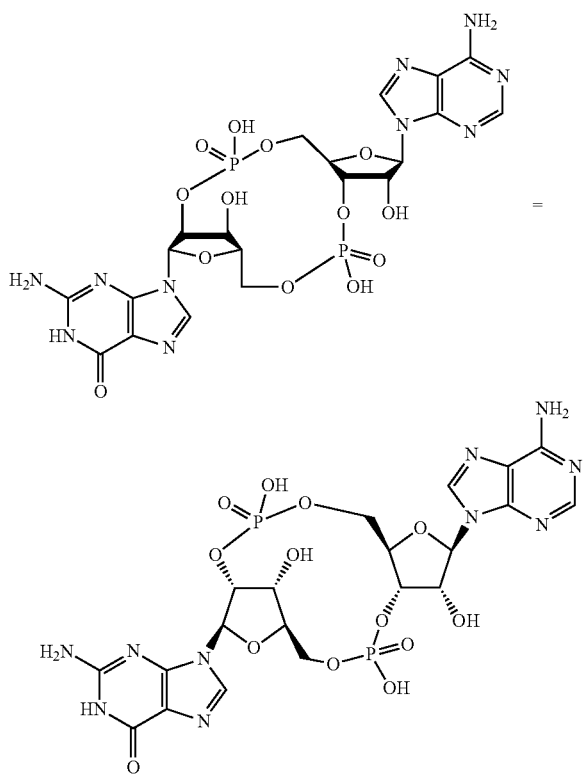

COMPOUND PREPARATION and EXAMPLES

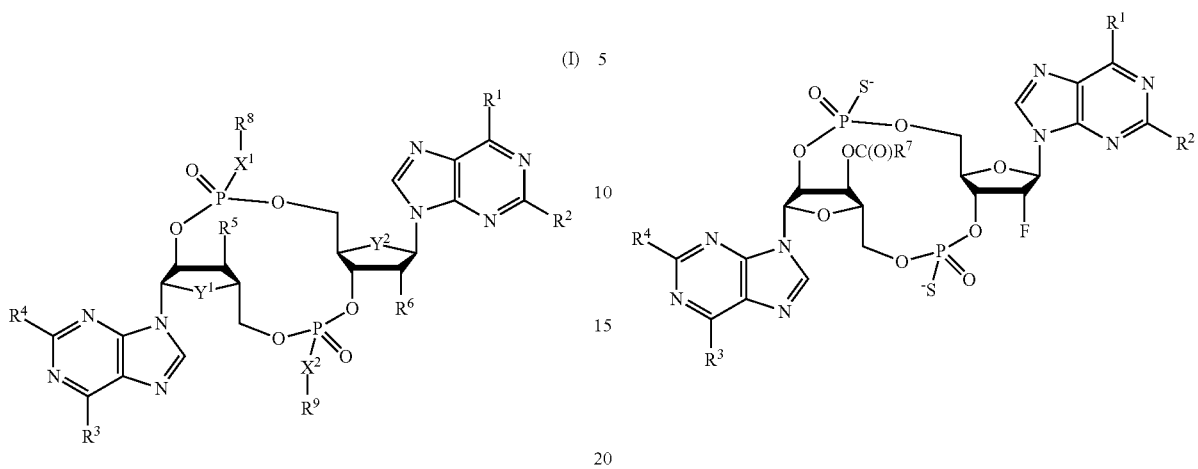

Compounds of Formula (I), where $Y^1$, $Y^2$, $X^1$, $X^2$, $R^1$, $R^2$, $R^3$, $R^4$, $R^5$, $R^6$, $R^8$, and $R^9$ are as defined hereinbefore, may be prepared by methods known in the art of organic synthesis as set forth in the schemes and Examples below. In all of the methods, it is well understood that protecting groups for sensitive or reactive groups may be employed where necessary in accordance with general principles of chemistry. Protecting groups are manipulated according to standard methods of organic synthesis (P. G. M. Wuts and T. W. Green (2007) Greene's Protective Groups in Organic Synthesis, $4^{th}$ edition, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I).

The compounds of Formula (I) and salts thereof may be prepared by the methodology described hereinafter, constituting further aspects of this invention.

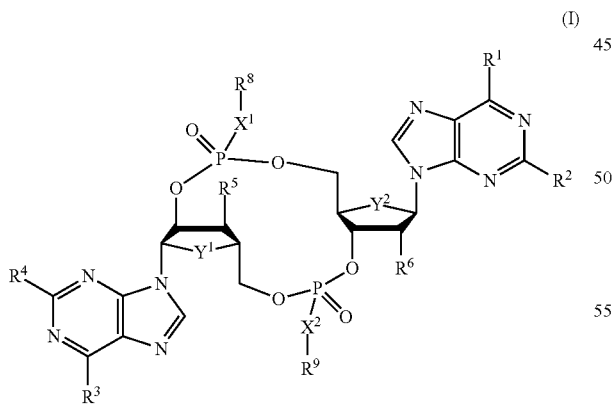

Accordingly, there is provided a process for the preparation of a compound of Formula (I), in which $R^5$ is OC(O)$R^7$ and $R^6$ is F, and both $Y^1$ and $Y^2$ are O, both $X^1$ and $X^2$ are S⁻, as illustrated as formula (IIa), wherein $R^1$, $R^2$, $R^3$ and $R^4$ are as defined hereinbefore for a compound of Formula (I). The process comprises the acylation of a compound of formula (IIIa):

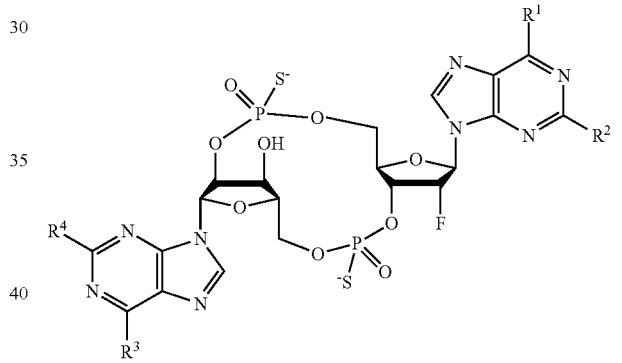

wherein $R^1$, $R^2$, $R^3$, $R^4$ and $R^7$ are as defined hereinbefore for a compound of formula (IIa) and thereafter, if required, preparing a salt of the compound so-formed.

Example 1

A compound of formula (IIIa) and myristic anyhydride in a suitable solvent, for example dimethylformamide (DMF), in the presence of a base such as pyridine, is stirred at room temperature or heated at a suitable temperature, for example 60° C., for a suitable period of time, for example 2-48 hours. The product, of formula (IIa), is isolated by removal of the volatiles and purification if required.

There is also provided a process for the preparation of a compound of Formula (I), in which $R^5$ is OH and $R^6$ is F, and both $Y^1$ and $Y^2$ are O, both $X^1$ and $X^2$ are S, and both $R^8$ and $R^9$ are CH$_2$OC(O)tBu, as illustrated as formula (IVa), wherein $R^1$, $R^2$, $R^3$ and $R^4$ are as defined hereinbefore for a compound of Formula (I). The process comprises the addition of an carbonyloxymethyl group to a compound of formula (IIIa):

(IVa)

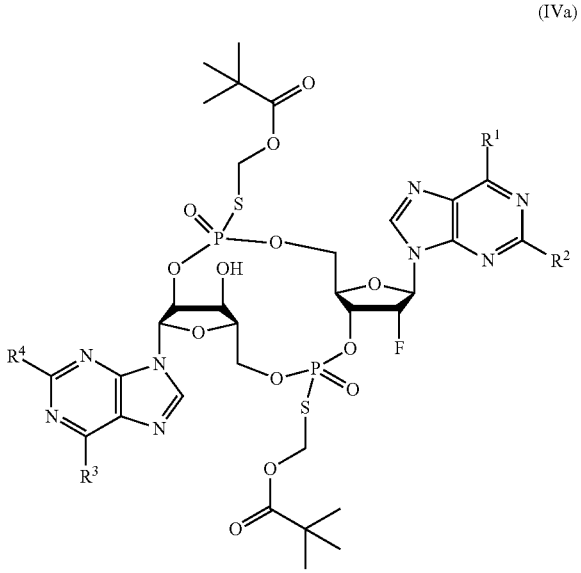

Example 2

A compound of formula (IIIa) and chloromethyl pivalate (POM-Cl) in a suitable solvent, for example dimethylformamide (DMF), in the presence of a base such as Et$_3$N, is stirred at room temperature for a suitable period of time, for example 48 hours. The product, of formula (IVa), is isolated by removal of the volatiles and purification if required.

A compound of formula (IIIa) may be prepared by deprotection of a compound of formula (Va):

(Va)

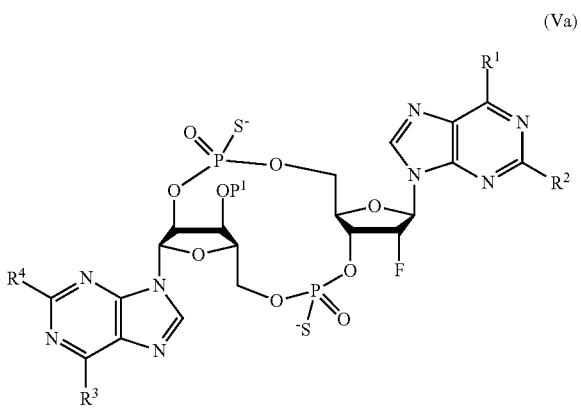

wherein R$^1$, R$^2$, R$^3$ and R$^4$ are as defined hereinbefore for a compound of formula (IIIa) and P$^1$ is a suitable protecting group, such as, tert-butyldimethylsilyloxy (TBDMS) and thereafter, if required, preparing a salt of the compound so-formed.

Example 3

A compound of formula (Va), in a suitable solvent, for example pyridine is heated at a suitable temperature, for example 50° C., then treated with a mixture of triethylamine trihydrofluoride and triethylamine, for a suitable period of time, for example 2-3 hours. The product, of formula (IIIa), is isolated by precipitation by the addition of a solvent, for example acetone, or by removal of the volatiles, and purification if required.

A compound of formula (Va) may be prepared by deprotection of a compound of formula (VIa):

(VIa)

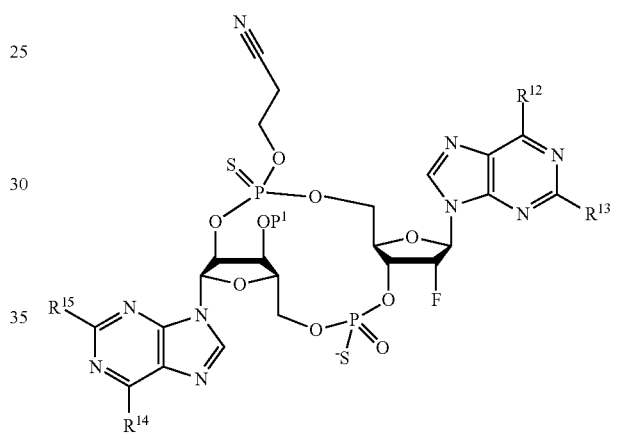

wherein, P$^1$ is a protecting group as defined for compound of formula (Va) and R$^{12}$, R$^{13}$, R$^{14}$ and R$^{15}$ are defined as R$^{12}$ is OH and R$^{13}$ is NHCOiPr, or R$^{12}$ is NHBz and R$^{13}$ is H;

R$^{14}$ is OH and R$^{15}$ is NHCOiPr or R$^{14}$ is NHBz and R$^{15}$ is H;

Example 4

A compound of formula (VIa) is dissolved in a suitable mixture, for example, methylamine in methanol or aqueous ammonia in methanol, and heated at a suitable temperature, for example 50-55° C., for a suitable period of time, for example 2-72 hours. The product, of formula (Va), is isolated by removal of the solvent and purification if required.

A compound of formula (VIa) may be prepared by reaction of a compound of formula (VIIa):

(VIIa)

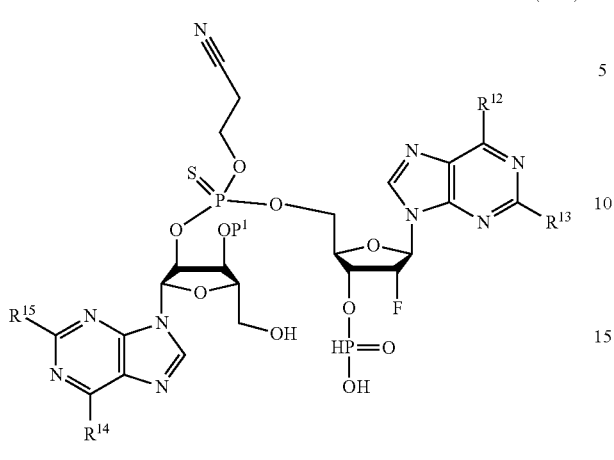

wherein, $P^1$, $R^{12}$, $R^{13}$, $R^{14}$ and $R^{15}$ are defined as hereinbefore for a compound of formula (VIa).

Example 5

A compound of formula (VIIa) is dissolved in a suitable solvent, for example, pyridine, and treated with a suitable coupling reagent, for example, 2-chloro-5,5-dimethyl-1,3,2-dioxaphosphorinane 2-oxide, and stirred at a suitable temperature, for example 20° C., for a suitable period of time, for example 0.5-2 hours. Quenching of the reaction by addition of a suitable solvent, for example water, then after the addition of an sulfurizing agent, for example 3H-benzo[c][1,2]dithiol-3-one, and stirring at a suitable temperature, for example 20° C., for a suitable period of time, for example 5-10 minutes. Quenching of the reaction by addition of a suitable solvent, for example aqueous NaHCO$_3$ solution. Extraction of the product, of formula (VIa), by a suitable organic solvent such as EtOAc. The product, of formula (VIa), is isolated by removal of the solvent and purification if required.

A compound of formula (VIIa) may be prepared by reaction of a compound of formula (VIIIa) with a compound of formula (IXa):

(VIIIa)

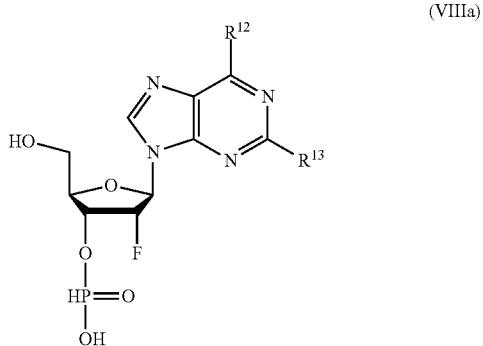

(IXa)

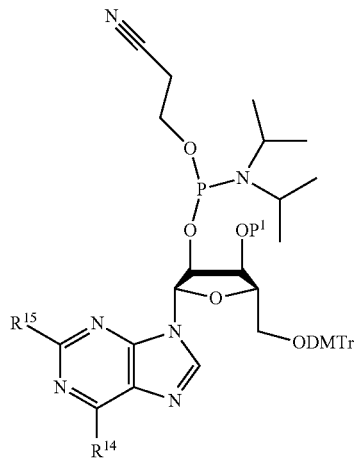

wherein, $P^1$, $R^{12}$, $R^{13}$, $R^{14}$ and $R^{15}$ are defined as hereinbefore for a compound of formula (VIIa) and DMTr is a 4,4-dimethoxytrityl protecting group.

Example 6

A compound of formula (IXa) in a suitable solvent, for example, acetonitrile in the presence of molecular sieves, is treated with a solution of a compound of formula (VIIIa) dissolved in a suitable solvent, for example acetonitrile, and stirred at a suitable temperature, for example 20° C., for a suitable period of time, for example 0.5-2 hours. A solution of a suitable sulfurizing agent, for example N,N-dimethyl-N'-(3-thioxo-3H-1,2,4-dithiazol-5-yl)formimidamide (DDTT), is added and the mixture is stirred at a suitable temperature, for example 20° C., for a suitable period of time, for example 0.5-1 hour. After evaporation of the solvent, the residue is dissolved in a suitable solvent, for example a mixture of dichloromethane and water, and treated with a suitable reagent, for example dichloroacetic acid, and stirred at a suitable temperature, for example 20° C., for a suitable period of time, for example 15 minutes. A solution containing the product, of formula (VIIa), is obtained by the addition of a suitable solvent, for example pyridine, and concentration by evaporation.

A compound of formula (VIIIa) may be prepared by reaction of a compound of formula (Xa).

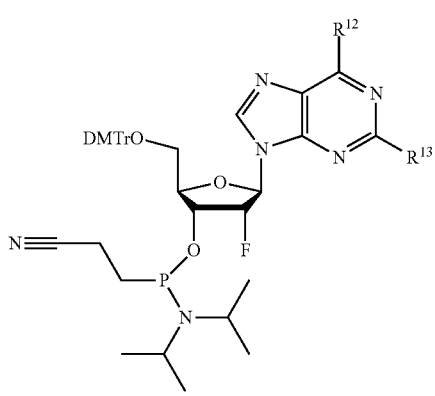

(Xa)

wherein, $R^{12}$ and $R^{13}$ are defined as hereinbefore for a compound of formula (VIIIa) and DMTr is a 4,4-dimethoxytrityl protecting group.

Example 7

A compound of formula (Xa) is dissolved in a suitable mixture, for example, acetonitrile containing water, is treated with pyridinium trifluoroacetate, and stirred at a suitable temperature, for example 20° C., for a suitable period of time, for example 1-5 minutes. Then tert-butylamine is added and the mixture is stirred at a suitable temperature, for example 20° C., for a suitable period of time, for example 10 minutes. The product is isolated by evaporation of the solvent then dissolved in a suitable solvent, for example dichloromethane containing water, and treated with dichloroacetic acid and stirred at a suitable temperature, for example 20° C., for a suitable period of time, for example 15 minutes. A concentrated solution of the product, of formula (VIIIa), in acetonitrile is obtained by the addition of pyridine followed by azeotroping the mixture with anhydrous acetonitrile.

Phosphoramidites of formula (IXa) and (Xa) are either known in the literature, or are commercially available from suppliers such as Sigma, Chemgenes and CarboSynth or may be prepared by known methods.

Example 8

Compound 1b (1R,6R,8R,9R,10R,15R,17R,18R)-8,17-bis(6-amino-9H-purin-9-yl)-9-fluoro-18-hydroxy-3,12-disulfanyl-2,4,7,11,13,16-hexaoxa-3λ$^5$,12λ$^5$-diphosphatricyclo[13.2.1.0$^{6,10}$]octadecane-3,12-dione, bisammonium salt

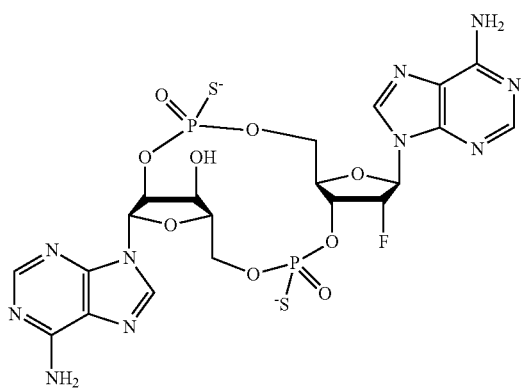

1b

Intermediate 1

(2R,3R,4R,5R)-5-(6-benzamido-9H-purin-9-yl)-2-((bis(4-methoxyphenyl)(phenyl)methoxy)methyl)-4-fluorotetrahydrofuran-3-yl hydrogen phosphonate

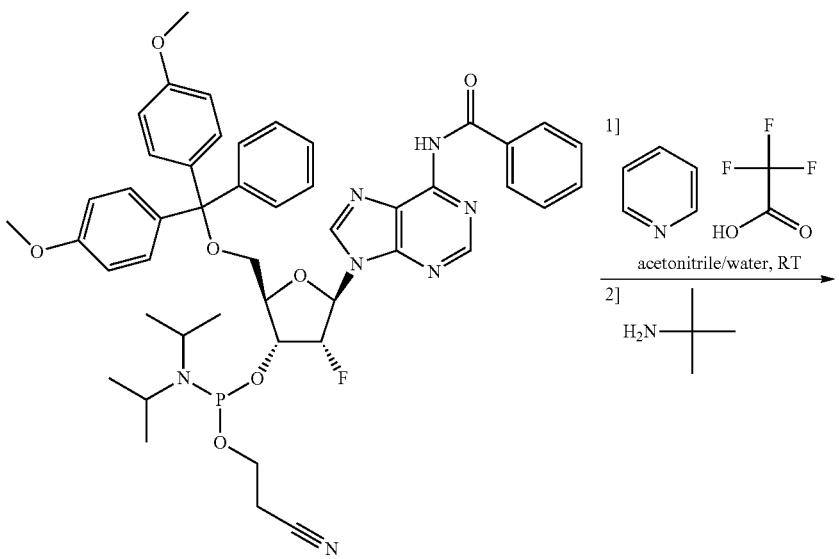

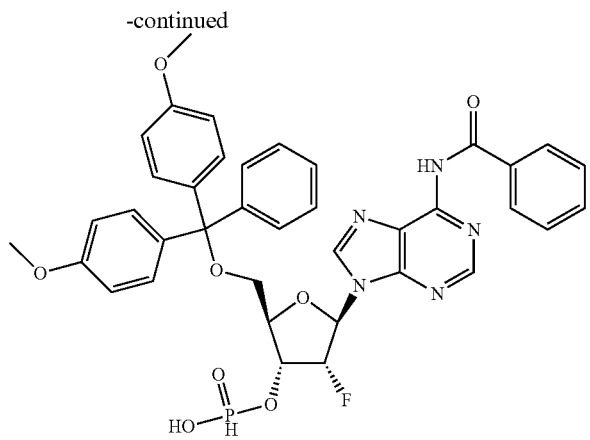

To a solution of (2R,3R,4R,5R)-5-(6-benzamido-9H-purin-9-yl)-2-((bis(4-methoxyphenyl)(phenyl)methoxy)methyl)-4-fluorotetrahydrofuran-3-yl (2-cyanoethyl) diisopropylphosphoramidite (2190 mg, 2.5 mmol) in acetonitrile (15 mL) and water (0.090 mL, 5.00 mmol) at room temperature was added pyridine 2,2,2-trifluoroacetate (579 mg, 3.00 mmol). The mixture was stirred for 1 minute, after which time LCMS indicated complete conversion to the first intermediate, m/z (M+H)=793.3. Then, 2-methylpropan-2-amine (13.14 mL, 125 mmol) was added and the mixture stirred for 10 minutes, after which time LCMS indicated consumption of the first formed intermediate.

The mixture was concentrated in vacuo to afford a white foam. The foam was then dissolved in acetonitrile (20 mL) and concentrated. This process was repeated one more time. The crude material was dissolved in dichloromethane (10 mL) and purified by chromatography in two batches (silica gel, gradient elution of 0-30% methanol in dichloromethane). The desired fractions were combined and evaporated to afford two separate white solids which were then dissolved in dichloromethane, combined and evaporated to afford the titled compound (780 mg, 1.055 mmol, 42.2% yield) as a white solid. LCMS m/z 740.4 (M+H).

Intermediate 2

(2R,3R,4R,5R)-5-(6-benzamido-9H-purin-9-yl)-4-fluoro-2-(hydroxymethyl)tetrahydrofuran-3-yl hydrogen phosphonate Intermediate 2 was made generally according to the procedure below. Slight modifications, for example those depicted for Intermediate 2 in other Examples, may be used.

To a solution of (2R,3R,4R,5R)-5-(6-benzamido-9H-purin-9-yl)-2-((bis(4-methoxyphenyl)(phenyl)methoxy)methyl)-4-fluorotetrahydrofuran-3-yl hydrogen phosphonate (775 mg, 1.048 mmol) in dichloromethane (20 mL) and water (0.189 mL, 10.48 mmol) at room temperature was added 2,2-dichloroacetic acid (0.655 mL, 8.38 mmol). The mixture was stirred at room temperature for 30 minutes.

The reaction was then quenched by addition of pyridine (1.356 mL, 16.76 mmol) and concentrated in vacuo to afford a colorless oil. The material was stored under nitrogen at 4° C. After storing at 4° C., the material solidified to afford the impure titled compound as a waxy, white solid, which was used without further purification. LCMS m/z 438.3 (M+H).

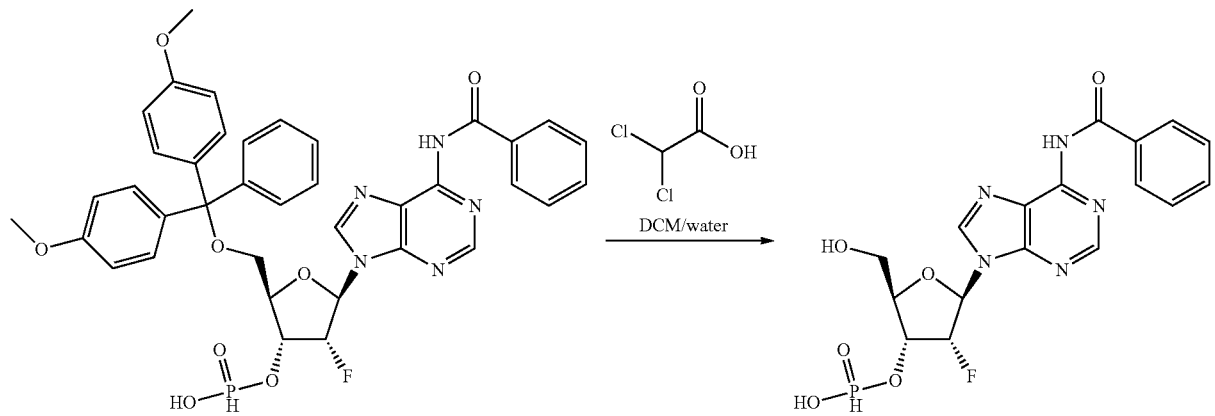

Intermediate 3

(2R,3R,4R,5R)-5-(6-benzamido-9H-purin-9-yl)-2-((((((2R,3R,4R,5R)-2-(6-benzamido-9H-purin-9-yl)-4-((tert-butyldimethylsilyl)oxy)-5-(hydroxymethyl)tetrahydrofuran-3-yl)oxy)(2-cyanoethoxy)phosphorothioyl)oxy)methyl)-4-fluorotetrahydrofuran-3-yl hydrogen phosphonate

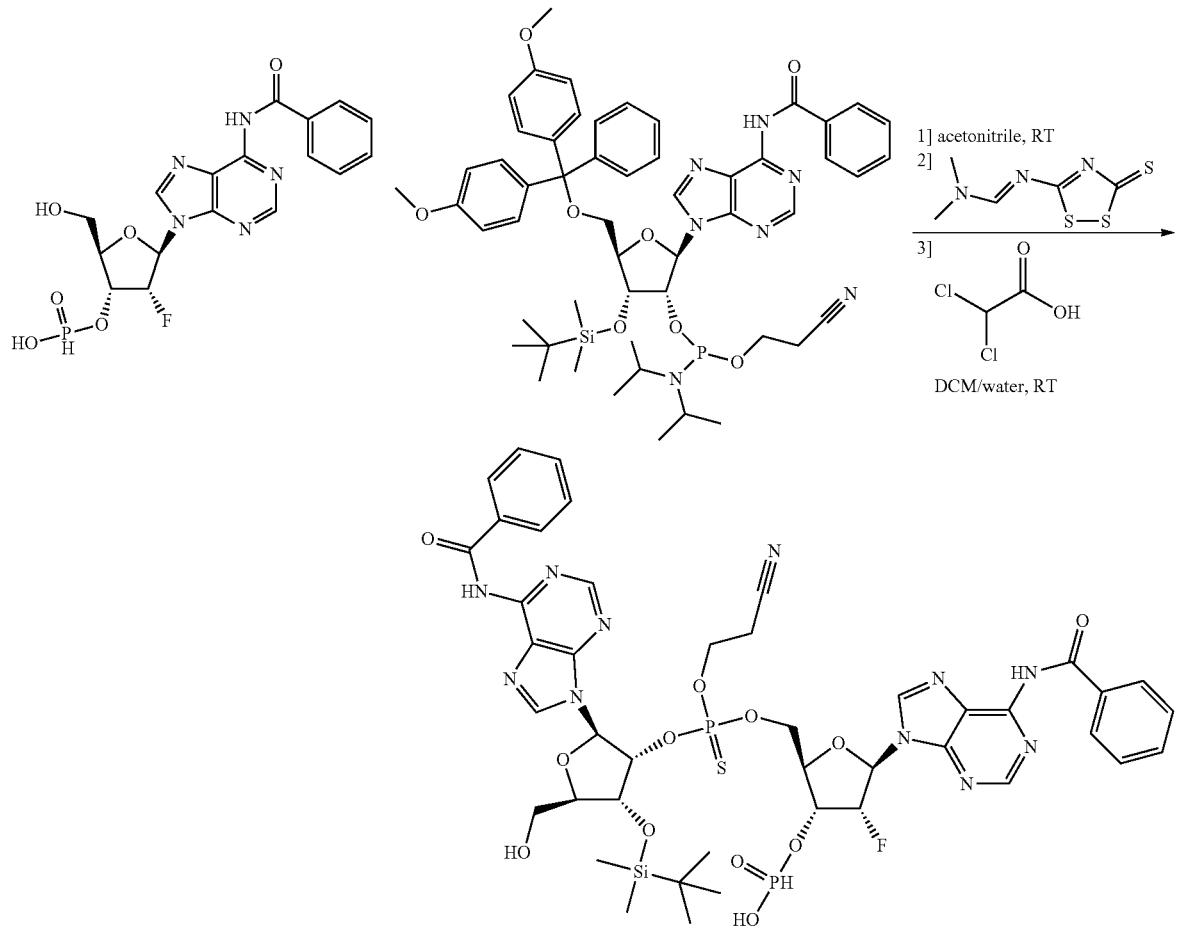

Intermediate 3 was made generally according to the procedure below. Slight modifications, for example those depicted for Intermediate 3 in other Examples, may be used.

The impure solid (2R,3R,4R,5R)-5-(6-benzamido-9H-purin-9-yl)-4-fluoro-2-(hydroxymethyl)tetrahydrofuran-3-yl hydrogen phosphonate (458 mg, 1.047 mmol) obtained above was azeotroped with anhydrous acetonitrile (3×20 mL). After the last concentration, ~10 mL of acetonitrile was kept in the flask. At room temperature, (2R,3R,4R,5R)-2-(6-benzamido-9H-purin-9-yl)-5-((bis(4-methoxyphenyl)(phenyl)methoxy)methyl)-4-((tert-butyldimethylsilyl)oxy)tetrahydrofuran-3-yl (2-cyanoethyl) diisopropylphosphoramidite (1345 mg, 1.361 mmol) was dried by azeotroping with anhydrous acetonitrile (3×20 mL). After the last concentration, ~5 mL of acetonitrile was kept in the flask, and 3 Å molecular sieves (~40 beads) were added. The solution was left standing over the molecular sieves at room temperature for 1 hour.

To the dried suspension of (2R,3R,4R,5R)-5-(6-benzamido-9H-purin-9-yl)-4-fluoro-2-(hydroxymethyl)tetrahydrofuran-3-yl hydrogen phosphonate (458 mg, 1.047 mmol) in acetonitrile (10 mL) at room temperature under a nitrogen atmosphere was added the pre-dried solution of (2R,3R,4R,5R)-2-(6-benzamido-9H-purin-9-yl)-5-((bis(4-methoxyphenyl)(phenyl)methoxy)methyl)-4-((tert-butyldimethylsilyl)oxy)tetrahydrofuran-3-yl (2-cyanoethyl) diisopropylphosphoramidite (1345 mg, 1.361 mmol) in acetonitrile (5 mL) via syringe. The solution went from being orange to light yellow. The mixture was stirred under a nitrogen atmosphere at room temperature for 1 hour, after which time LCMS indicated minimal remaining starting material. Then, (E)-N,N-dimethyl-N'-(3-thioxo-3H-1,2,4-dithiazol-5-yl)formimidamide (237 mg, 1.152 mmol) was added to the reaction mixture and the mixture was stirred at room temperature for 30 minutes. The solvent was evaporated in vacuo, and the residue was taken into dichloromethane (40 mL) and water (0.189 mL, 10.47 mmol), followed by the addition of 2,2-dichloroacetic acid (1.037 mL, 12.57 mmol). The mixture was stirred at room temperature for 10 minutes, after which time LCMS indicated the formation of desired product. The reaction was quenched with pyridine (10 mL, 124 mmol), then the mixture was concentrated in vacuo to afford the impure titled compound as an orange oil. LCMS: m/z 1054 (M+H). The product was stored under nitrogen at 4° C. and used in the following step without further purification.

67

Intermediate 4

N-{9-[(1R,6R,8R,9R,10R,15R,17R,18R)-17-(6-benzamido-9H-purin-9-yl)-18-[(tert-butyldimethylsilyl)oxy]-3-(2-cyanoethoxy)-9-fluoro-12-oxo-12-sulfanyl-3-sulfanylidene-2,4,7,11,13,16-hexaoxa-3$\lambda^5$,12$\lambda^5$-diphosphatricyclo[13.2.1.0$^{6,10}$]octadecan-8-yl]-9H-purin-6-yl}benzamide

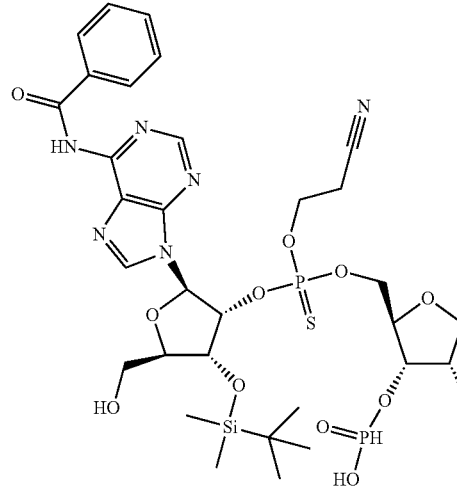

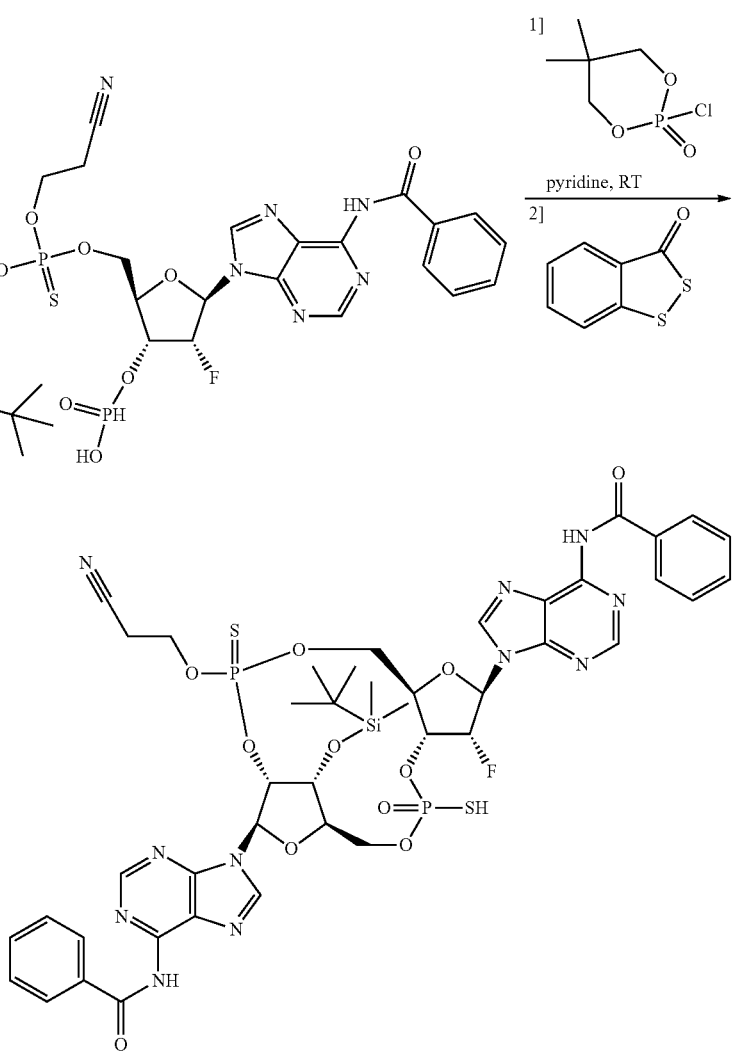

A solution of crude (2R,3R,4R,5R)-5-(6-benzamido-9H-purin-9-yl)-2-((((((2R,3R,4R,5R)-2-(6-benzamido-9H-purin-9-yl)-4-((tert-butyldimethylsilyl)oxy)-5-(hydroxymethyl)tetrahydrofuran-3-yl)oxy)(2-cyanoethoxy)phosphorothioyl)oxy)methyl)-4-fluorotetrahydrofuran-3-yl hydrogen phosphonate (1104 mg, 1.047 mmol) in pyridine (~20 mL) and evaporated, then redissolved in pyridine (20 mL) and concentrated to approximately 10 mL. To this solution under nitrogen was added 2-chloro-5,5-dimethyl-1,3,2-dioxaphosphinane 2-oxide (677 mg, 3.67 mmol) in one portion. The reaction mixture was stirred at room temperature under nitrogen for 30 minutes, after which time LCMS indicated consumption of starting material, then the reaction was quenched by the addition of water (0.660 mL,

68

36.7 mmol). 3H-Benzo[c][1,2]dithiol-3-one (264 mg, 1.571 mmol) was then added, and the mixture stirred at room temperature for 5 minutes before being poured onto a solution of water (160 mL) containing sodium bicarbonate (4400 mg, 52.4 mmol). This mixture was stirred for 5 minutes, then EtOAc (150 mL) was added, and the mixture stirred for a further 10 minutes. The solution was transferred to a separating funnel, and the aqueous layer was separated from the organic. The aqueous layer was further extracted with EtOAc (150 mL), then the combined organic layers were dried (Na$_2$SO$_4$), filtered and evaporated in vacuo to an orange oil. The material was stored under nitrogen at 4° C. overnight.

After warming to room temperature, the crude material was diluted with toluene (20 mL) and evaporated to remove excess pyridine. The crude product was purified by chromatography (silica gel, ISCO Teledyne Gold, 80 g) Gradient elution was run from 0-10% methanol in dichloromethane over 15 minutes followed by a 5 minute isocratic hold at 10% methanol in dichloromethane. Then the gradient increased from 10-20% methanol in dichloromethane over 15 minutes followed by a 10 minute isocratic hold at 20% methanol in dichloromethane. The desired fractions were combined and evaporated in vacuo to afford the titled compound (570 mg, 0.342 mmol, 32.6% yield) as a yellow solid.

Four isomers were observed by LCMS [m/z 1068.5 (M+H)] in an approximate ratio of 8:4:2:1 with retention times of 1.13, 1.23, 1.18 and 1.08 minutes, respectively. The product was stored under nitrogen at 4° C. and used in the following step without further purification.

Intermediate 5

(1R,6R,8R,9R,10R,15R,17R,18R)-8,17-bis(6-amino-9H-purin-9-yl)-18-[(tert-butyldimethylsilyl)oxy]-9-fluoro-3,12-disulfanyl-2,4,7,11,13,16-hexaoxa-3$\lambda^5$, 12$\lambda^5$-diphosphatricyclo[13.2.1.0$^{6,10}$]octadecane-3, 12-dione, bisammonium salt 9H-purin-6-yl}benzamide (570 mg, 0.534 mmol) in methylamine (33 wt % in ethanol) (25 mL, 201 mmol) was stirred at room temperature for 50 minutes, after which time LCMS indicated consumption of starting materials. The reaction mixture was concentrated in vacuo to an orange residue. The material was stored under nitrogen at 4° C. overnight.

The material was allowed to warm to room temperature and dissolved in methanol/DMSO (4 mL total). A portion was purified using reverse phase HPLC (10-90% acetonitrile:water (with 0.1% NH$_4$OH modifier), C18 50×30 mm Gemini column, 47 mL/min, 8 minute gradient, UV collection=214 nm).

Another portion was purified using reverse phase HPLC (10-50% acetonitrile:water (with 0.1% NH$_4$OH modifier), C18 50×30 mm Gemini column, 47 mL/min, 8 minute gradient, UV collection=214 nm).

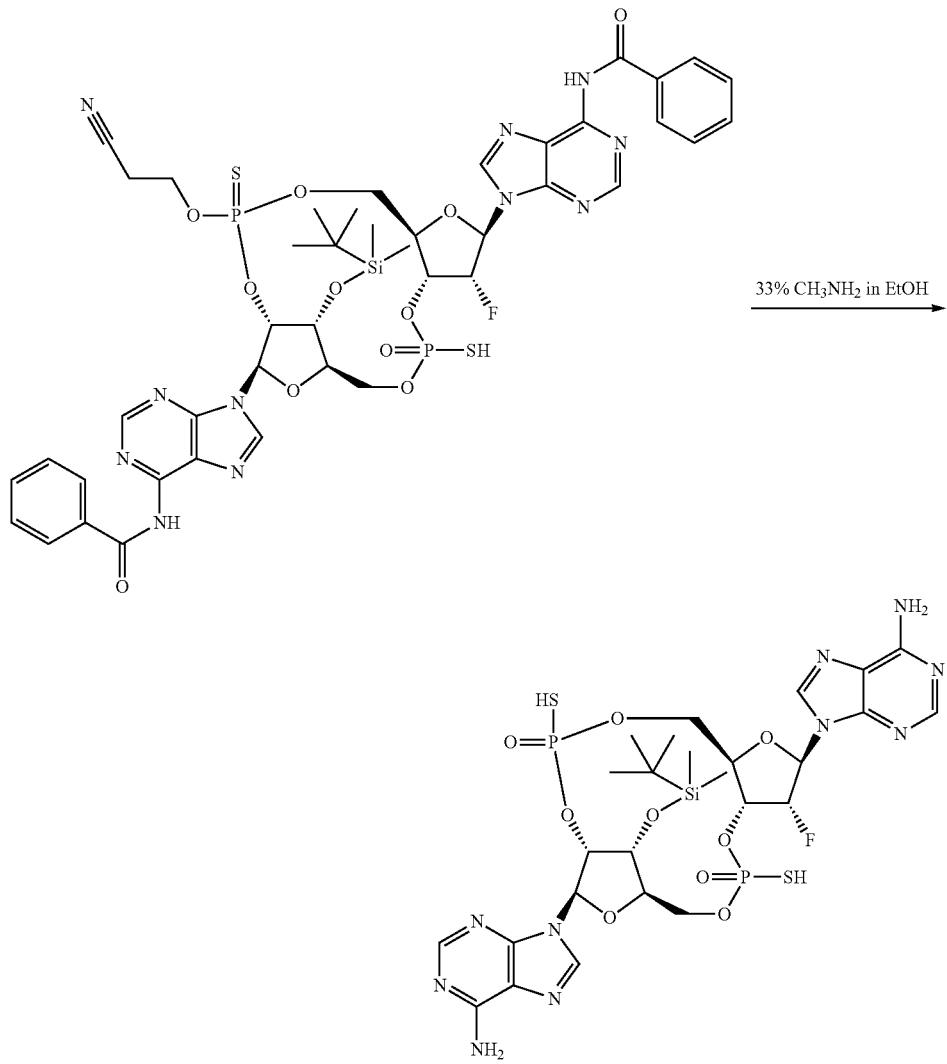

A solution of above obtained N-{9-[(1R,6R,8R,9R,10R,15R,17R,18R)-17-(6-benzamido-9H-purin-9-yl)-18-[(tert-butyldimethylsilyl)oxy]-3-(2-cyanoethoxy)-9-fluoro-12-oxo-12-sulfanyl-3-sulfanylidene-2,4,7,11,13,16-hexaoxa-3$\lambda^5$,12$\lambda^5$-diphosphatricyclo[13.2.1.0$^{6,10}$]octadecan-8-yl]-

Fractions from the two purifications were combined and concentrated to afford three isomeric products:

Isomer 1 of the titled compound as a bisammonium salt, with the exact stereochemistry at two phosphorus centers undetermined (6 mg, purity by LCMS =70%; 4.99

μmol, 0.936% yield) as an off-white gum, LCMS m/z 807.2 (M+H), $t_{RET}$=0.68 min.

Isomer 2 of the titled compound as a bisammonium salt, with the exact stereochemistry at two phosphorus centers undetermined (64 mg, purity by LCMS =22%, 0.017 mmol, 3.14% yield) as a colorless gum, LCMS m/z 807.2 (M+H), tRET=0.80 min.

Isomer 3 of the titled compound as a bisammonium salt, with the exact stereochemistry at two phosphorus centers undetermined (26 mg, purity by LCMS =50%, 0.015 mmol, 2.90% yield) as a white solid, LCMS m/z 807.2 (M+H), $t_{RET}$=0.92 min.

The latest eluting isomer, Isomer 3 of the titled compound, was the major product as determined by area under the chromatography peak (UV @ 214 nm) and was used in the following deprotection step.

Example 8

(1R,6R,8R,9R,10R,15R,17R,18R)-8,17-bis(6-amino-9H-purin-9-yl)-9-fluoro-18-hydroxy-3,12-disulfanyl-2,4,7,11,13,16-hexaoxa-3λ$^5$,12λ$^5$-diphosphatricyclo[13.2.1.0$^{6,10}$]octadecane-3,12-dione, bisammonium salt

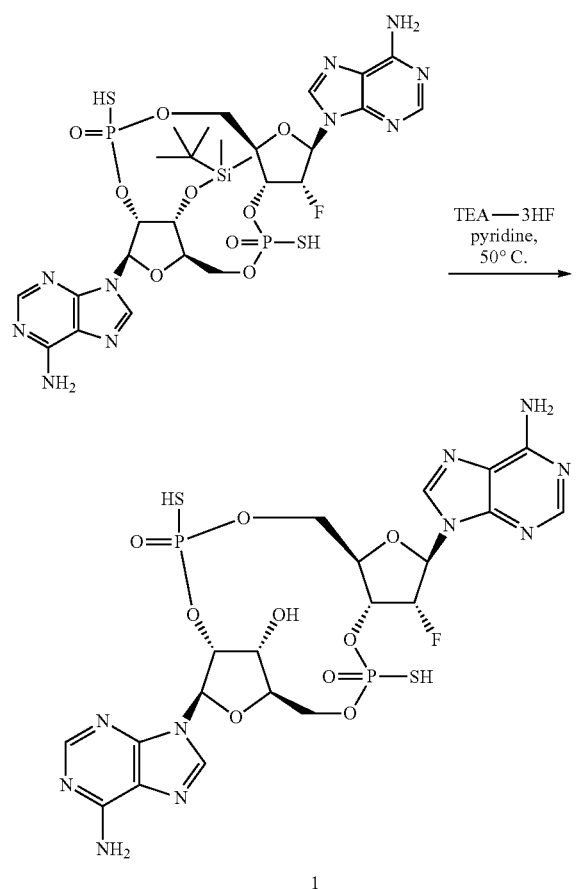

Isomer 3 of (1R,6R,8R,9R,10R,15R,17R,18R)-8,17-bis(6-amino-9H-purin-9-yl)-18-[(tert-butyldimethylsilyl)oxy]-9-fluoro-3,12-disulfanyl-2,4,7,11,13,16-hexaoxa-3λ$^5$,12λ$^5$-diphosphatricyclo[13.2.1.0$^{6,10}$]octadecane-3,12-dione (25 mg, 0.031 mmol) obtained from the preceding step was suspended in pyridine (0.5 mL) and triethylamine (0.5 mL). The mixture was stirred and heated to 50° C., then triethylamine trihydrofluoride (0.5 mL, 3.07 mmol) was added and the mixture was stirred at 50° C. for a further 2 hours by which time LCMS indicated the complete consumption of starting material and conversion to the desired product.

The mixture was allowed to cool to room temperature, then acetone (~10 mL) was added and the solvent evaporated and the material stored under nitrogen at 4° C. overnight.

The crude residue was purified using reverse phase HPLC (0-20% acetonitrile in water (0.1% NH$_4$OH), 50×30 mm Gemini column, 47 mL/min, 8 minute gradient, UV detection @ 214 nm). The desired fractions were combined and evaporated to afford the titled compound as a bisammonium salt (2.3 mg) as a single diastereomer, with the exact stereochemistry at two phosphorus centers undetermined. The product was a white solid. LCMS m/z 693.1 (M+H).

$^1$H NMR (600 MHz, DMSO-d$_6$ with one drop of D$_2$O): δ ppm 8.69 (s, 1H), 8.33 (s, 1H), 8.14-8.17 (m, 1H), 8.12 (br s, 1H), 6.24 (br dd, J=14.5, 3.2 Hz, 1H), 6.08 (br d, J=8.3 Hz, 1H), 5.71-5.86 (m, 1H), 5.22 (br t, J=8.7 Hz, 2H), 4.49-4.54 (m, 1H), 4.32 (br s, 1H), 4.16 (br s, 1H), 4.08-4.15 (m, 2H), 4.03-4.06 (m, 1H), 4.00-4.03 (m, 1H), 3.73 (br s, 1H).

$^{13}$C NMR (150 MHz, DMSO-d$_6$ with one drop of D$_2$O): δ ppm 156.1, 155.9, 153.2, 152.9, 150.4, 149.1, 119.1, 118.4, 90.6, 85.3, 83.6, 83.0, 80.6, 77.7, 71.6, 71.1, 67.2, 63.3.

$^{31}$P NMR (162 MHz, DMSO-d$_6$ with one drop of D$_2$O) δ ppm 53.84 and 49.04.

It is noted that Example 8 produced Compound 1b-Isomer 2. Because of the small scale of the reaction, no Compound 1a-Isomer 1 was isolated. Both Isomer 1 and Isomer 2 of Compound 1 are prepared in Examples 8a and 8b below.

Examples 8a and 8b

Compounds 1a and 1b (1R,6R,8R,9R,10R,15R,17R,18R)-8,17-bis(6-amino-9H-purin-9-yl)-9-fluoro-18-hydroxy-3,12-disulfanyl-2,4,7,11,13,16-hexaoxa-3λ$^5$,12λ$^5$-diphosphatricyclo[13.2.1.0$^{6,10}$]octadecane-3,12-dione, bisammonium salt

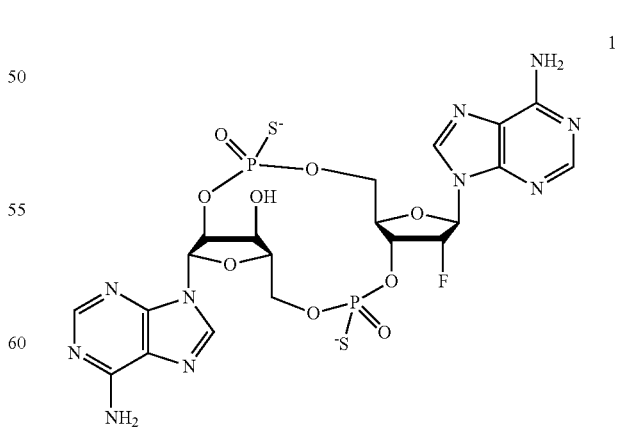

1a - Isomer 1
1b - Isomer 2

Intermediate 1

(2R,3R,4R,5R)-5-(6-benzamido-9H-purin-9-yl)-2-((bis(4-methoxyphenyl)(phenyl)methoxy)methyl)-4-fluorotetrahydrofuran-3-yl hydrogen phosphonate

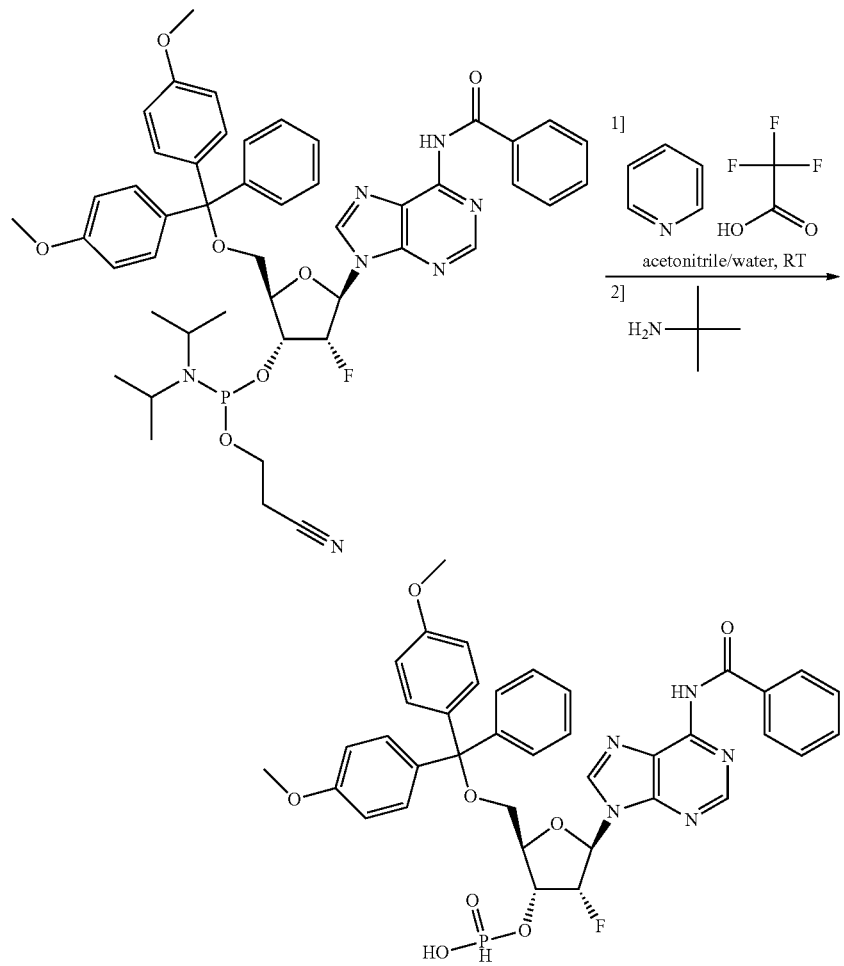

To a solution of (2R,3R,4R,5R)-5-(6-benzamido-9H-purin-9-yl)-2-((bis(4-methoxyphenyl)(phenyl)methoxy)methyl)-4-fluorotetrahydrofuran-3-yl (2-cyanoethyl) diisopropylphosphoramidite (10 g, 11.42 mmol) in acetonitrile (65 mL) and water (0.411 mL, 22.83 mmol) at room temperature was added pyridine 2,2,2-trifluoroacetate (2.65 g, 13.70 mmol). The mixture was stirred for 1 minute, after which time LCMS indicated complete conversion to the first intermediate m/z 793.7 (M+H). Then, 2-methylpropan-2-amine (60.0 mL, 571 mmol) was added and the mixture stirred for 15 minutes, after which time LCMS indicated consumption of the first formed intermediate.

The mixture was concentrated in vacuo to a white foam. The foam was then dissolved in acetonitrile and concentrated (50 mL). This process was repeated one more time. The crude material was dissolved in dichloromethane and purified by chromatography (silica gel, ISCO RediSep, 120 g silica) eluted with a gradient of 0-30% methanol in dichloromethane. The desired fractions were combined and evaporated in vacuo to afford the titled compound (4.8 g, 6.49 mmol, 56.8% yield) as a white solid. LCMS m/z 740.3 (M+H).

Intermediate 2

(2R,3R,4R,5R)-5-(6-benzamido-9H-purin-9-yl)-4-fluoro-2-(hydroxymethyl)tetrahydrofuran-3-yl hydrogen phosphonate

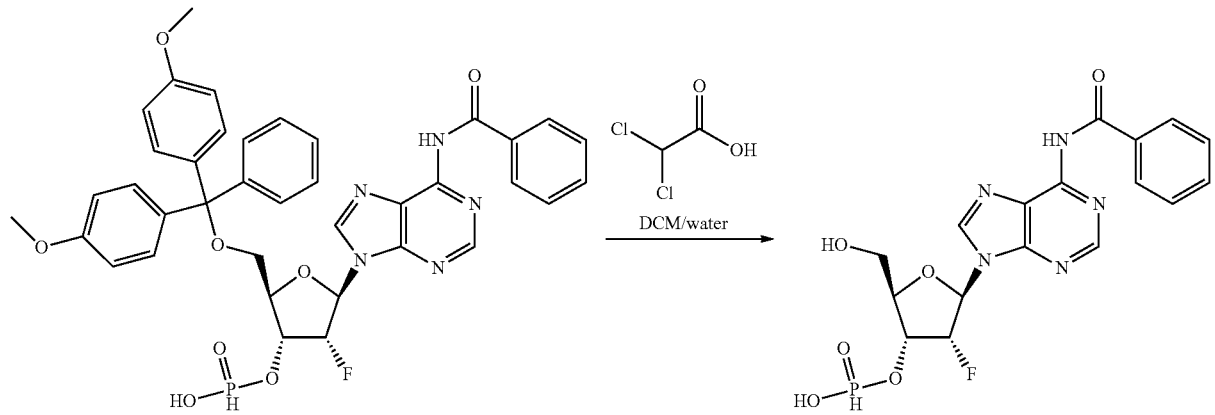

Intermediate 2 was made generally according to the procedure below. Slight modifications, for example those depicted for Intermediate 2 in other Examples, may be used.

To a solution of (2R,3R,4R,5R)-5-(6-benzamido-9H-purin-9-yl)-2-((bis(4-methoxyphenyl)(phenyl)methoxy)methyl)-4-fluorotetrahydrofuran-3-yl hydrogen phosphonate (4.8 g, 6.49 mmol) in dichloromethane (100 mL) and water (1.169 mL, 64.9 mmol) at room temperature was added 2,2-dichloroacetic acid (4.06 mL, 51.9 mmol). The mixture was stirred at room temperature for 30 minutes. The reaction was then quenched with pyridine (8.40 mL, 104 mmol) and concentrated in vacuo to afford the impure titled compound as a colorless oil. The material was used as is immediately in the next step. A final mass was not determined. LCMS m/z 438.3 (M+H).

Intermediate 3

(2R,3R,4R,5R)-5-(6-benzamido-9H-purin-9-yl)-2-(((((2R,3R,4R,5R)-2-(6-benzamido-9H-purin-9-yl)-4-((tert-butyldimethylsilyl)oxy)-5-(hydroxymethyl)tetrahydrofuran-3-yl)oxy)(2-cyanoethoxy)phosphorothioyl)oxy)methyl)-4-fluorotetrahydrofuran-3-yl hydrogen phosphonate

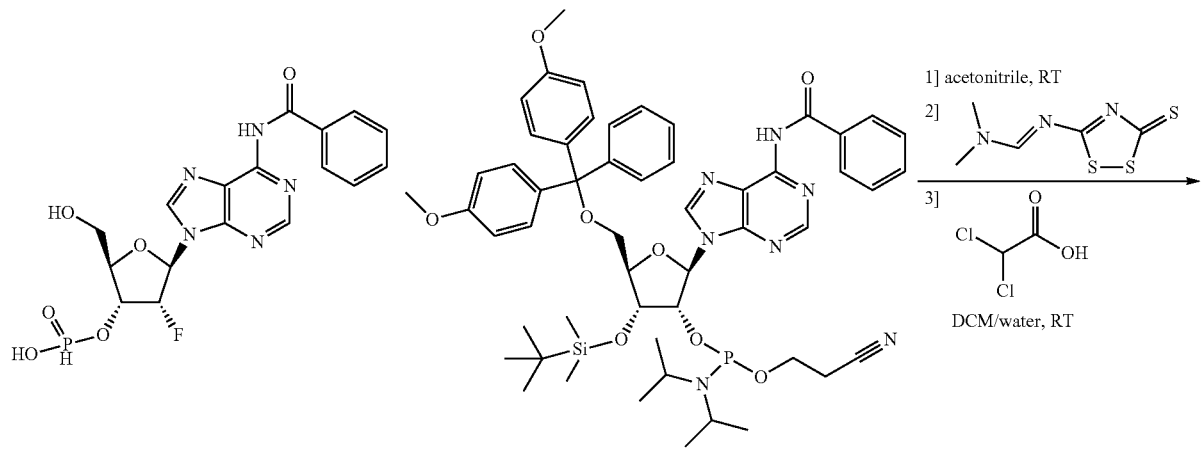

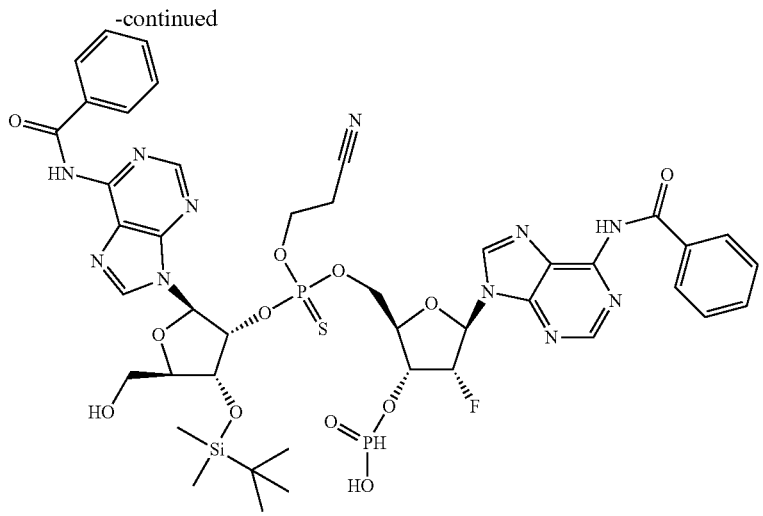

Intermediate 3 was made generally according to the procedure below. Slight modifications, for example those depicted for Intermediate 2 in other Examples, may be used.

The impure solid (2R,3R,4R,5R)-5-(6-benzamido-9H-purin-9-yl)-4-fluoro-2-(hydroxymethyl)tetrahydrofuran-3-yl hydrogen phosphonate (2.84 g, 6.49 mmol) obtained above was azeotroped with anhydrous acetonitrile (3×60 mL). After the last concentration, ~20 mL of acetonitrile was kept in the flask. At room temperature, (2R,3R,4R,5R)-2-(6-benzamido-9H-purin-9-yl)-5-((bis(4-methoxyphenyl)(phenyl)methoxy)methyl)-4-((tert-butyldimethylsilyl)oxy)tetrahydrofuran-3-yl (2-cyanoethyl) diisopropylphosphoramidite (8.00 g, 8.10 mmol) was dried by azeotroping with anhydrous acetonitrile (3×60 mL). After the last concentration, ~30 mL of acetonitrile was kept in the flask, and 3 Å molecular sieves (~40 beads) were added. The solution was left standing over the molecular sieves at room temperature for 1 hour.

To the dried suspension of (2R,3R,4R,5R)-5-(6-benzamido-9H-purin-9-yl)-4-fluoro-2-(hydroxymethyl)tetrahydrofuran-3-yl hydrogen phosphonate (2.84 g, 6.49 mmol) in acetonitrile (40 mL) at room temperature under a nitrogen atmosphere was added the pre-dried solution of (2R,3R,4R,5R)-2-(6-benzamido-9H-purin-9-yl)-5-((bis(4-methoxyphenyl)(phenyl)methoxy)methyl)-4-((tert-butyldimethylsilyl)oxy)tetrahydrofuran-3-yl (2-cyanoethyl) diisopropylphosphoramidite (8.00 g, 8.10 mmol) in acetonitrile (30 mL) via syringe. The mixture was stirred under a nitrogen atmosphere at room temperature for 1 hour, after which time LCMS indicated minimal remaining starting material. Then, (E)-N,N-dimethyl-N'-(3-thioxo-3H-1,2,4-dithiazol-5-yl)formimidamide (1.467 g, 7.14 mmol) was added to the reaction mixture, and the mixture was stirred at room temperature for 45 minutes. The solvent was evaporated in vacuo, and the residue was taken into dichloromethane (100 mL) and water (1.170 mL, 64.9 mmol), followed by the addition of 2,2-dichloroacetic acid (6.43 mL, 78 mmol). The mixture was stirred at room temperature for 10 minutes, after which time LCMS indicated the formation of desired product. The reaction was quenched with pyridine (12.61 mL, 156 mmol), then the mixture was concentrated in vacuo to afford the impure titled compound as an orange oil. LCMS indicated the formation of two isomers with two overlaping peaks between 0.98-1.04 min. The material was immediately taken on in the next step as is. A final sample mass was not determined. LCMS m/z 1054.6 (M+H).

Intermediate 4

N-{9-[(1R,6R,8R,9R,10R,15R,17R,18R)-17-(6-benzamido-9H-purin-9-yl)-18-[(tert-butyldimethylsilyl)oxy]-3-(2-cyanoethoxy)-9-fluoro-12-oxo-12-sulfanyl-3-sulfanylidene-2,4,7,11,13,16-hexaoxa-3λ$^5$,12λ$^5$-diphosphatricyclo[13.2.1.0$^{6,10}$]octadecan-8-yl]-9H-purin-6-yl}benzamide

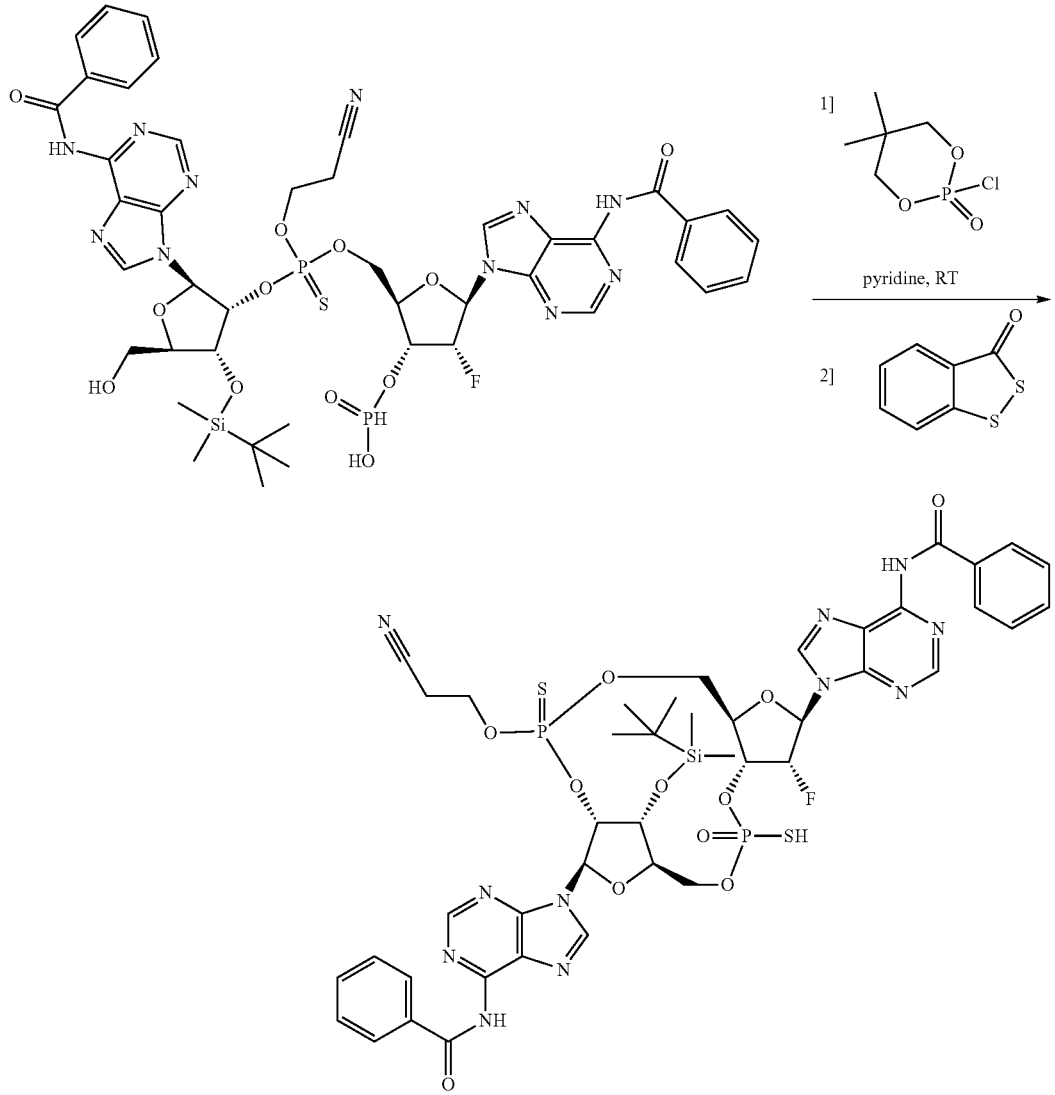

A solution of crude (2R,3R,4R,5R)-5-(6-benzamido-9H-purin-9-yl)-2-(((((2R,3R,4R,5R)-2-(6-benzamido-9H-purin-9-yl)-4-((tert-butyldimethylsilyl)oxy)-5-(hydroxymethyl)tetrahydrofuran-3-yl)oxy)(2-cyanoethoxy)phosphorothioyl)oxy)methyl)-4-fluorotetrahydrofuran-3-yl hydrogen phosphonate (6.84 g, 6.49 mmol) was azeotroped from pyridine (3×50 mL), leaving pyridine (40 mL) after the last concentration. To this solution under nitrogen was added 2-chloro-5,5-dimethyl-1,3,2-dioxaphosphinane 2-oxide (4.19 g, 22.71 mmol) in one portion. The reaction stirred at room temperature under nitrogen for 30 minutes, after which time LCMS indicated consumption of starting material, then the reaction was quenched with the addition of water (4.09 mL, 227 mmol). Then, 3H-benzo[c][1,2]dithiol-3-one (1.638 g, 9.73 mmol), and the mixture stirred at room temperature for 5 minutes before being poured onto a solution of water (400 mL) containing sodium bicarbonate (27.3 g, 324 mmol). The mixture was stirred for 10 minutes, then EtOAc (200 mL) was added, and the mixture stirred for a further 10 minutes. The solution was transferred to a separatory funnel, and the aqueous layer was separated from the organic. The aqueous layer was further extracted with EtOAc (2×200 mL), then the combined organic layers were dried (Na$_2$SO$_4$), filtered and evaporated in vacuo to an orange oil. The material was stored under nitrogen at 4° C. until use in the following step.

After warming to room temperature, the crude material was diluted with toluene (50 mL) and evaporated to remove excess pyridine. This process was repeated two more times. The crude product was purified by chromatography (silica gel, ISCO Teledyne Gold, 220 g silica). Gradient elution was run from 0-10% methanol in dichloromethane over 15 minutes followed by a 5 minute isocratic hold at 10% methanol in dichloromethane. Then the gradient increased from 10-20% methanol in dichloromethane over 15 minutes followed by a 5 minute isocratic hold at 20% methanol in dichloromethane. The desired fractions were combined and evaporated in vacuo to afford an orange oil. The material was stored under nitrogen at 4° C. overnight.

After warming to room temperature, the material was purified again by chromatography (silica gel, ISCO Teledyne Gold, 120 g silica). Gradient elution was run from 0-10% methanol in dichloromethane over 15 minutes followed by a 5 minute isocratic hold at 10% methanol in dichloromethane. Then the gradient increased from 10-20% methanol in dichloromethane over 10 minutes followed by a 5 minute isocratic hold at 20% methanol in dichloromethane. The desired fractions were combined and evaporated in vacuo to the impure titled compound (2.81 g) as a yellow solid. LCMS indicated the presence of two major diastereomers with retention times of 1.09, 1.18 minutes, respectively. Two minor isomers were also observed. The product was stored under nitrogen at 4° C. until use in the following step without further purification. LCMS m/z 1068 (M+H).

Intermediate 5

(1R,6R,8R,9R,10R,15R,17R,18R)-8,17-bis(6-amino-9H-purin-9-yl)-18-[(tert-butyldimethylsilyl)oxy]-9-fluoro-3,12-disulfanyl-2,4,7,11,13,16-hexaoxa-3$\lambda^5$,12$\lambda^5$-diphosphatricyclo[13.2.1.0$^{6,10}$]octadecane-3,12-dione, bisammonium salt

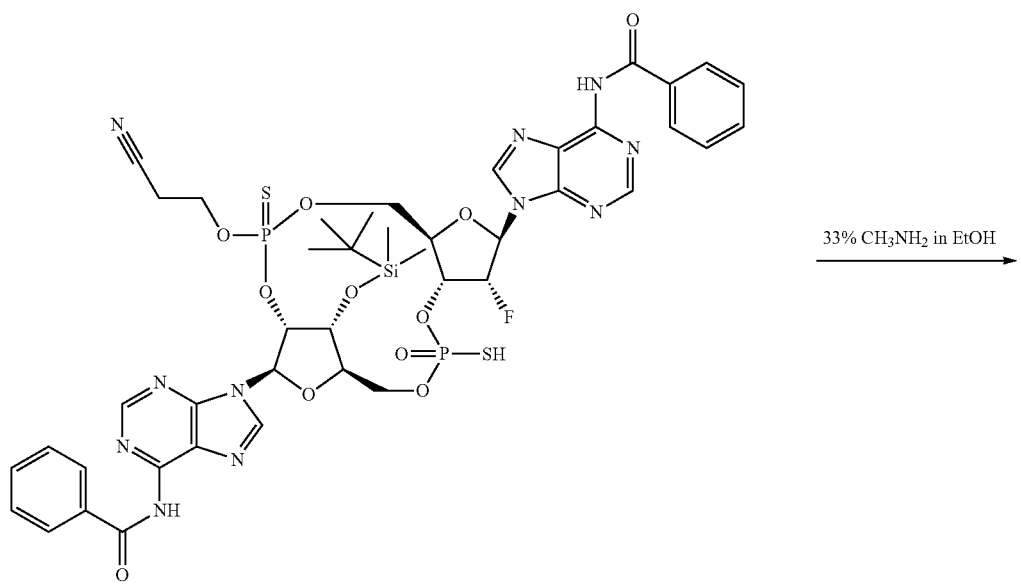

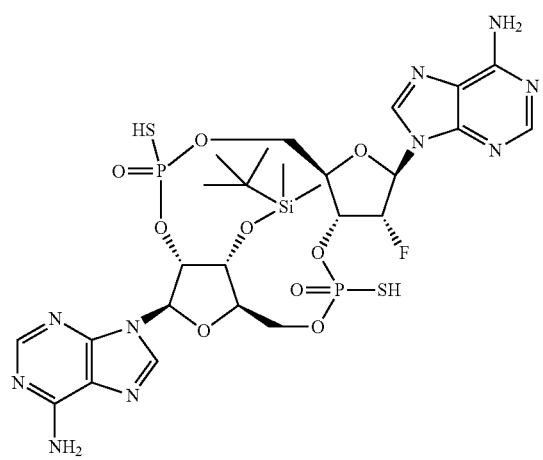

To a solution of above obtained N-{9-[(1R,6R,8R,9R,10R,15R,17R,18R)-17-(6-benzamido-9H-purin-9-yl)-18-[(tert-butyldimethylsilyl)oxy]-3-(2-cyanoethoxy)-9-fluoro-12-oxo-12-sulfanyl-3-sulfanylidene-2,4,7,11,13,16-hexaoxa-3$\lambda^5$,12$\lambda^2$-diphosphatricyclo[13.2.1.0$^{6,10}$]octadecan-8-yl]-9H-purin-6-yl}benzamide (1.0 g, 0.936 mmol) in ethanol (5 mL) was added methylamine (33 wt % in ethanol) (20 ml, 161 mmol) at room temperature. The mixture was stirred at room temperature for 30 minutes, after which time LCMS indicated consumption of starting materials. The reaction mixture was concentrated in vacuo to a tan residue. The material was taken into DMSO and purified using chromatography (reverse phase silica gel, RediSep Gold C18, 30 g). Gradient elution was run at 100% water (with 0.1% NH4OH modifier) for 4 CV followed by 0-15% acetonitrile in water (with 0.1% NH4OH modifier) for 3 CV followed by 15-25% acetonitrile in water (with 0.1% NH4OH modifier) for 6 CV followed by 25-90% acetonitrile in water (with 0.1% NH4OH modifier) for 3 CV followed by an isocratic hold at 90% acetonitrile in water (with 0.1% NH4OH modifier) for 4 CV.

Fractions from the purification were combined and two major isomeric products were isolated:

Isomer 2 of the titled compound as a bisammonium salt, with the exact stereochemistry at two phosphorus centers undetermined (28 mg, purity by LCMS =54%; 0.018 mmol, 1.921% yield) as a colorless resiude, LCMS m/z 807.1 (M+H), $t_{RET}$=0.80 min.

Isomer 3 of the titled compound as a bisammonium salt, with the exact stereochemistry at two phosphorus centers undetermined (46 mg, purity by LCMS =70%, 0.038 mmol, 4.09% yield) as a yellow residue, LCMS m/z 807.2 (M+H), $t_{RET}$=0.91 min.

Examples 8a and 8b (1R,6R,8R,9R,10R,15R,17R,18R)-8,17-bis(6-amino-9H-purin-9-yl)-9-fluoro-18-hydroxy-3,12-disulfanyl-2,4,7,11,13,16-hexaoxa-3$\lambda^5$,12$\lambda^5$-diphosphatricyclo[13.2.1.0$^{6,10}$]octadecane-3,12-dione, bisammonium salt

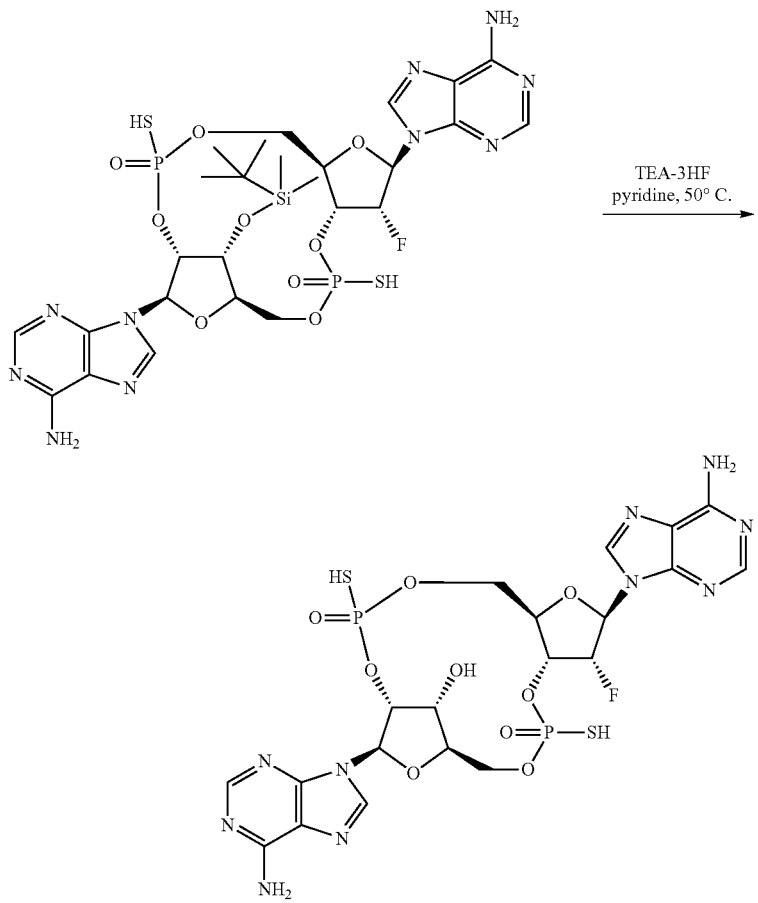

1a - Isomer 1 & 1b - Isomer 2

Isomer 2 of Intermediate 5, (1R,6R,8R,9R,10R,15R,17R,18R)-8,17-bis(6-amino-9H-purin-9-yl)-18-[(tert-butyldimethylsilyl)oxy]-9-fluoro-3,12-disulfanyl-2,4,7,11,13,16-hexaoxa-3$\lambda^5$,12$\lambda^5$-diphosphatricyclo[13.2.1.0$^{6,10}$]octadecane-3,12-dione (25 mg, 0.031 mmol), obtained from the preceding step, was suspended in pyridine (0.5 mL) and triethylamine (0.5 mL). The mixture was stirred and heated to 50° C., then triethylamine trihydrofluoride (0.5 mL, 3.07 mmol) was added and the mixture was stirred at 50° C. for 2 hours, after which time, LCMS indicated complete consumption of starting material and conversion to desired product. The reaction mixture evaporated in vacuo, and the flask was stored under nitrogen at 4° C. overnight.

After warming to room temperature, the residue was taken into water (~5 mL) and a precipitate formed. The solids were separated from the mixture, and the filtrate was adjusted to pH=10 using ammonium hydroxide. The solution was purified using reverse phase HPLC (0-5% acetonitrile:water (with 0.1% NH4OH modifier), C18 50×30 mm Gemini column, 40 mL/min, 7 minute gradient, UV detection=214 nm). The collected solids were taken into water (~2 mL) and methanol (~0.5 mL), and ammonium hyroxide was added to pH=10. The solution was purified using reverse phase HPLC (0-5% acetonitrile:water (with 0.1% NH4OH modifier), C18 50×30 mm Gemini column, 40 mL/min, 7 minute gradient, UV detection=214 nm).

The desired fractions from both purifications were combined and evacuated in vacuo to afford a colorless residue. The residue was taken into water (2 mL) and lyophilized overnight to afford the titled compound (Example 8a, 7 mg) as a bisammonium salt as a single diastereomer, with the exact stereochemistry at the two phosphorus centers undetermined. The product was a white solid. LCMS m/z 693.3 (M+H). $t_{RET}$=0.29 min.

$^1$H NMR (400 MHz, DMSO-$d_6$ with one drop of $D_2O$) δ ppm 8.59-8.62 (m, 1H), 8.39-8.41 (m, 1H), 8.17 (s, 1H), 8.13 (s, 1H), 6.19-6.27 (m, 1H), 6.05-6.10 (m, 1H), 5.70-5.87 (m, 1H), 5.24-5.36 (m, 1H), 5.14-5.23 (m, 1H), 4.31-4.36 (m, 1H), 4.23-4.29 (m, 1H), 4.15-4.23 (m, 1H), 4.11-4.15 (m, 1H), 3.98-4.08 (m, 1H), 3.82-3.91 (m, 1H), 3.66-3.72 (m, 1H).

$^{31}$P NMR (162 MHz, DMSO-$d_6$ with one drop of $D_2O$) δ ppm 53.66, 55.91.

$^{19}$F NMR (376 MHz, DMSO-$d_6$ with one drop of $D_2O$) δ ppm −206.48.

Isomer 3 of Intermediate 5, (1R,6R,8R,9R,10R,15R,17R,18R)-8,17-bis(6-amino-9H-purin-9-yl)-18-[(tert-butyldimethylsilyl)oxy]-9-fluoro-3,12-disulfanyl-2,4,7,11,13,16-hexaoxa-3λ$^5$,12λ$^5$-diphosphatricyclo[13.2.1.0$^{6,10}$]octadecane-3,12-dione (175 mg, 0.217 mmol), obtained from a different batch (purity by LCMS=50%), was suspended in pyridine (1 mL) and triethylamine (1 mL). The mixture was stirred and heated to 50° C., then triethylamine trihydrofluoride (1 mL, 6.14 mmol) was added and the mixture was stirred at 50° C. for 3 hours, after which time, LCMS indicated complete consumption of starting material and conversion to desired product. The mixture was allowed to cool to room temperature, then acetone (~10 mL) was added and a fine precipitate formed. The precipitate was collected via vacuum filtration to afford a gray residue, which was discarded. The filtrate was evaporated in vacuo, and the flask was stored under nitrogen at 4° C. overnight.

After warming to room temperature, the residue was taken into methanol (~6 mL) and purified using reverse phase HPLC (0-15% acetonitrile:water (with 0.1% NH4OH modifier), C18 50×30 mm Gemini column, 47 mL/min, 8 minute gradient, UV detection=214 nm). The desired fractions were combined and evacuated in vacuo to afford a white solid, still contaminated by some impurities.

The solid was further purified using preparative HILIC column (Luna HILIC, 5 u 21×250 mm, 20 mL/min, UV detection=254 nm) with an isocratic gradient of 20% aqueous ammonium formate and 80% acetonitrile. The desired fractions were combined and evaporated in vacuo 90%, then taken into water and acetonitrile and 5 drops of ammonium hydroxide was added to pH=10. The material was frozen and lyophilized overnight. This process was repeated twice more to afford the titled compound (Example 8b, 12 mg) as a bisammonium salt as a single diastereomer, with the exact stereochemistry at the two phosphorus centers undetermined. The product was a white solid. LCMS m/z 693.3 (M+H), $t_{RET}$=0.37 min.

$^1$H NMR (600 MHz, DMSO-$d_6$ with one drop of $D_2O$) δ ppm 8.50-9.29 (m, 1H), 8.43 (br s, 1H), 8.16 (s, 1H), 7.73-8.11 (m, 1H), 6.26 (br d, J=14.4 Hz, 1H), 6.15 (br d, J=7.2 Hz, 1H), 5.72 (s, 1H), 5.29-5.41 (m, 1H), 5.17-5.29 (m, 1H), 4.27-4.46 (m, 2H), 4.21 (br s, 1H), 4.01-4.15 (m, 1H), 3.86-3.91 (m, 1H), 3.81-3.86 (m, 1H), 3.77 (br d, J=10.6 Hz, 1H).

$^{31}$P NMR (162 MHz, DMSO-$d_6$ with one drop of $D_2O$) δ ppm 54.27, 49.69.

$^{19}$F NMR (376 MHz, DMSO-$d_6$ with one drop of $D_2O$) δ ppm −204.90 (br.)

Examples 9a and 9b

Compounds 2a and 2b (1R,6R,8R,9R,10R,15R,17R,18R)-8,17-bis(6-amino-9H-purin-9-yl)-9-fluoro-12,18-dihydroxy-3-sulfanyl-2,4,7,11,13,16-hexaoxa-3λ$^5$,12λ$^5$-diphosphatricyclo[13.2.1.0$^{6,10}$]octadecane-3,12-dione, bisammonium salt

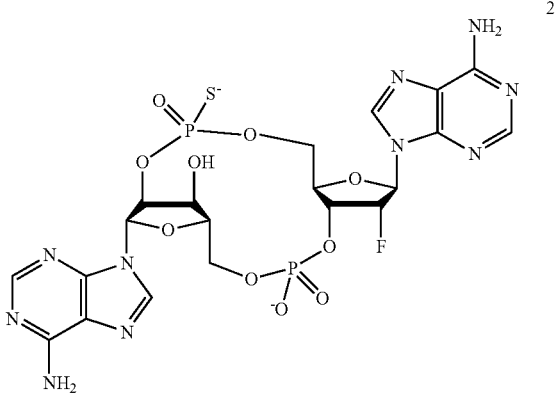

2a - Isomer 1
2b - Isomer 2

Intermediate 2

(2R,3R,4R,5R)-5-(6-benzamido-9H-purin-9-yl)-4-fluoro-2-(hydroxymethyl)tetrahydrofuran-3-yl hydrogen phosphonate

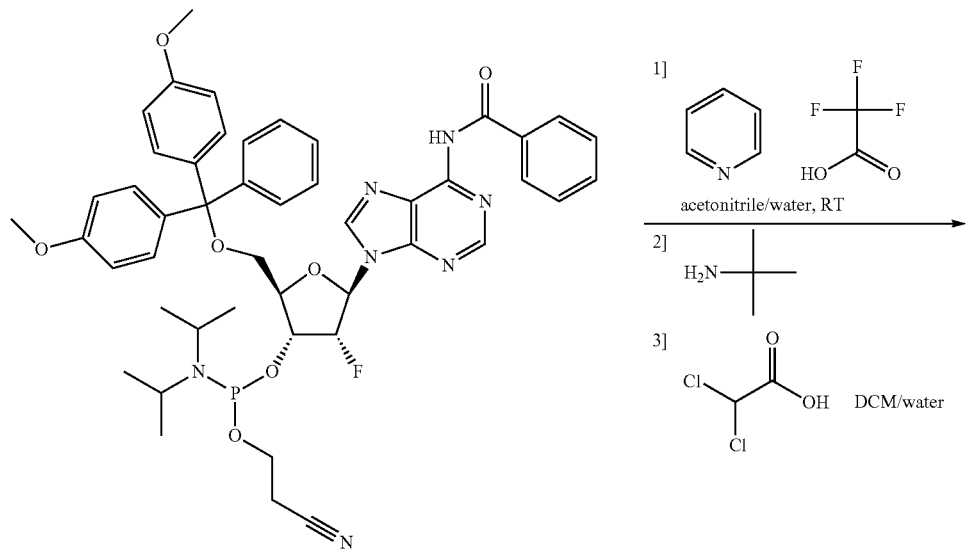

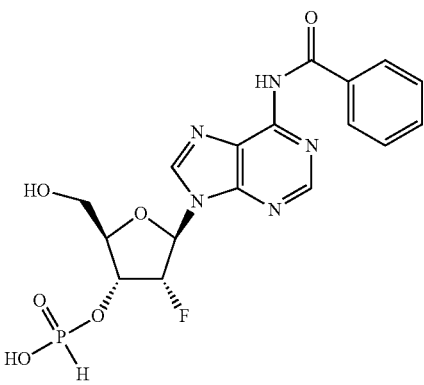

Intermediate 2 was made generally according to the procedure below. Slight modifications, for example those depicted for Intermediate 2 in other Examples, may be used.

To a room temperature solution of (2R,3R,4R,5R)-5-(6-benzamido-9H-purin-9-yl)-2-((bis(4-methoxyphenyl) (phenyl)methoxy)methyl)-4-fluorotetrahydrofuran-3-yl (2-cyanoethyl) diisopropylphosphoramidite (4.01 g, 4.6 mmol) in acetonitrile (35 mL) and water (0.165 mL, 9.1 mmol) was added pyridine 2,2,2-trifluoroacetate (1.06 g, 5.5 mmol). The reaction was stirred for 10 minutes then neat tert-butylamine (24.2 mL, 228 mmol) was added. The reaction was stirred at room temperature for 30 minutes then concentrated under reduced pressure. The resulting white foam was azeotroped from acetonitrile (2×) then the dry residue was taken into a mixture of dichloromethane (100 mL) and water (0.82 mL, 45.7 mmol) and treated with neat 2,2-dichloroacetic acid (3.01 mL, 36.5 mmol). After 30 minutes, the reaction was quenched with pyridine (5.91 mL, 73.1 mmol) then concentrated under reduced pressure to an oily suspension. The material was azeotroped from acetonitrile (3×) then taken into anhydrous acetonitrile (60 mL) and concentrated to a volume of about 20 mL to afford the impure titled compound as a light orange suspension. LCMS m/z 437.9 (M+H). This mixture was used in the next step without further purification.

Intermediate 3

(2R,3R,4R,5R)-5-(6-benzamido-9H-purin-9-yl)-2-((((((2R,3R,4R,5R)-2-(6-benzamido-9H-purin-9-yl)-4-((tert-butyldimethylsilyl)oxy)-5-(hydroxymethyl)tetrahydrofuran-3-yl)oxy)(2-cyanoethoxy)phosphorothioyl)oxy)methyl)-4-fluorotetrahydrofuran-3-yl hydrogen phosphonate solution was added to the previously prepared crude mixture (Intermediate 2) of (2R,3R,4R,5R)-5-(6-benzamido-9H-purin-9-yl)-4-fluoro-2-(hydroxymethyl)tetrahydrofuran-3-yl hydrogen phosphonate (2.0 g, 4.6 mmol) under nitrogen. The reaction was stirred at room temperature for 1 hour then was treated with 3-(dimethylaminomethylidene)amino)-3H-1,2,4-dithiazole-3-thione (1.03 g, 5.0 mmol), stirred for 30 minutes and concentrated under reduced pressure. The resi-

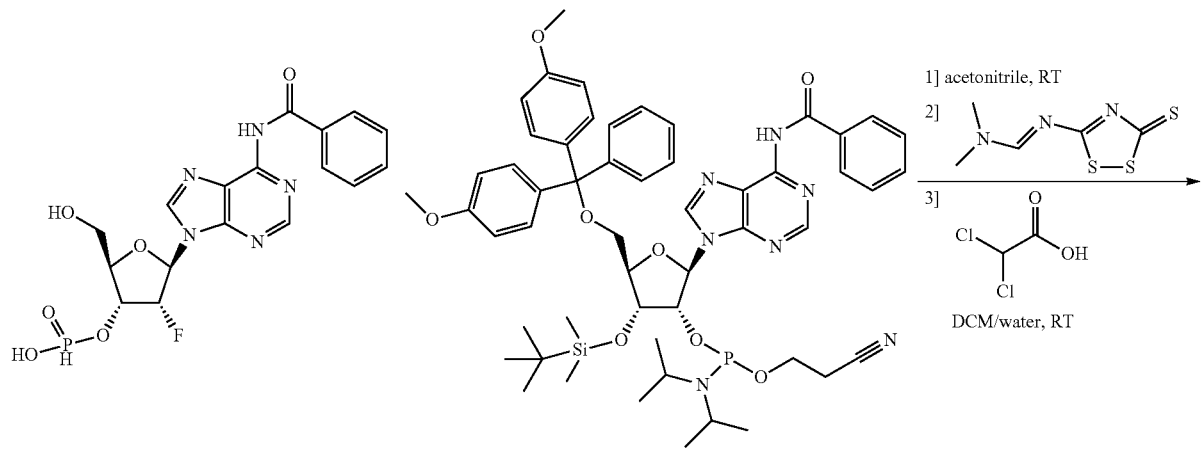

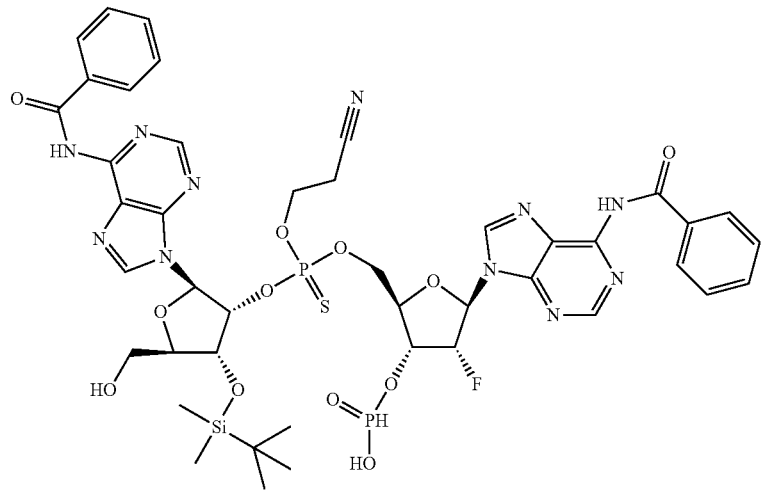

Intermediate 3 was made generally according to the procedure below. Slight modifications, for example those depicted for Intermediate 3 in other Examples, may be used.

(2R,3R,4R,5R)-2-(6-Benzamido-9H-purin-9-yl)-5-((bis(4-methoxyphenyl)(phenyl)methoxy)methyl)-4-((tert-butyldimethylsilyl)oxy)tetrahydrofuran-3-yl (2-cyanoethyl) diisopropylphosphoramidite (5.9 g, 5.9 mmol) was azeotroped from acetonitrile (2×) then taken into 40 mL of anhydrous acetonitrile, concentrated by about half, then stored under nitrogen over 3A molecular sieves. After 1 hour, this due was taken into a mixture of dichloromethane (60 mL) and water (0.823 mL, 45.7 mmol) then treated with 2,2-dichloroacetic acid (4.5 mL, 54.8 mmol). This was stirred at room temperature for 15 minutes before quenching with pyridine (25 mL, 309 mmol) and concentration under reduced pressure. The oily concentrate was azeotroped from pyridine then taken into anhydrous pyridine (60 mL) and concentrated under reduced pressure to about 20 mL to afford the impure titled compound as a dark orange oil. LCMS m/z 1054.2 (M+H). This mixture was used in the next step without further purification.

Intermediate 6

N-{9-[(1R,6R,8R,9R,10R,15R,17R,18R)-17-(6-benzamido-9H-purin-9-yl)-18-[(tert-butyldimethylsilyl)oxy]-3-(2-cyanoethoxy)-9-fluoro-12-hydroxy-12-oxo-3-sulfanylidene-2,4,7,11,13,16-hexaoxa-3λ⁵,12λ⁵-diphosphatricyclo[13.2.1.0⁶,¹⁰]octadecan-8-yl]-9H-purin-6-yl}benzamide

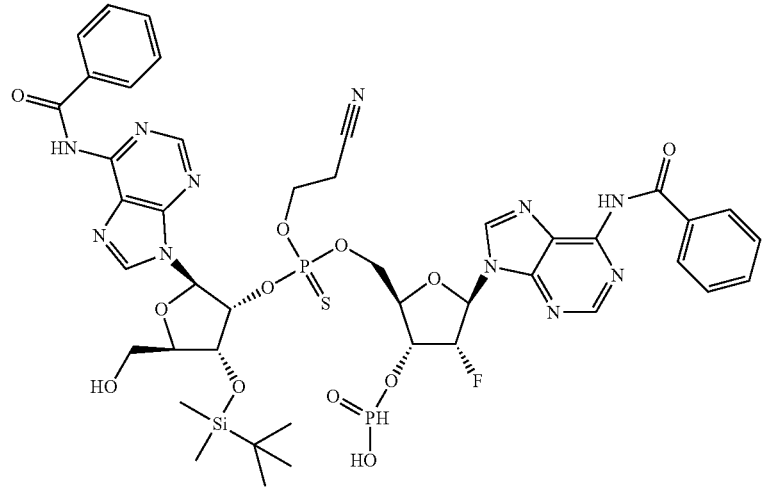

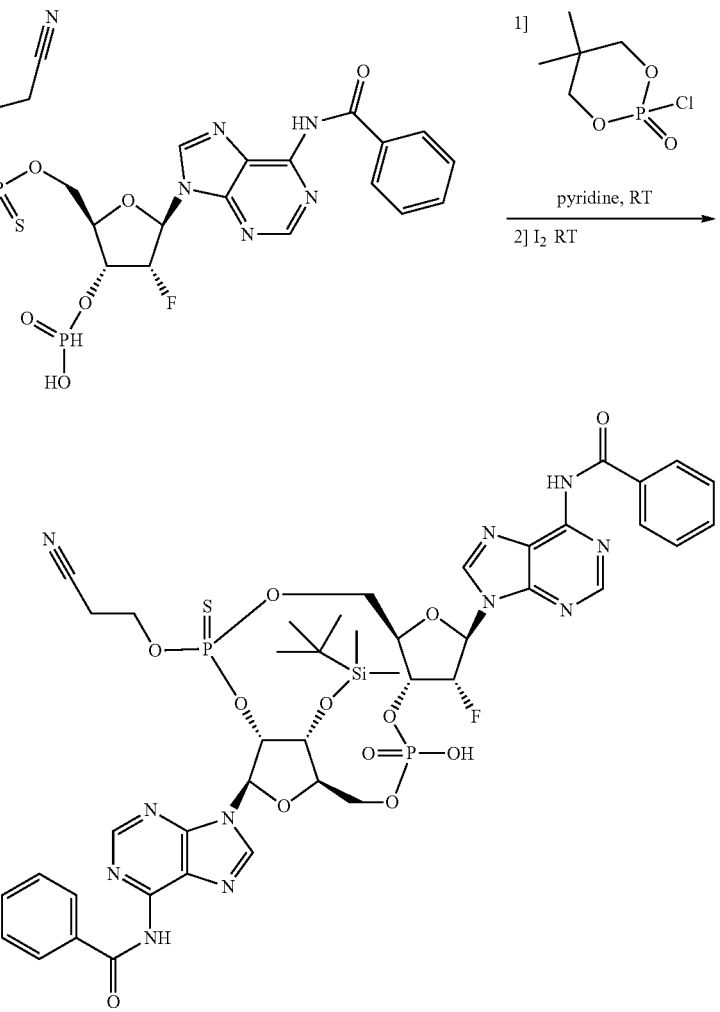

To a crude solution of (2R,3R,4R,5R)-5-(6-benzamido-9H-purin-9-yl)-2-(((((2R,3R,4R,5R)-2-(6-benzamido-9H-purin-9-yl)-4-((tert-butyldimethylsilyl)oxy)-5-(hydroxymethyl)tetrahydrofuran-3-yl)oxy)(2-cyanoethoxy)phosphorothioyl)oxy)methyl)-4-fluorotetrahydrofuran-3-yl hydrogen phosphonate (Intermediate 3, 4.8 g, 4.6 mmol) in pyridine (20 mL) under nitrogen was added 2-chloro-5,5-dimethyl-1,3,2-dioxaphosphinane 2-oxide (3.0 g, 16.0 mmol). The reaction stirred at room temperature under nitrogen for 30 minutes then was quenched with the addition of water (2.9 mL, 160 mmol) followed by iodine (1.5 g, 5.9 mmol). After 10 minutes, the mixture was poured into a solution of sodium bisulfite (0.95 g, 9.1 mmol) in water (300 mL). After 5 minutes, the reaction mixture was treated portion-wise with solid sodium bicarbonate (19.2 g, 229 mmol). The resulting tan suspension was extracted with EtOAc (3×200 mL) then the extracts were washed with saturated aqueous sodium bicarbonate, dried over Na₂SO₄ and concentrated to an oil. One of the two following purification methods was then used to purify the product for different batches.

Method A: The oil was azeotroped from toluene to remove excess pyridine then purified by chromatography on silica (Biotage-100 g) eluting with successive gradients of 0-10% MeOH in DCM (10 min), 10% MeOH in DCM (10 minutes), 10-20% MeOH in DCM (10 min) and finally 20-40% MeOH in DMC (10 min). The fractions of interest identified by LCMS were combined and concentrated to afford the impure titled compound (1.03 g, 0.979 mmol) as a light orange solid. Two isomers were observed by LCMS [m/z 1052.3 (M+H)] in an approximate ratio of 1:1 with retention times of 1.00, 1.09 minutes, respectively. The product was stored under nitrogen at 4° C. and used in the next step without further purification.

Method B: The oil was azeotroped from toluene to remove excess pyridine then purified by chromatography on silica (Teledyne ISCO Gold—120 g) eluting with successive gradients of 100% DCM (5 min), 0-10% MeOH in DCM (5 min), 10% MeOH in DCM (10 minutes), and 10-40% MeOH in DMC (20 min). The fractions of interest were combined and concentrated to afford an approximate 1:1 mixture of diastereomers as a dark yellow solid. The mixture of diastereomers was separated by reverse phase HPLC (Gemini C-18: 30×50 mm column; 45-60% $CH_3CN$ w/0.1% TFA/water w/0.1% TFA), 12 min run collecting at 214 nm. The fractions of interest were combined, treated with saturated aqueous sodium bicarbonate then concentrated to remove acetonitrile. The aqueous concentrates were then extracted with EtOAc. The dried extracts (over $Na_2SO_4$) were concentrated to afford the individual diastereomers.

Diastereomer 1 of the titled compound (42 mg) as a white solid, with the exact stereochemistry at the chiral phosphorus center undetermined. LCMS m/z 1052.7 (M+H), $t_{RET}$=1.00 min.

Diastereomer 2 of the titled compound (43 mg) as a white solid, with the exact stereochemistry at the chiral phosphorus center undetermined. LCMS m/z 1052.7 (M+H). $t_{RET}$=1.09 min.

Examples 9a and 9b (1R,6R,8R,9R,10R,15R,17R,18R)-8,17-bis(6-amino-9H-purin-9-yl)-9-fluoro-12,18-dihydroxy-3-sulfanyl-2,4,7,11,13,16-hexaoxa-3λ⁵,12λ⁵-diphosphatricyclo[13.2.1.0⁶,¹⁰]octadecane-3,12-dione, bisammonium salt

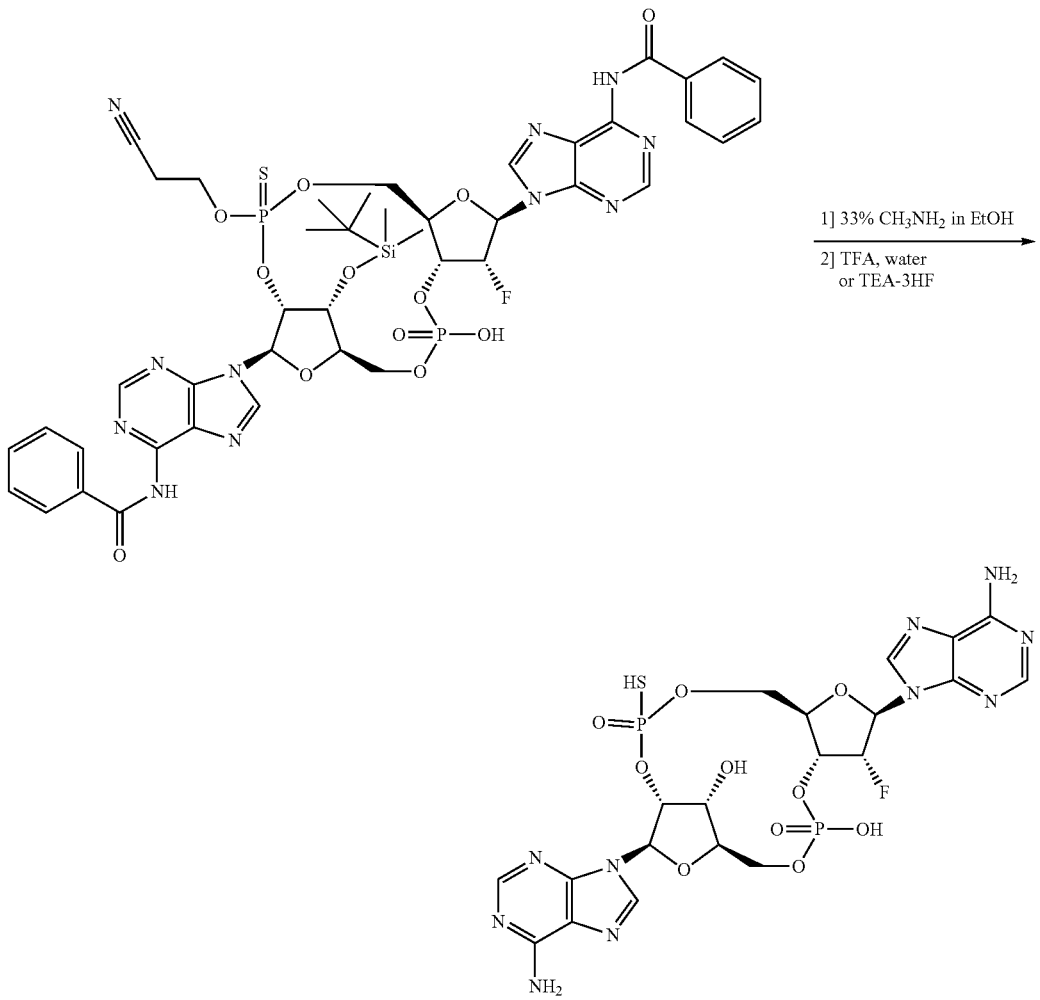

2a - Isomer 1 & 2b - Isomer 2

A solution of intermediate 6 (purified by method A), N-{9-[(1R,6R,8R,9R,10R,15R,17R,18R)-17-(6-benzamido-9H-purin-9-yl)-18-[(tert-butyldimethylsilyl)oxy]-3-(2-cyanoethoxy)-9-fluoro-12-hydroxy-12-oxo-3-sulfanylidene-2,4,7,11,13,16-hexaoxa-3λ⁵,12λ⁵-diphosphatricyclo[13.2.1.0⁶,¹⁰]octadecan-8-yl]-9H-purin-6-yl}benzamide (1.03 g, 0.979 mmol) in 33% wt methylamine in EtOH (40 mL, 321 mmol) was stirred at room temperature for 4 hours whereupon LCMS indicated complete conversion of the starting material and the presence of the desired O-TBS protected intermediate. Only one, slightly broad peak for the intermediate was noted, indicating at least one diastereomer was present. The reaction was concentrated to a dark orange residue which was purified by reverse phase HPLC (Gemini C-18: 30×50 mm column; 10-60% acetonitrile w/0.1% TFA/water w/0.1% TFA), 12 minute gradient with detection at 254 nm. The fractions of interest were combined and concentrated under reduced pressure. At this point, LCMS indicated the loss of the silyl protecting group. The aqueous phase was further concentrated to approximately 3-5 mL then methanol (25 mL) was added. The resulting suspension was filtered and the solids were rinsed with MeOH and then diethyl ether then suction dried to afford 75 mg of the impure desired product-diTFA salt as a white solid. LCMS m/z 677.2 (M+H).

The product was further purified by prep-chromatography (Luna HILIC 3 u: 4.6×150 mm; isocratic 20% 30 mM aqueous $HCO_2NH_4$, 80% $CH_3CN$). The fractions of interest were combined and concentrated to a residue that was lyophilized out of water (5 mL) and 3 drops ammonium hydroxide). To remove residual ammonium formate, the lyophilization process was repeated 4 more times to afford the titled compound (Example 9a, 50 mg) as a bisammonium salt as a single diastereomer, with the exact stereochemistry at the chiral phosphorus center being undetermined. The titled product was a white solid. LCMS m/z 677.6 (M+H). $t_{RET}$=0.11 min $^1$H NMR (600 MHz, DMSO-$d_6$ with one drop of $D_2O$): δ ppm 8.48 (s, 1H), 8.39 (s, 1H), 8.17 (s, 1H), 8.12 (s, 1H), 6.23 (dd, J=15.1, 3.0 Hz, 1H), 6.09 (d, J=8.3 Hz, 1H), 5.69 (br dt, J=52.1, 3.4 Hz, 1H), 5.16 (ddd, J=8.1, 6.6, 4.2 Hz, 1H), 5.02-5.10 (m, 1H), 4.35 (d, J=4.2 Hz, 1H), 4.24 (br s, 1H), 4.11-4.18 (m, 1H), 4.09 (br s, 1H), 3.97 (br d, J=10.6 Hz, 1H), 3.89-3.95 (m, 1H), 3.72 (br d, J=12.5 Hz, 1H).

$^{13}$C NMR (150 MHz DMSO-$d_6$, with one drop of $D_2O$): δ ppm 156.0, 155.8, 153.0, 152.8, 150.3, 148.9, 119.1, 118.4, 92.4, 85.4, 84.0, 83.3, 81.0, 77.9, 72.3, 71.4, 65.9, 62.6.

$^{31}$P NMR (162 MHz, DMSO-$d_6$, with one drop of $D_2O$) δ ppm 55.67 and −2.51.

$^{19}$F NMR (376 MHz, DMSO-$d_6$, with one drop of $D_2O$) δ ppm −205.16.

It is noted that Example 9a may also be prepared using the procedure depicted below for Example 9b.

A solution of Diastereomer 2 of Intermediate 6 (purified by method B), N-{9-[(1R,6R,8R,9R,10R,15R,17R,18R)-17-(6-benzamido-9H-purin-9-yl)-18-[(tert-butyldimethylsilyl)oxy]-3-(2-cyanoethoxy)-9-fluoro-12-hydroxy-12-oxo-3-sulfanylidene-2,4,7,11,13,16-hexaoxa-3λ$^5$,12λ$^5$-diphosphatricyclo[13.2.1.0$^{6,10}$]octadecan-8-yl]-9H-purin-6-yl}benzamide (43 mg, 0.041 mmol), in 33% wt methylamine in EtOH (8.0 mL, 64.3 mmol) was stirred at room temperature for 30 minutes and then concentrated. The resulting dark orange residue was taken into anhydrous pyridine (0.50 mL) and triethylamine (0.50 mL), heated to 50° C. then treated with triethylamine trihydrofluoride (0.50 mL, 3.07 mmol). After 1 hour, the reaction was complete. The mixture was cooled and concentrated to a dark oil that was taken into water (7.5 mL) and ammonium hydroxide (10 drops). The resulting suspension (pH-3) was filtered and the solids were dissolved into a mixture of water (2 mL) and ammonium hydroxide (1 mL) then purified by reverse phase HPLC (Gemini C-18: 30×50 mm column; 0-10% acetonitrile/water w/0.1% NH4OH; 214 nm). The fractions of interest were combined and concentrated under reduced pressure to a wet residue that was taken into water (5 ml) and 5 drops ammonium hydroxide then lyophillized to afford the titled compound (Example 9b, 7.0 mg) as a bisammonium salt as a single diastereomer, with the exact stereochemistry at the chiral phosphorus center being undetermined. The product was a white solid. LCMS m/z 677.2 (M+H), $t_{RET}$=0.32 min.

$^1$H NMR (600 MHz, DMSO-$d_6$ with one drop of $D_2O$): δ ppm 8.65-9.35 (m, 1H), 8.44 (br s, 1H), 7.77-8.29 (m, 2H), 6.25 (br d, J=14.4 Hz, 1H), 6.11-6.19 (m, 1H), 5.53-5.73 (m, 1H), 5.18-5.44 (m, 1H), 4.96-5.08 (m, 1H), 4.40-4.54 (m, 1H), 4.33 (br s, 2H), 4.23-4.30 (m, 1H), 4.16 (br s, 1H), 3.98-4.06 (m, 1H), 3.81 (br s, 1H).

$^{31}$P NMR (162 MHz, DMSO-$d_6$ with one drop of $D_2O$) δ ppm 49.48 and −2.94.

$^{19}$F NMR (376 MHz, DMSO-$d_6$ with one drop of $D_2O$) δ ppm −206.44 (br).

Examples 10a and 10b

Compounds 28a and 28b (1R,6R,8R,9R,10R,15R,17R,18R)-17-(2-amino-6-oxo-6,9-dihydro-1H-purin-9-yl)-8-(6-amino-9H-purin-9-yl)-9-fluoro-12,18-dihydroxy-3-sulfanyl-2,4,7,11,13,16-hexaoxa-3λ$^5$,12λ$^5$-diphosphatricyclo[13.2.1.0$^{6,10}$]octadecane-3,12-dione

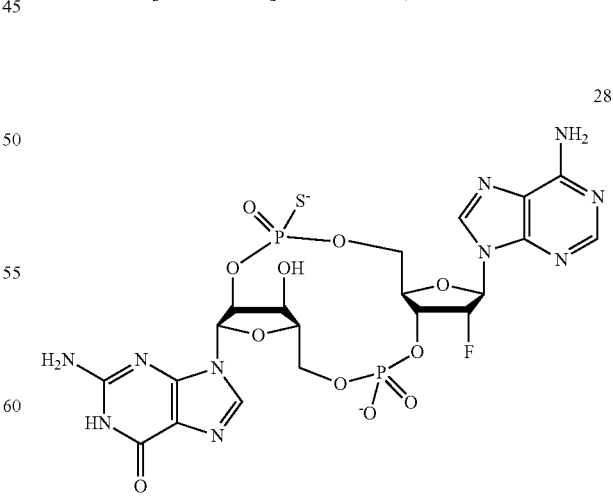

28

28a - Isomer 1
28b - Isomer 2

Intermediate 7

(2R,3R,4R,5R)-5-(6-benzamido-9H-purin-9-yl)-2-(((((2R,3R,4R,5R)-4-((tert-butyldimethylsilyl)oxy)-5-(hydroxymethyl)-2-(2-isobutylamido-6-oxo-1H-purin-9(6H)-yl)tetrahydrofuran-3-yl)oxy)(2-cyanoethoxy)phosphorothioyl)oxy)methyl)-4-fluorotetrahydrofuran-3-yl hydrogen phosphonate

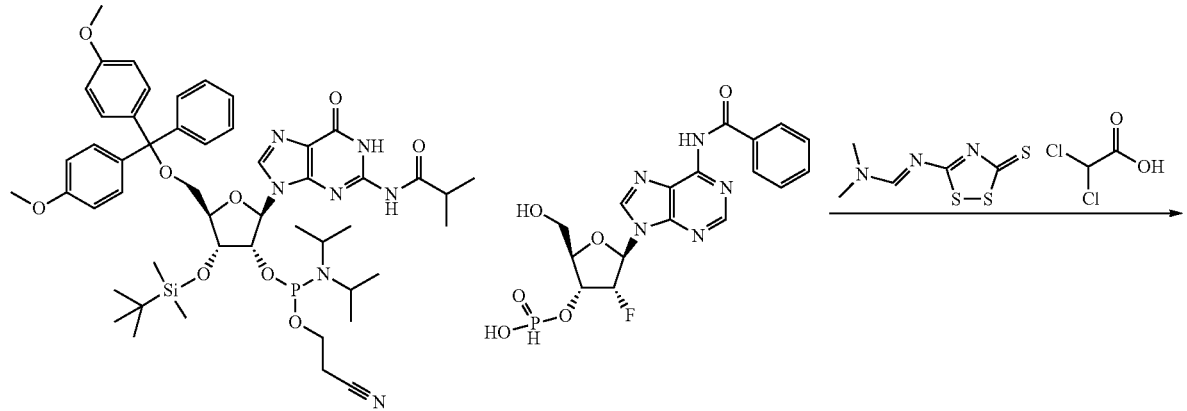

(2R,3R,4R,5R)-5-((bis(4-methoxyphenyl)(phenyl)methoxy)methyl)-4-((tert-butyldimethylsilyl)oxy)-2-(2-isobutylamido-6-oxo-1H-purin-9(6H)-yl)tetrahydrofuran-3-yl (2-cyanoethyl) diisopropylphosphoramidite (4.0 g, 4.12 mmol) was azeotroped with acetonitrile (20 mL) three times. After the last concentration, ~15 mL of acetonitrile was kept in the reaction flask and 3 Å molecular sieves (~20 beads) were added to the clear solution. The solution was left standing over the molecular sieves under nitrogen for ~1 hour.

To a separate round bottom flask of the previously prepared crude mixture (Intermediate 2) of (2R,5R)-5-(6-benzamido-9H-purin-9-yl)-4-fluoro-2-(hydroxymethyl)tetrahydrofuran-3-yl hydrogen phosphonate (1.5 g, 3.43 mmol) in acetonitrile (10 mL) was added via syringe the above pre-dried solution of (2R,3R,4R,5R)-5-((bis(4-methoxyphenyl)(phenyl)methoxy)methyl)-4-((tert-butyldimethylsilyl)oxy)-2-(2-isobutylamido-6-oxo-1H-purin-9(6H)-yl)tetrahydrofuran-3-yl (2-cyanoethyl) diisopropylphosphoramidite in acetonitrile (~15 mL). After 30 minutes of stirring at room temperature, (E)-N,N-dimethyl-N'-(3-thioxo-3H-1,2,4-dithiazol-5-yl)formimidamide (DDTT) (780 mg, 3.80 mmol) was added. The mixture was stirred at room temperature for 30 minutes, followed by evaporation of the acetonitrile in vacuo. Dichloromethane (DCM) (50 mL) and Water (650 µL) were then added to the residue, followed by the addition of 2,2-dichloroacetic acid (3.5 mL, 42.4 mmol). This was stirred at room temperature for 30 minutes before being quenched with pyridine (20 mL). The mixture was concentrated in vacuo to afford the impure titled compound as an orange oil. LCMS m/z 1036.2 (M+H). The crude product was used in the next step without further purification.

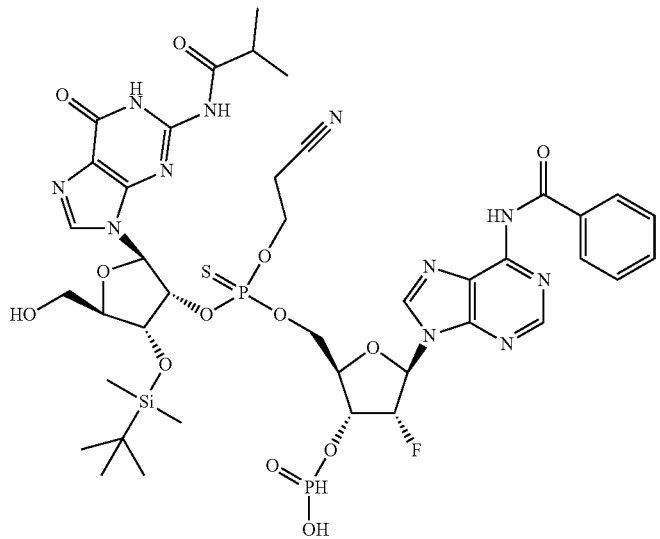

Intermediate 8

N-{9-[(1R,6R,8R,9R,10R,15R,17R,18R)-18-[(tert-butyldimethylsilyl)oxy]-3-(2-cyanoethoxy)-9-fluoro-12-hydroxy-17-[2-(2-methylpropanamido)-6-oxo-6,9-dihydro-1H-purin-9-yl]-12-oxo-3-sulfanylidene-2,4,7,11,13,16-hexaoxa-3λ$^5$,12λ$^5$-diphosphatricyclo[13.2.1.0$^{6,10}$]octadecan-8-yl]-9H-purin-6-yl}benzamide

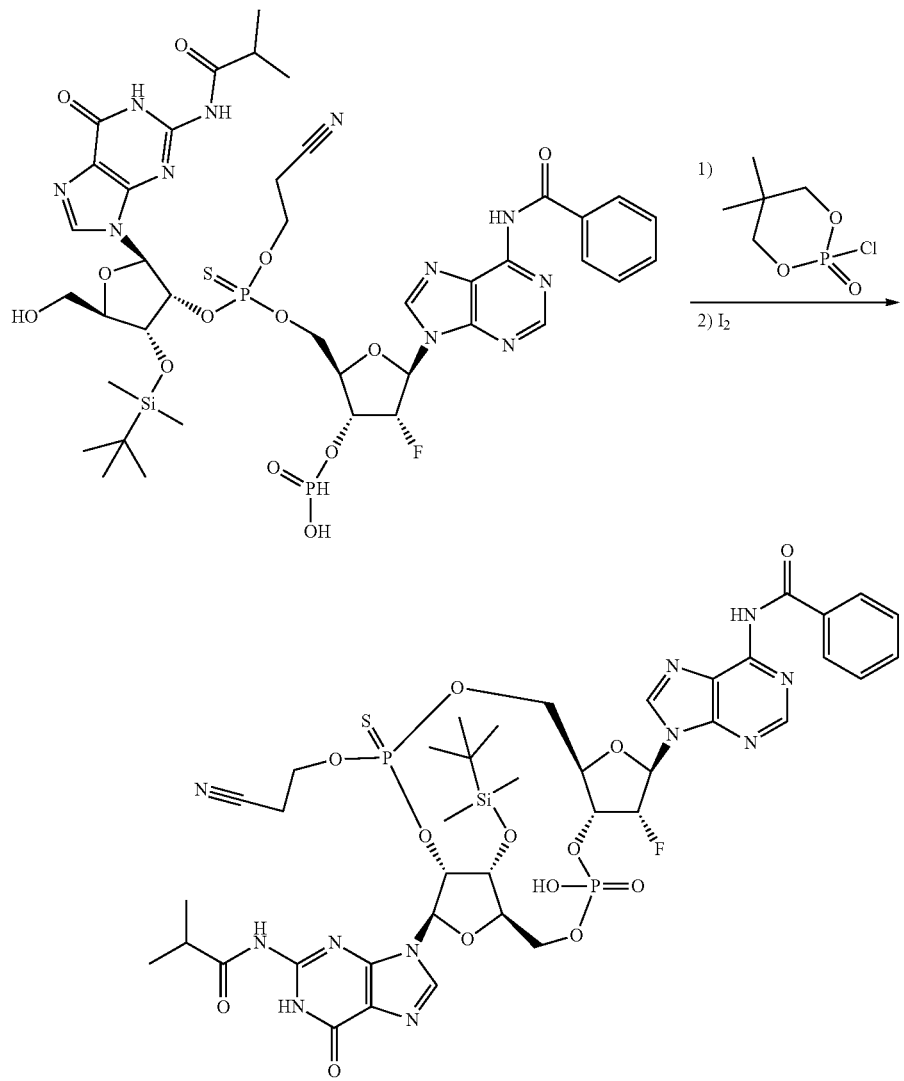

To a crude solution of (2R,3R,4R,5R)-5-(6-benzamido-9H-purin-9-yl)-2-(((((2R,3R,4R,5R)-4-((tert-butyldimethylsilyl)oxy)-5-(hydroxymethyl)-2-(2-isobutyramido-6-oxo-1H-purin-9(6H)-yl)tetrahydrofuran-3-yl)oxy)(2-cyanoethoxy)phosphorothioyl)oxy) methyl)-4-fluorotetrahydrofuran-3-yl hydrogen phosphonate (Intermediate 7, 3.55 g, 3.43 mmol) in pyridine (60 mL) was added 2-chloro-5,5-dimethyl-1,3,2-dioxaphosphinane 2-oxide (DMOCP) (2.2 g, 11.92 mmol), and the mixture was stirred under nitrogen at room temperature for 30 minutes. The reaction was quenched with water (2.2 mL, 10 equiv to DMOCP), followed by addition of iodine (1.2 g, 4.73 mmol). The mixture was stirred for 10 minutes, then poured into a solution of water (400 mL) and sodium bisulfite (NaHSO$_3$) (1.0 g, 9.61 mmol). After 5 minutes of stirring, sodium bicarbonate (NaHCO$_3$) (14.4 g, 171 mmol) was slowly added portionwise as solid (caution: gas evolution). The product was extracted with 1:1 diethyl ether:EtOAc (300 mL×2) and the combined extracts were dried over sodium sulfate, filtered, and concentrated in vacuo. Excess pyridine was removed by concentration with toluene (100 mL×2). The crude material was purified by chromatography on silica (100 gram column) using a gradient of 0-20% MeOH/DCM, then holding at 20% MeOH/DCM until all the desired product had eluted off the column. Desired fractions were combined and concentrated to afford two isomeric products:

Isomer 1 of the titled compound, more polar, as an impure mixture (1.39 g, purity by LCMS ~33% along with ~28% of Isomer 2). LCMS m/z 1034.1 (M+H), t$_{RET}$=0.98 min.

Isomer 2 of the titled compound, less polar, as an impure mixture (230 mg, purity by LCMS ~33%). LCMS m/z 1034.2 (M+H), t$_{RET}$=1.09 min.

Intermediates 9a and 9b (1R,6R,8R,9R,10R,15R,17R,18R)-17-(2-amino-6-oxo-6,9-dihydro-1H-purin-9-yl)-8-(6-amino-9H-purin-9-yl)-18-[(tert-butyldimethylsilyl)oxy]-9-fluoro-12-hydroxy-3-sulfanyl-2,4,7,11,13,16-hexaoxa-3λ$^5$,12λ$^5$-diphosphatricyclo[13.2.1.0$^{6,10}$]octadecane-3,12-dione

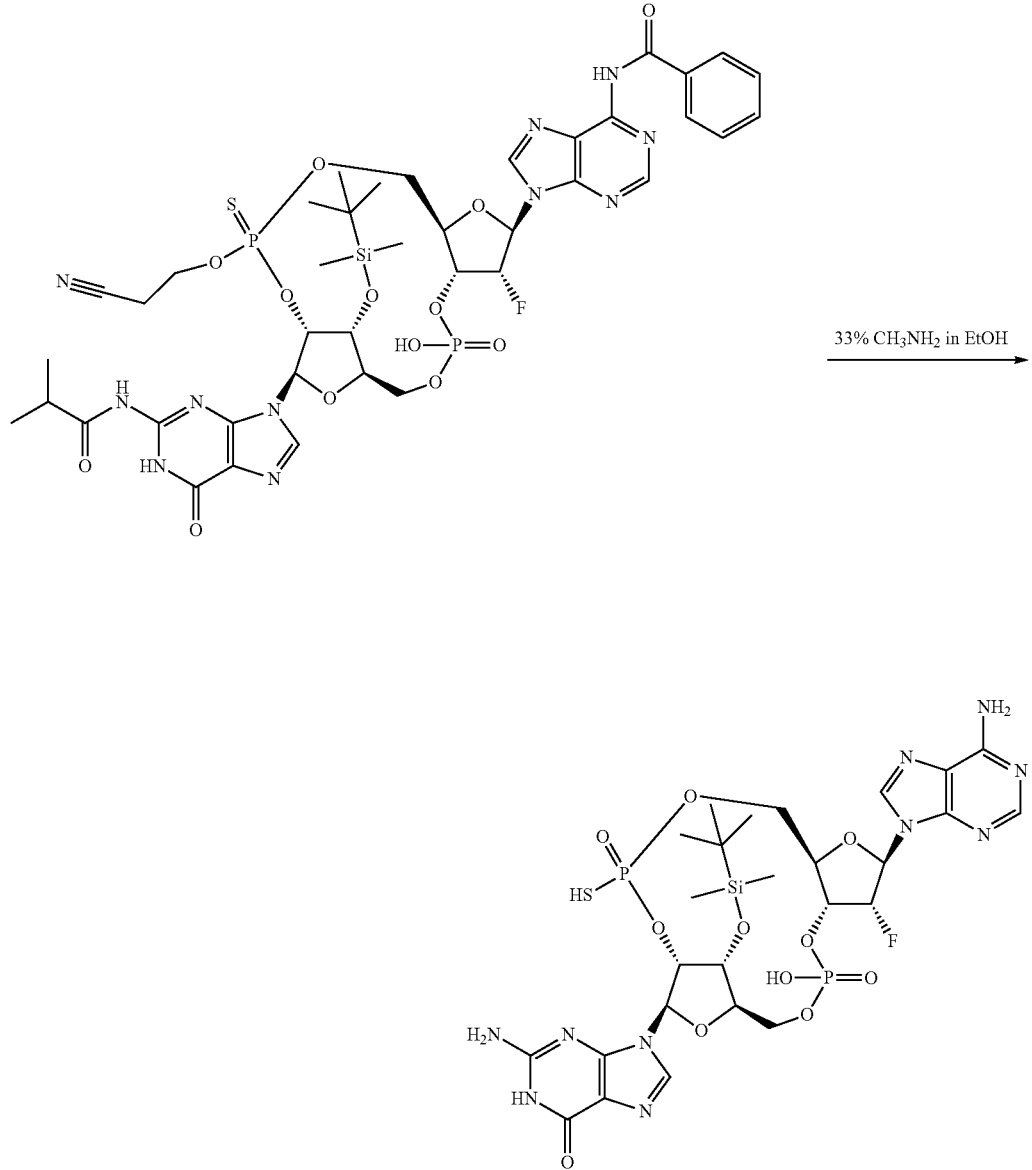 [SMILES: CC(C)C(=O)Nc1nc2c(ncn2[C@@H]2O[C@@H]3COP(=O)(O)O[C@H]4[C@@H](F)[C@H](n5cnc6c(NC(=O)c7ccccc7)ncnc65)O[C@@H]4COP(=S)(OCCC#N)O[C@@H]2[C@@H]3O[Si](C)(C)C(C)(C)C)c(=O)[nH]1 ; CC(C)(C)[Si](C)(C)O[C@H]1[C@H]2OP(=O)(S)OC[C@H]3O[C@@H](n4cnc5c(N)ncnc54)[C@H](F)[C@@H]3OP(=O)(O)OC[C@H]1O[C@H]2n1cnc2c(=O)[nH]c(N)nc21]

Isomer 1 of Intermediate 8, N-{9-[(1R,6R,8R,9R,10R,15R,17R,18R)-18-[(tert-butyldimethylsilyl)oxy]-3-(2-cyanoethoxy)-9-fluoro-12-hydroxy-17-[2-(2-methylpropanamido)-6-oxo-6,9-dihydro-1H-purin-9-yl]-12-oxo-3-sulfanylidene-2,4,7,11,13,16-hexaoxa-3λ$^5$,12λ$^5$-diphosphatricyclo[13.2.1.0$^{6,10}$]octadecan-8-yl]-9H-purin-6-yl}benzamide (1.39 g, 1.34 mmol), was stirred in methanamine (33% wt in EtOH) (10.0 mL, 80 mmol) under nitrogen at room temperature for 3 hours. The reaction mixture was concentrated and the residue was purified via reverse phase HPLC, using a gradient of 10-50% ACN/H$_2$O (0.1% TFA)), to afford Isomer 1 of the titled compound (Intermediate 9a, impure, 280 mg) as a tan solid. LCMS m/z 807.1 (M+H), t$_{RET}$=0.80 min.

Following the same procedure for the preparation of Intermediate 9a, Isomer 2 of Intermediate 8, N-{9-[(1R,6R,8R,9R,10R,15R,17R,18R)-18-[(tert-butyldimethylsilyl)oxy]-3-(2-cyanoethoxy)-9-fluoro-12-hydroxy-17-[2-(2-methylpropanamido)-6-oxo-6,9-dihydro-1H-purin-9-yl]-12-oxo-3-sulfanylidene-2,4,7,11,13,16-hexaoxa-3λ$^5$,12λ$^5$-diphosphatricyclo[13.2.1.0$^{6,10}$]octadecan-8-yl]-9H-purin-6-yl}benzamide (230 mg, 0.22 mmol), was stirred in methanamine (33% wt in EtOH) (2.0 mL, 16 mmol) under nitrogen at room temperature for 3 hours. The reaction mixture was concentrated and the residue was purified via reverse phase HPLC, using a gradient of 10-50% ACN/H$_2$O (0.1% TFA)), to afford Isomer 2 of the titled compound (Intermediate 9b, impure, 60 mg) as a tan solid.

LCMS m/z 807.1 (M+H), t$_{RET}$=0.85 min.

Examples 10a and 10b (1R,6R,8R,9R,10R,15R,17R,18R)-17-(2-amino-6-oxo-6,9-dihydro-1H-purin-9-yl)-8-(6-amino-9H-purin-9-yl)-9-fluoro-12,18-dihydroxy-3-sulfanyl-2,4,7,11,13,16-hexaoxa-3λ$^5$,12λ$^5$-diphosphatricyclo[13.2.1.0$^{6,10}$]octadecane-3,12-dione

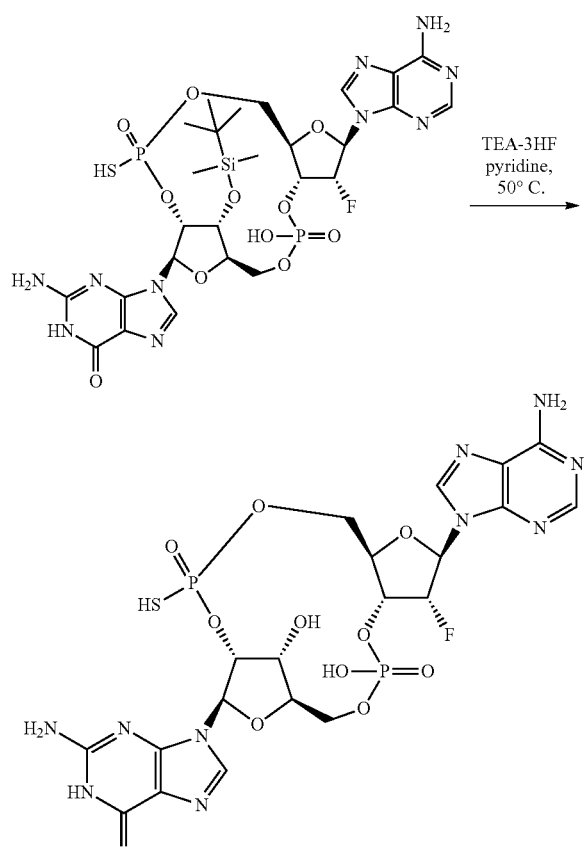

28a - Isomer 1 & 28b - Isomer 2

To a suspension of Isomer 1 of (1R,6R,8R,9R,10R,15R,17R,18R)-17-(2-amino-6-oxo-6,9-dihydro-1H-purin-9-yl)-8-(6-amino-9H-purin-9-yl)-18-[(tert-butyldimethylsilyl)oxy]-9-fluoro-12-hydroxy-3-sulfanyl-2,4,7,11,13,16-hexaoxa-3λ$^5$,12λ$^5$-diphosphatricyclo[13.2.1.0$^{6,10}$]octadecane-3,12-dione (Intermediate 9a, 280 mg, 0.35 mmol) in pyridine (2 mL) and triethylamine (2 mL) at 50° C. was added triethylamine trihydrofluoride (1.5 mL, 9.21 mmol). The mixture was stirred at 50° C. for 4 hours. LCMS indicated some starting material still unconsumed, and the reaction was left to stir at room temperature for 16 hours. After that, the reaction mixture was diluted with acetone (~25 mL) and precipitation was formed. After 15 minutes of stirring, the reaction was filtered. The solid was rinsed with acetone (~10 mL) and dried. The filtrate was concentrated in vacuo and was then added toluene to remove any remaining pyridine. The crude filtrate and filtered solid were individually purified via reverse phase HPLC, using a gradient of 0-20% ACN:H$_2$O (0.1% NH$_4$OH) and combined. $^{19}$F NMR spectra displayed residual TFA present in the samples. A second reverse phase HPLC purification, using a gradient of 0-10% ACN/H$_2$O (0.1% NH$_4$OH), afforded the titled compound (Example 10a, 4 mg) as a bisammonium salt as a single diastereomer, with the exact stereochemistry at the phosphorus center undetermined. The product was a white solid. LCMS m/z 693.0 (M+H). t$_{RET}$=0.11 min.

$^1$H NMR (600 MHz, DMSO-d$_6$ with one drop of D$_2$O): δ ppm 8.30 (s, 1H), 8.19 (s, 1H), 7.97 (s, 1H), 6.26 (dd, J=15.9, 2.3 Hz, 1H), 5.86 (d, J=8.3 Hz, 1H), 5.59-5.76 (m, 1H), 5.30 (br s, 1H), 5.06 (brd, J=15.5 Hz, 1H), 4.35 (d, J=3.8 Hz, 1H), 4.25 (br s, 1H), 4.02-4.07 (m, 1H), 4.01-4.13 (m, 2H), 3.88-3.99 (m, 2H).

$^{19}$F NMR (376 MHz, DMSO-d$_6$ with one drop of D$_2$O) δ ppm −203.83.

$^{31}$P NMR (162 MHz, DMSO-d$_6$ with one drop of D$_2$O) δ ppm 55.73, −2.66.

Following the same procedure for the preparation of Example 10a, the reaction of Isomer 2 of (1R,6R,8R,9R,10R,15R,17R,18R)-17-(2-amino-6-oxo-6,9-dihydro-1H-purin-9-yl)-8-(6-amino-9H-purin-9-yl)-18-[(tert-butyldimethylsilyl)oxy]-9-fluoro-12-hydroxy-3-sulfanyl-2,4,7,11,13,16-hexaoxa-3λ$^5$,12λ$^5$-diphosphatricyclo[13.2.1.0$^{6,10}$]octadecane-3,12-dione (Intermediate 9b, 60 mg, 0.35 mmol) afforded the titled compound (Example 10b, 7 mg) as a bisammonium salt as a single diastereomer, with the exact stereochemistry at the phosphorus center undetermined. The product was a white solid. LCMS m/z 693.0 (M+H), t$_{RET}$=0.37 min.

$^1$H NMR (400 MHz, DMSO-d$_6$ with one drop of D$_2$O): δ ppm 8.50 (br. s., 1 H), H) 8.22 (br. s., 1 H), 7.94 (br. s., 1H), 6.35 (d, J=14 Hz, 1H), 5.87 (d, J=7.86 Hz, 1 H), 5.54-5.67 (m, 1 H), 4.98 (br. d., J=15.5 Hz, 1 H), 4.39 (br. s., 1 H), 4.33 (d, J=6.84 Hz, 1 H), 4.24 (br. s., 1 H), 4.13 (br. s., 1 H), 4.00-4.10 (m, 2 H), 3.89-3.98 (m, 2 H).

$^{19}$F NMR (376 MHz, DMSO-d$_6$ with one drop of D$_2$O) δ ppm −205.00.

$^{31}$P NMR (162 MHz, DMSO-d$_6$ with one drop of D$_2$O) δ ppm 49.15, −2.90.

Examples 11a and 11b

Compounds 27a and 27b (1R,6R,8R,9R,10R,15R,17R,18R)-17-(2-amino-6-oxo-6,9-dihydro-1H-purin-9-yl)-8-(6-amino-9H-purin-9-yl)-9-fluoro-18-hydroxy-3,12-disulfanyl-2,4,7,11,13,16-hexaoxa-3λ$^5$,12λ$^5$-diphosphatricyclo[13.2.1.0$^{6,10}$]octadecane-3, 12-dione, bisammonium salt

27

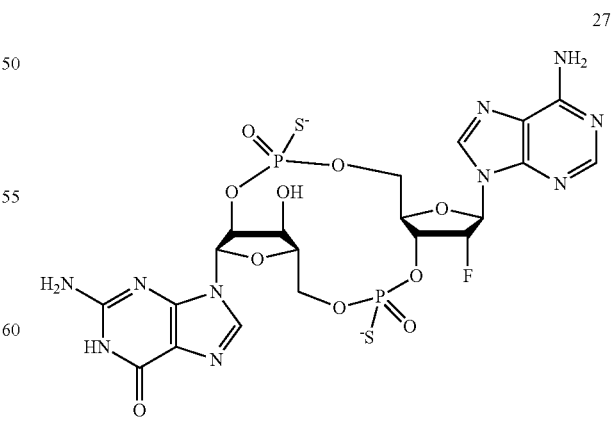

27a - Isomer 1
27b - Isomer 2

Intermediate 10

N-{9-[(1R,6R,8R,9R,10R,15R,17R,18R)-18-[(tert-butyldimethylsilyl)oxy]-3-(2-cyanoethoxy)-9-fluoro-17-[2-(2-methylpropanamido)-6-oxo-6,9-dihydro-1H-purin-9-yl]-12-oxo-12-sulfanyl-3-sulfanylidene-2,4,7,11,13,16-hexaoxa-3λ$^5$,12λ$^5$-diphosphatricyclo[13.2.1.0$^{6,10}$]octadecan-8-yl]-9H-purin-6-yl}

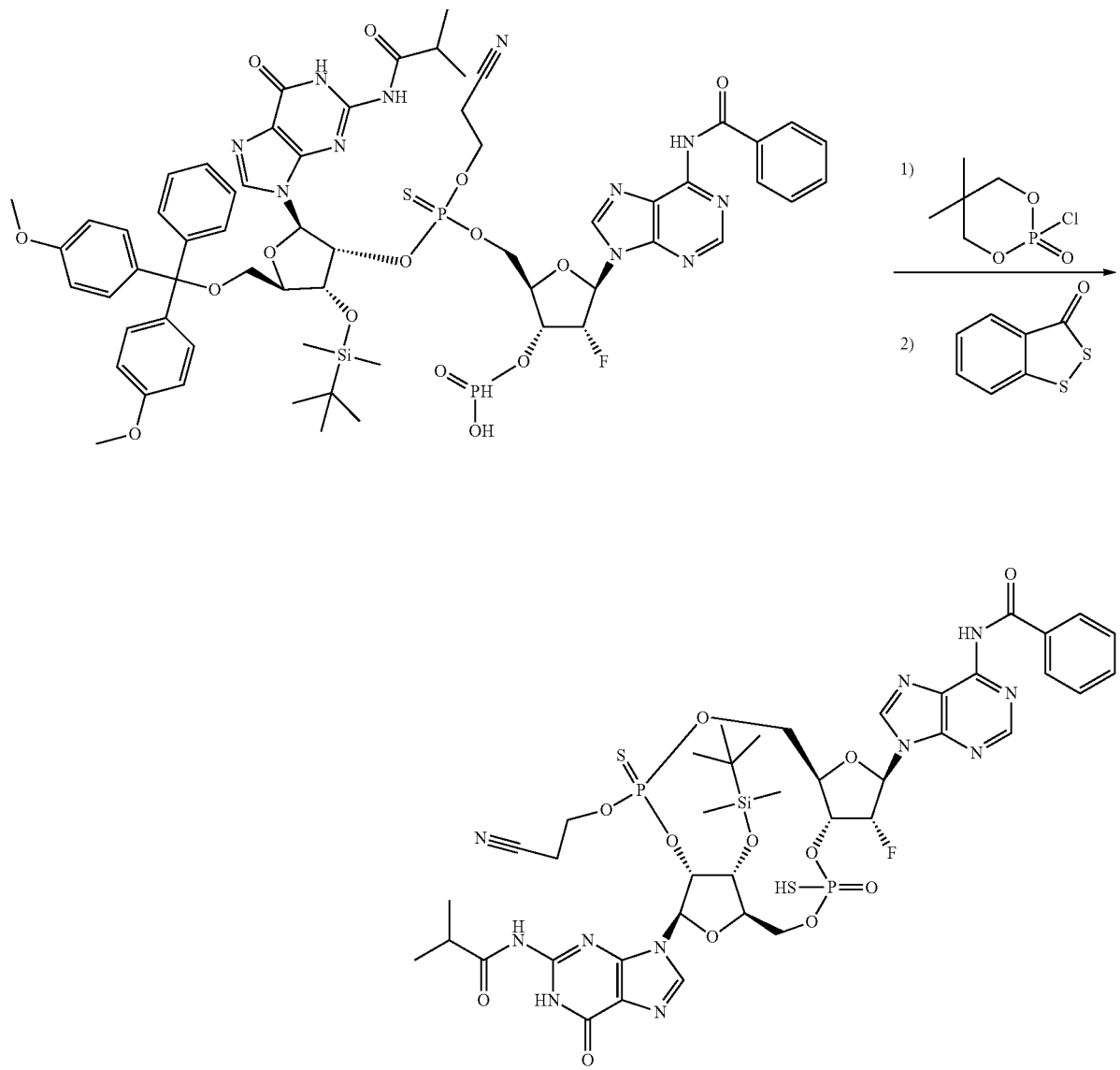

To a crude solution of (2R,5R)-5-(6-benzamido-9H-purin-9-yl)-2-((((((2R,5R)-4-((tert-butyldimethylsilyl)oxy)-5-(hydroxymethyl)-2-(2-isobutyramido-6-oxo-1H-purin-9(6H)-yl)tetrahydrofuran-3-yl)oxy)(2-cyanoethoxy)phosphorothioyl)oxy)methyl)-4-fluorotetrahydrofuran-3-yl hydrogen phosphonate (Intermediate 7, 2.58 g, 2.49 mmol) in pyridine (50 mL) was added 2-chloro-5,5-dimethyl-1,3,2-dioxaphosphinane 2-oxide (DMOCP) (1.70 g, 9.21 mmol), and the mixture was stirred under nitrogen at room temperature for 30 minutes. The reaction was then quenched with water (1.6 mL, 89 mmol), followed by addition of 3H-benzo[c][1,2]dithiol-3-one (660 mg, 3.92 mmol). The mixture was stirred for 10 minutes, then poured into a beaker containing water (350 mL) and sodium bicarbonate (NaHCO$_3$) (10 g, 119 mmol). The yellow slurry was stirred for 10 minutes, then transferred to a separatory funnel. The product was extracted with 1:1 diethyl ether:EtOAc (300 mL×2). The combined extracts were dried over sodium sulfate, filtered, and concentrated in vacuo. The crude material was purified by chromatography on silica (100 gram column) eluting with 0-10% MeOH/DCM, then holding at 10% MeOH/DCM. The desired fractions were combined and concentrated to afford the impure titled compound (1.1 g) as a tan solid. Two major isomers appeared to make up ~77% of the mixture by LCMS. LCMS m/z 1050.1 (M+H), t$_{RET}$=1.09 and 1.20 min, respectively.

Intermediate 11

(1R,6R,8R,9R,10R,15R,17R,18R)-17-(2-amino-6-oxo-6,9-dihydro-1H-purin-9-yl)-8-(6-amino-9H-purin-9-yl)-18-[(tert-butyldimethylsilyl)oxy]l-9-fluoro-3,12-disulfanyl-2,4,7,11,13,16-hexaoxa-3$\lambda^5$,12$\lambda^5$-diphosphatricyclo[13.2.1.0$^{6,10}$]octadecane-3,12-dione a rough ratio of 20:3:13:19 (but the ratio could be significantly affected by possible overlaps with impurity peaks). The volatiles were removed in vacuo. The crude material was purified via reverse phase HPLC, using a gradient of 10-60% ACN:H$_2$O (0.1% TFA). Two major isomers were separated.

Isomer 1 of the titled compound (120 mg, 64% purity by LCMS along with 8% TBS-deprotected product) as a

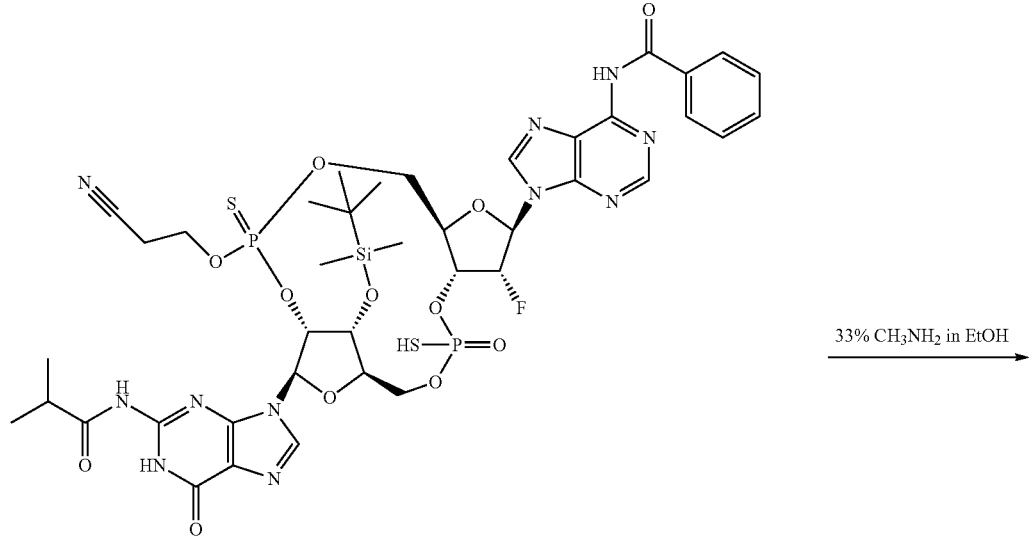

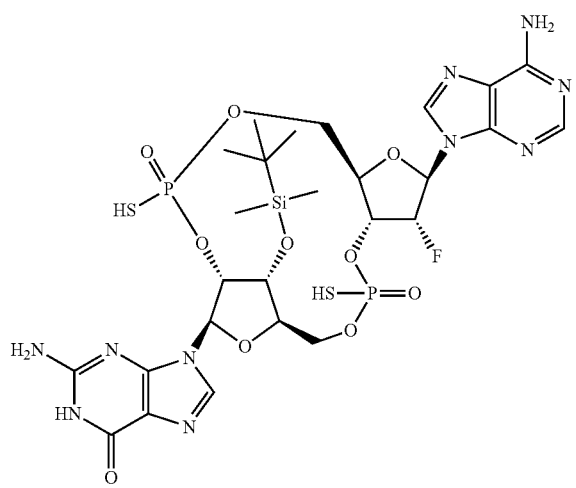

Impure N-{9-[(1R,6R,8R,9R,10R,15R,17R,18R)-18-[(tert-butyldimethylsilyl)oxy]-3-(2-cyanoethoxy)-9-fluoro-17-[2-(2-methylpropanamido)-6-oxo-6,9-dihydro-1H-purin-9-yl]-12-oxo-12-sulfanyl-3-sulfanylidene-2,4,7,11,13,16-hexaoxa-3$\lambda^5$,12$\lambda^5$-diphosphatricyclo[13.2.1.0$^{6,10}$]octadecan-8-yl]-9H-purin-6-yl}benzamide (Intermediate 10, 0.77 g, 0.73 mmol) was stirred in methanamine (33% wt in EtOH) (10.0 mL, 80 mmol) under nitrogen at room temperature for 2 hours. Crude LCMS indicated 4 isomers ((M+H)$^+$=823) with t$_{RET}$=0.74, 0.83, 0.90, and 0.94 min, in tan solid, with the exact stereochemistry at two phosphorus centers undetermined. LCMS m/z 823.1 (M+H). t$_{RET}$=0.74 min.

Isomer 2 of the titled compound (130 mg, 50% purity by LCMS along with 18% TBS-deprotected product) as a tan solid, with the exact stereochemistry at two phosphorus centers undetermined. LCMS m/z 823.1 (M+H). t$_{RET}$=0.96-1.00 min as a broad peak with peak tailing.

Examples 11a and 11b (1R,6R,8R,9R,10R,15R,17R,18R)-17-(2-amino-6-oxo-6,9-dihydro-1H-purin-9-yl)-8-(6-amino-9H-purin-9-yl)-9-fluoro-18-hydroxy-3,12-disulfanyl-2,4,7,11,13,16-hexaoxa-3λ$^5$,12λ$^5$-diphosphatricyclo[13.2.1.0$^{6,10}$]octadecane-3,12-dione, bisammonium salt

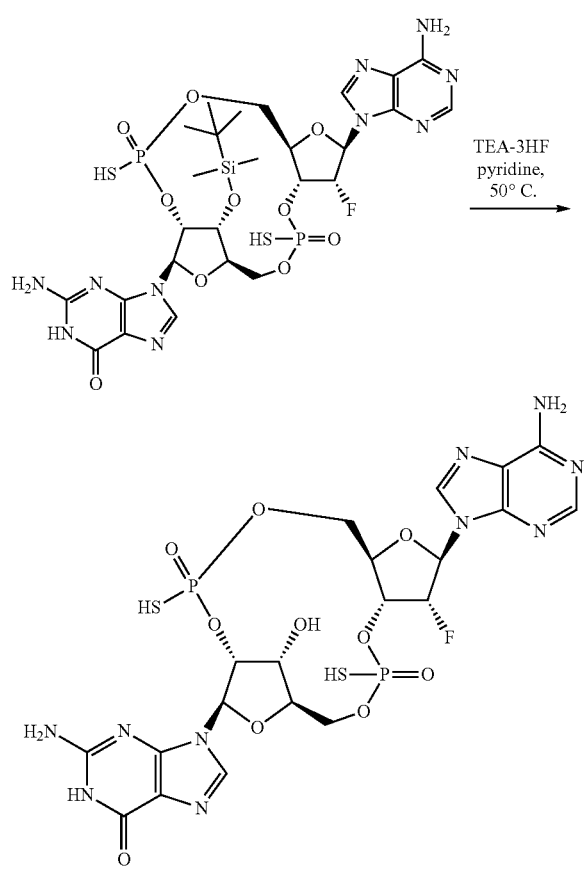

27a - Isomer 1 & 27b - Isomer 2

To a suspension of Isomer 1 of Intermediate 11, (1R,6R,8R,9R,10R,15R,17R,18R)-17-(2-amino-6-oxo-6,9-dihydro-1H-purin-9-yl)-8-(6-amino-9H-purin-9-yl)-18-[(tert-butyldimethylsilyl)oxy]-9-fluoro-3,12-disulfanyl-2,4,7,11,13,16-hexaoxa-3λ$^5$,12λ$^5$-diphosphatricyclo[13.2.1.0$^{6,10}$]octadecane-3,12-dione (120 mg, 0.146 mmol), in pyridine (2 mL) and triethylamine (2 mL) at 50° C. was added triethylamine trihydrofluoride (700 μL, 4.30 mmol) and the mixture was stirred and heated at 50° C. for 4 hours. LCMS indicated that some starting material was still unconsumed. The reaction mixture was left to stir for 16 hours at room temperature. Then acetone (~25 mL) was added and solid precipitated out. This was left to stir at room temperature for ~30 minutes, filtered and rinsed with acetone. The filtered solid did not contain any desired product by LCMS and was discarded. The filtrate, containing the desired product, was concentrated in vacuo and toluene was added to further remove any remaining pyridine. The residue was purified via reverse phase HPLC, using a gradient of 0-10% ACN:H$_2$O (0.1% NH$_4$OH), to afford the product that was not very pure and appeared to be contaminated by trifluoroacetate. So the solid was taken up in ~2 mL of water and added several drops of 30% aqueous NH$_4$OH. It was further purified via reverse phase HPLC, using a gradient of 0-10% ACN:H$_2$O (0.1% NH$_4$OH), to afford the titled compound (Example 11a, 13 mg) as a bisammonium salt as a single diastereomer, with the exact stereochemistry at two phosphorus centers undetermined. The product was a white solid. LCMS m/z 708.9 (M+H). $t_{RET}$=0.17 min.

$^1$H NMR (600 MHz, DMSO-d$_6$ with one drop of D$_2$O): δ ppm 8.31 (s, 1H), 8.21 (s, 1H), 8.11 (br s, 1H), 6.25 (dd, J=15.1, 2.6 Hz, 1H), 5.84 (d, J=8.3 Hz, 1H), 5.68 (d, J=51.7 Hz, 1H), 5.27-5.37 (m, 1H), 5.16-5.25 (m, 1H), 4.32 (d, J=4.2 Hz, 1H), 4.26 (br s, 1H), 4.01-4.17 (m, 3H), 3.90-3.96 (m, 1H), 3.81 (br d, J=11.7 Hz, 1H).

$^{19}$F NMR (376 MHz, DMSO-d$_6$ with one drop of D$_2$O) δ ppm −205.30 (br).

$^{31}$P NMR (162 MHz, DMSO-d$_6$ with one drop of D$_2$O) δ ppm 55.77, 54.01.

Following the same procedure for the preparation of Example 11a, except that the first purification used a gradient of 0-20% ACN:H$_2$O (0.1% NH$_4$OH), the reaction of Isomer 2 of Intermediate 11, (1R,6R,8R,9R,10R,15R,17R,18R)-17-(2-amino-6-oxo-6,9-dihydro-1H-purin-9-yl)-8-(6-amino-9H-purin-9-yl)-18-[(tert-butyldimethylsilyl)oxy]-9-fluoro-3,12-disulfanyl-2,4,7,11,13,16-hexaoxa-3λ$^5$,12λ$^5$-diphosphatricyclo[13.2.1.0$^{6,10}$]octadecane-3,12-dione (130 mg, 0.158 mmol), afforded the titled compound (Example 1b, 16 mg) as a bisammonium salt as a single diastereomer, with the exact stereochemistry at two phosphorus centers undetermined. The product was a white solid. LCMS m/z 708.9 (M+H). $t_{RET}$=0.42 min.

$^1$H NMR (600 MHz, DMSO-d$_6$ with one drop of D$_2$O): δ ppm 8.22 (br s, 1H), 8.18 (s, 1H), 8.05 (br s, 1H), 6.27 (dd, J=15.3, 2.1 Hz, 1H), 5.82 (br d, J=8.3 Hz, 1H), 5.60 (d, J=49.9 Hz, 1H), 5.27-5.46 (m, 1H), 5.12-5.27 (m, 1H), 4.42-4.59 (m, 1H), 4.30 (br s, 1H), 4.14 (br d, J=2.3 Hz, 1H), 4.11 (br d, J=5.7 Hz, 2H), 4.06 (br d, J=9.1 Hz, 1H), 3.82 (br d, J=11.0 Hz, 1H).

$^{19}$F NMR (376 MHz, DMSO-d$_6$ with one drop of D$_2$O) δ ppm −205.05.

$^{31}$P NMR (162 MHz, DMSO-d$_6$ with one drop of D$_2$O) δ ppm 53.85, 47.48.

Abbreviations

The following list provides definitions of certain abbreviations as used herein. It will be appreciated that the list is not exhaustive, but the meaning of those abbreviations not herein below defined will be readily apparent to those skilled in the art.

DCM Dichloromethane
DMF N,N-Dimethylformamide
DMSO Dimethylsulphoxide
DMTr Dimethoxytrityl
THF Tetrahydrofuran
EtOAc Ethyl acetate
MeOH Methanol
EtOH Ethanol
MeCN Acetonitrile
HCl Hydrochloric acid
HPLC High performance liquid chromatography
MDAP Mass Directed Autopreparative HPLC
SPE Solid phase extraction
MeOH Methanol
TBDMS tert-Butyldimethylsilyl
TBME tert-Butyl methy ether TFA Trifluoroacetic acid
DIPEA N, N-Diisopropylethylamine

Nomenclature

The compounds were named from the structure using either the nomenclature tool in Chem Draw (Cambridge-Soft) or Marvin Sketch (ChemAxon).

Example 12

Injectable Composition

An injectable form for administering the present invention is produced by stirring 1.7% by weight of Compound #2 in a 0.9% saline solution.

Assay

The compounds are tested in a STING binding assay similar to that described by Li et al. (Nature Chemical Biology, 10, 1043-1048, (2014)).

Biological Activity

Compounds of the invention were tested in a STING binding assay similar to the one described in Li et al. (*Nature Chemical Biology*, 10, 1043-1048, (2014)). Compounds of the invention were tested in a Fluorescence Resonance Energy Transfer (FRET) binding assay. Li et al. used a Scintillation Proximity Assay (SPA) binding assay.

STING activity for compounds of the invention is listed in Table 1 below.

TABLE 1

| Example | Compound | STING FRET pIC50 |
|---|---|---|
| 8a | 1a | 5.2 |
| 8b | 1b | 6.2 |
| 9a | 2a | 4.9 |
| 9b | 2b | 6.0 |
| 11a | 27a | 7.3 |
| 11b | 27b | 8.4 |
| 10a | 28a | 6.9 |
| 10b | 28b | 8.3 |

While the preferred embodiments of the invention are illustrated by the above, it is to be understood that the invention is not limited to the precise instructions herein disclosed and that the right to all modifications coming within the scope of the following claims is reserved.

The invention claimed is:

1. A compound of Formula (VI):

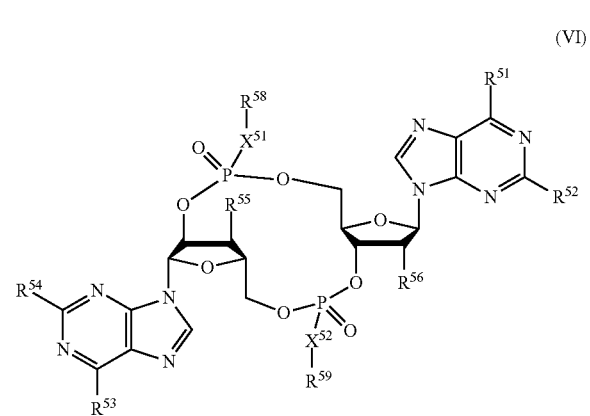

(VI)

wherein:

$X^{51}$ is S;

$X^{52}$ is S;

$R^{51}$ is OH and $R^{52}$ is $NH_2$ or $R^{51}$ is $NH_2$ and $R^{52}$ is H;

$R^{53}$ is OH and $R^{54}$ is $NH_2$ or $R^{53}$ is $NH_2$ and $R^{54}$ is H;

$R^{55}$ is selected from: F and OH;

$R^{56}$ is F;

$R^{58}$ and $R^{59}$ are independently selected from: H, $CH_2OC(O)R^{57}$, $CH_2OCO_2R^{57}$, $CH_2CH_2SC(O)R^{57}$, and $CH_2CH_2SSCH_2R^{57}$;

where $R^{57}$ is selected from: aryl, heteroaryl, heterocycloalkyl, cycloalkyl, $C_{1-20}$alkyl and $C_{1-20}$alkyl substituted with one to 5 substituents independently selected from: aryl, cycloalkyl, hydroxy and F;

provided at least one of $R^{58}$ and $R^{59}$ is not H, and provided that none of $R^{58}$ and $R^{59}$ is $-CH_2OC(O)C(CH_3)_3$, or a pharmaceutically acceptable salt thereof.

2. A compound of claim 1, or a pharmaceutically acceptable salt thereof, wherein:

$R^{55}$ is OH.

3. A compound of claim 1 selected from:

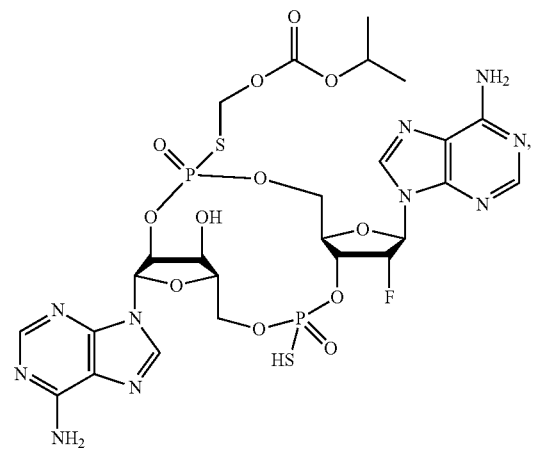

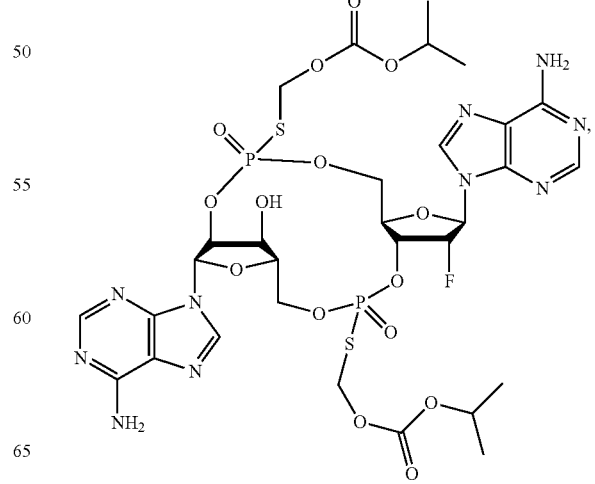

113
-continued

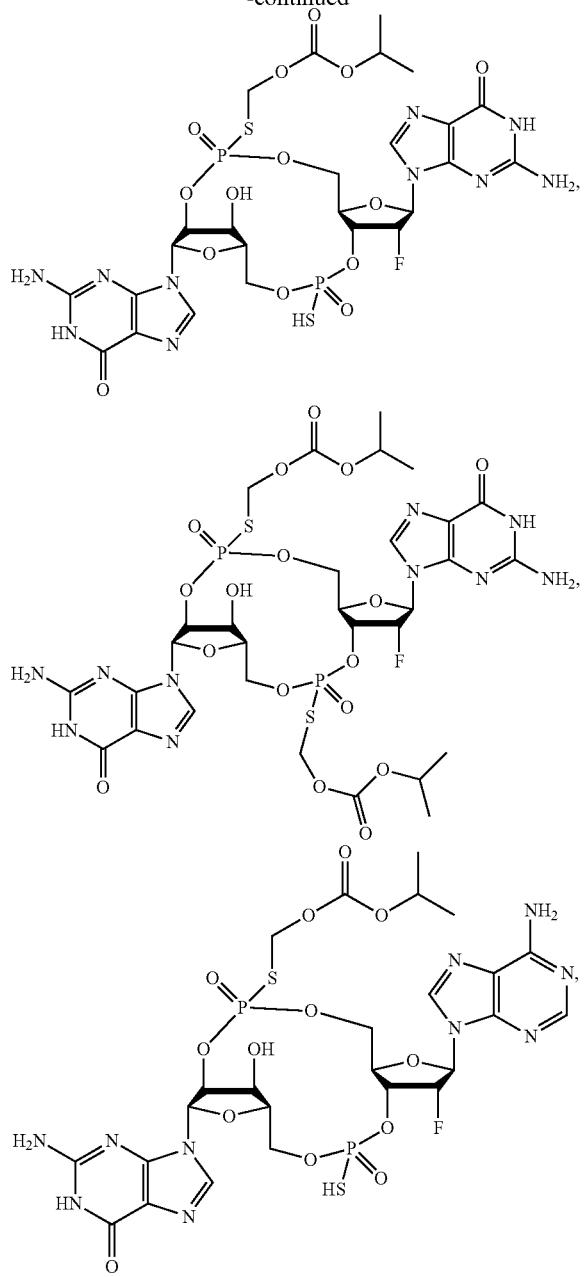

and

114
-continued

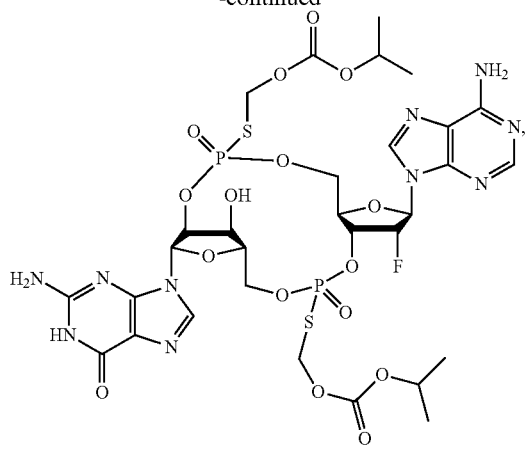

or a pharmaceutically acceptable salt thereof.

4. A pharmaceutical composition comprising a compound of claim 1, or a pharmaceutically acceptable salt thereof, and one or more of pharmaceutically acceptable excipients.

5. A method of treating a disease state selected from: inflammation, allergic diseases, autoimmune diseases, human immunodeficiency virus (HIV), infectious diseases, cancer, and pre-cancerous syndromes, in a mammal in need thereof, which comprises administering to such mammal a therapeutically effective amount of a compound 1, or a pharmaceutically acceptable salt thereof.

6. The method of claim 5 wherein the mammal is a human.

7. A composition comprising a compound of claim 1, or a pharmaceutically acceptable salt thereof, and an antigen or antigen composition.

8. A vaccine composition comprising an antigen or antigen composition and a compound of claim 1, or a pharmaceutically acceptable salt thereof.

9. An immugenic composition comprising an antigen or antigen composition and a compound of claim 1, or a pharmaceutically acceptable salt thereof.

10. A composition comprising a compound of claim 1, or a pharmaceutically acceptable salt thereof, and one or more immunostimulatory agents.

11. A method of treating a disease selected from: HBV, HCV, influenza, skin warts, multiple sclerosis, and allergic inflammation, in a human in need thereof, which comprises administering to such mammal a therapeutically effective amount of a compound, or a pharmaceutically acceptable salt thereof, as described in claim 1.

* * * * *